(12) United States Patent
Ferlin et al.

(10) Patent No.: US 9,682,142 B2
(45) Date of Patent: *Jun. 20, 2017

(54) ANTI-INTERFERON GAMMA ANTIBODIES AND METHODS OF USE THEREOF

(71) Applicant: NovImmune S.A., Geneva (CH)

(72) Inventors: Walter Ferlin, Saint Cergues (FR); Nicolas Fischer, Geneva (CH); Greg Elson, Collonges sous Saleve (FR); Olivier Leger, St. Sixt (FR)

(73) Assignee: NOVIMMUNE S.A., Geneva (CH)

( * ) Notice: Subject to any disclaimer, the term of this patent is extended or adjusted under 35 U.S.C. 154(b) by 647 days.

This patent is subject to a terminal disclaimer.

(21) Appl. No.: 14/057,356

(22) Filed: Oct. 18, 2013

(65) Prior Publication Data

US 2014/0186362 A1 Jul. 3, 2014

Related U.S. Application Data

(63) Continuation of application No. 12/702,013, filed on Feb. 8, 2010, now abandoned, which is a continuation of application No. 11/342,020, filed on Jan. 27, 2006, now Pat. No. 7,700,098.

(60) Provisional application No. 60/648,219, filed on Jan. 27, 2005.

(51) Int. Cl.
*A61K 39/395* (2006.01)
*C07K 16/24* (2006.01)
*A61K 45/06* (2006.01)
*A61K 39/00* (2006.01)

(52) U.S. Cl.
CPC .......... *A61K 39/3955* (2013.01); *A61K 45/06* (2013.01); *C07K 16/249* (2013.01); *A61K 2039/505* (2013.01); *C07K 2317/21* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,727,138 A | 2/1988 | Goeddel et al. |
| 5,096,705 A | 3/1992 | Goeddel et al. |
| 6,534,059 B2 | 3/2003 | Skurkovich et al. |
| 6,558,661 B1 | 5/2003 | Ashkenazi et al. |
| 6,861,056 B2 | 3/2005 | Skurkovich et al. |
| 7,084,257 B2 | 8/2006 | Desphpande et al. |
| 7,115,263 B2 | 10/2006 | Skurkovich et al. |
| 7,335,743 B2 | 2/2008 | Welcher et al. |
| 2008/0107655 A1 | 5/2008 | Welcher et al. |

FOREIGN PATENT DOCUMENTS

| EP | 0695189 A1 | 11/1998 |
| EP | 1401496 A1 | 10/2006 |
| WO | WO 00/32634 | 6/2000 |
| WO | WO 03/097082 | 11/2003 |
| WO | WO 2004/035747 | 4/2004 |
| WO | WO 2004/004306 | 6/2004 |
| WO | WO 2007/106811 | 9/2007 |

OTHER PUBLICATIONS

GenBank Accession No. X13274, "Human mRNA for interferon IFN-gamma".
GenBank Accession No. Z73673.1, "H. sapiens Ig lambda light chain variable region gene (6a.366F5) germline; Ig-Light-Lamda; VLambda".
GenBank Accession No. M997660.1, "Human immunoglobulin heavy chain variable region V323 (IGHV@) gene, exons 1-2".

*Primary Examiner* — Zachary Skelding
(74) *Attorney, Agent, or Firm* — Cooley LLP; Ivor R. Elrifi

(57) ABSTRACT

The invention relates to fully human antibodies, and fragments thereof, that bind to human interferon gamma (hIFNγ), thereby modulating the interaction between IFNγ and its receptor, IFNγ-R, and/or modulating the biological activities of IFNγ. The invention also relates to the use of such anti-IFNγ antibodies in the prevention or treatment of immune-related disorders and in the amelioration of a symptom associated with an immune-related disorder.

10 Claims, 24 Drawing Sheets

VH NUCLEOTIDE SEQUENCE

```
  1  GAGGTGCAGC TGTTGGAGTC TGGGGGAGGC TTGGTACAGC CTGGGGGGTC CCTGAGACTC
         e  v  q   l  l  e   s  g  g   l  v  q   p  g  g   s  l  r  l
 61  TCCTGTGCAG CCTCTGGATT CACCTTTAGC AGCTATGCCA TGAGCTGGGT CCGCCAGGCT
      s  c   a  a  s   g  f  t  f   s  s  y   a  m  s   w  v  r   q  a
121  CCAGGGAAGG GGCTGGAGTG GGTCTCAGCT ATTAGTGGTA GTGGTGGTAG CACATACTAC
      p  g  k   g  l  e   w  v  s   a  i  s   g  s  g   g  s  t   y  y
181  GCAGACTCCG TGAAGGGCCG GTTCACCATC TCCAGAGACA ATTCCAAGAA CACGCTGTAT
      a  d  s   v  k  g   r  f  t   i  s  r   d  n  s   k  n  t   l  y
241  CTGCAAATGA ACAGCCTGAG AGCCGAGGAC ACGGCCGTAT ATTACTGTGC GAAAGATGGT
      l  q  m   n  s  l   r  a  e   d  t  a   v  y  y   c  a  k   d  g
301  AGCAGTGGCT GGTACGTACC ACACTGGTTC GACCCCTGGG GCCAGGGCAC CCTGGTCACC
      s  s  g   w  y  v   p  h  w  f   d  p  w   g  q  g   t  l  v  t
361  GTCTCCTCA  (SEQ ID NO:1)
      v  s  s  (SEQ ID NO:2)
```

Fig. 1A

VH PROTEIN SEQUENCE

```
                        (SEQ ID NO:3)            (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDG SSGWYVPHWF DPWGQGTLVT
121  VSS (SEQ ID NO:2)                           (SEQ ID NO:5)
```

Fig. 1B

VL NUCLEOTIDE SEQUENCE

```
  1  AATTTTATGC TGACTCAGCC CCACTCTGTG TCGGAGTCTC CGGGGAAGAC GGTAACCATC
         n  f  m   l  t  q   p  h  s   v  s  e   s  p  g   k  t  v  t  i
 61  TCCTGCACTC GCAGCAGTGG CAGCATTGCC AGCAACTATG TGCAGTGGTA CCAACAGCGC
      s  c  t   r  s  s   g  s  i   a  s  n   y  v  q   w  y  q   q  r
121  CCGGGCAGTT CCCCCACCAC TGTCATCTAT GAGGATAACC AGAGACCCTC TGGGGTCCCT
      p  g  s   s  p  t   t  v  i  y   e  d  n   q  r  p   s  g  v  p
181  GATCGGTTCT CTGGCTCCAT CGACAGCTCC TCCAATTCTG CCTCCCTCAC CATCTCTGGG
      d  r  f   s  g  s   i  d  s   s  s  n   s  a  s   l  t  i  s   g
241  CTGAAGACTG AGGACGAGGC TGACTACTAC TGTCAGTCTT ATGATGGCAG CAATCGTTGG
      l  k  t   e  d  e   a  d  y  y   c  q  s   y  d  g   s  n  r  w
301  ATGTTCGGCG GAGGGACCAA GCTGACCGTC CTA  (SEQ ID NO:6)
      m  f  g   g  g  t   k  l  t  v   l  (SEQ ID NO:7)
```

Fig. 1C

VL PROTEIN SEQUENCE

```
                        (SEQ ID NO:8)             (SEQ ID NO:9)
  1  NFMLTQPHSV SESPGKTVTI SCTRSSGSIA SNYVQWYQQR PGSSPTTVIY EDNQRPSGVP
 61  DRFSGSIDSS SNSASLTISG LKTEDEADYY CQSYDGSNRW MFGGGTKLTV L (SEQ ID NO:7)
                                      (SEQ ID NO:10)
```

Fig. 1D

VH NUCLEOTIDE SEQUENCE

```
  1 GAGGTGCAGC TGTTGGAGTC TGGGGGAGGC TTGGTACAGC CTGGGGGGTC CCTGAGACTC
     e  v  q   l  l  e    s  g  g  g   l  v  q   p  g  g    s  l  r  l
 61 TCCTGTGCAG CCTCTGGATT CACCTTTAGC AGCTATGCCA TGAGCTGGGT CCGCCAGGCT
     s  c  a   a  s  g    f  t  f  s   s  y  a   m  s  w   v  r  q  a
121 CCAGGGAAGG GGCTGGAGTG GGTCTCAGCT ATTAGTGGTA GTGGTGGTAG CACATACTAC
     p  g  k   g  l  e    w  v  s  a   i  s  g   s  g  g   s  t  y  y
181 GCAGACTCCG TGAAGGGCCG GTTCACCATC TCCAGAGACA ATTCCAAGAA CACGCTGTAT
     a  d  s   v  k  g    r  f  t  i   s  r  d   n  s  k   n  t  l  y
241 CTGCAAATGA ACAGCCTGAG AGCCGAGGAC ACGGCCGTAT ATTACTGTGC GAAAGATGGT
     l  q  m   n  s  l    r  a  e  d   t  a  v   y  y  c   a  k  d  g
301 AGCAGTGGCT GGTACGTACC ACACTGGTTC GACCCCTGGG GCCGGGGCAC CCTGGTCACC
     s  s  g   w  y  v    p  h  w  f   d  p  w   g  r  g   t  l  v  t
361 GTCTCGAGT (SEQ ID NO:102)
     v  s  s  (SEQ ID NO:103)
```

Fig. 1E

VH PROTEIN SEQUENCE

```
                      (SEQ ID NO:3)              (SEQ ID NO:4)
  1 EVQLLESGGG LVQPGGSLRL SCAASGFTFS SYAMSWVRQA PGKGLEWVSA ISGSGGSTYY
 61 ADSVKGRFTI SRDNSKNTLY LQMNSLRAED TAVYYCAKDG SSGWYVPHWF DPWGRGTLVT
121 VSS (SEQ ID NO:103)                           (SEQ ID NO:5)
```

Fig. 1F

VL NUCLEOTIDE SEQUENCE

```
  1 AATTTTATGC TGACTCAGCC CCACTCTGTG TCGGAGTCTC CGGGGAAGAC GGTAACCATC
     n  f  m   l  t  q    p  h  s  v   s  e  s   p  g  k   t  v  t  i
 61 TCCTGCACTC GCAGCAGTGG CAGCATTGTC AGCAACTATG TGCAGTGGTA CCAACAGCGC
     s  c  t   r  s  s    g  s  i  v   s  n  y   v  q  w   y  q  q  r
121 CCGGGCAGTG CCCCCACCAC TGTCATCTAT GAGGATAACC GGAGACCCTC TGGGGTCCCT
     p  g  s   a  p  t    t  v  i  y   e  d  n   r  r  p   s  g  v  p
181 GATCGGTTCT CTGGCTCCAT CGACAGCTCC TCCAATACTG CCTCCCTCAC CATCTCTGGG
     d  r  f   s  g  s    i  d  s  s   s  n  t   a  s  l   t  i  s  g
241 CTGGAGGCTG AGGACGAGGC TGACTACTAC TGTCAGTCTT ATGATGGCAG CAATCGTTGG
     l  e  a   e  d  e    a  d  y  y   c  q  s   y  d  g   s  n  r  w
301 ATGTTCGGCG GAGGGACCAA GCTGACCGTC CTAGGT (SEQ ID NO:104)
     m  f  g   g  g  t    k  l  t  v   l  g (SEQ ID NO:105)
```

Fig. 1G

VL PROTEIN SEQUENCE

```
                      (SEQ ID NO:106)           (SEQ ID NO:107)
  1 NFMLTQPHSV SESPGKTVTI SCTRSSGSIV SNYVQWYQQR PGSAPTTVIY EDNRRPSGVP
 61 DRFSGSIDSS SNTASLTISG LEAEDEADYY CQSYDGSNRW MFGGGTKLTV LG (SEQ ID NO:105)
                                     (SEQ ID NO:10)
```

Fig. 1H

VH NUCLEOTIDE SEQUENCE

```
  1  GAGGTGCAGC TGTTGGAGTC TGGGGGAGGC TTGGTACAGC CTGGGGGGTC CCTGAGACTC
      e   v   q   l   l   e   s   g   g   g   l   v   q   p   g   g   s   l   r   l
 61  TCCTGTGCAG CCTCTGGATT CACCTTTAGC AGCTATGCCA TGAGCTGGGT CCGCCAGGCT
      s   c   a   a   s   g   f   t   f   s   s   y   a   m   s   w   v   r   q   a
121  CCAGGGAAGG GGCTGGAGTG GGTCTCAGCT ATTAGTGGTA GTGGTGGTAG CACATACTAC
      p   g   k   g   l   e   w   v   s   a   i   s   g   s   g   g   s   t   y   y
181  GCAGACTCCG TGAAGGGCCG GTTCACCATC TCCAGAGACA ATTCCAAGAA CACGCTGTAT
      a   d   s   v   k   g   r   f   t   i   s   r   d   n   s   k   n   t   l   y
241  CTGCAAATGA ACAGCCTGAG AGCCGAGGAC ACGGCCGTAT ATTACTGTGC GAAAGATCAT
      l   q   m   n   s   l   r   a   e   d   t   a   v   y   y   c   a   k   d   h
301  AGCAGTGGCT GGTACGTAAT CTCCGGTATG GACGTCTGGG GCCGAGGGAC AATGGTCACC
      s   s   g   w   y   v   i   s   g   m   d   v   w   g   r   g   t   m   v   t
361  GTCTCGAGT (SEQ ID NO:11)
      v   s   s   (SEQ ID NO:12)
```

Fig. 2A

VH PROTEIN SEQUENCE

```
                                  (SEQ ID NO:3)              (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDH SSGWYVISGM DVWGRGTMVT
121  VSS (SEQ ID NO:12)                         (SEQ ID NO:13)
```

Fig. 2B

VL NUCLEOTIDE SEQUENCE

```
  1  AATTTTATGC TGACTCAGCC CCACTCTGTG TCGGAGTCTC CGGGGAAGAC GGTAACCATC
      n   f   m   l   t   q   p   h   s   v   s   e   s   p   g   k   t   v   t   i
 61  TCCTGCACCC GCAGCAGTGG CAGCATTGCC AGCAACTATG TGCAGTGGTA CCAGCAGCGC
      s   c   t   r   s   s   g   s   i   a   s   n   y   v   q   w   y   q   q   r
121  CCGGGCAGTT CCCCCACCAC TGTGATCTCT GAGGATAACC AAAGACCCTC TGGGGTCCCT
      p   g   s   s   p   t   t   v   i   s   e   d   n   q   r   p   s   g   v   p
181  GATCGGTTCT CTGGCTCCGT CGACAGCTCC TCCAACTCTG CCTCCCTCAC CATTTCTGGA
      d   r   f   s   g   s   v   d   s   s   s   n   s   a   s   l   t   i   s   g
241  CTGAGGACTG AGGACGAGGC TGACTATTAC TGTCAGTCTA ATGATTCCGA CAATGTGGTT
      l   r   t   e   d   e   a   d   y   y   c   q   s   n   d   s   d   n   v   v
301  TTCGGCGGAG GGACCAAGCT GACCGTCCTA GGT (SEQ ID NO:14)
      f   g   g   g   t   k   l   t   v   l   g  (SEQ ID NO:15)
```

Fig. 2C

VL PROTEIN SEQUENCE

```
                (SEQ ID NO:16)                   (SEQ ID NO:17)
  1  NFMLTQPHSV SESPGKTVTI SCTRSSGSIA SNYVQWYQQR PGSSPTTVIS EDNQRPSGVP
 61  DRFSGSVDSS SNSASLTISG LRTEDEADYY CQSNDSDNVV FGGGTKLTVL G (SEQ ID NO:15)
                                      (SEQ ID NO:18)
```

Fig. 2D

VH NUCLEOTIDE SEQUENCE

```
  1  GAGGTGCAGC TGTTGGAGTC TGGGGGAGGC TTGGTACAGC CTGGGGGGTC CCTGAGACTC
      e  v  q   l  l  e   s  g  g   l  v  q   p  g  g   s  l  r  l
 61  TCCTGTGCAG CCTCTGGATT CACCTTTAGC AGCTATGCCA TGAGCTGGGT CCGCCAGGCT
      s  c  a   a  s  g   f  t  f   s  y  a   m  s  w   v  r  q  a
121  CCAGGGAAGG GGCTGGAGTG GGTCTCAGCT ATTAGTGGTA GTGGTGGTAG CACATACTAC
      p  g  k   g  l  e   w  v  s   a  i  s   g  s  g   s  t  y  y
181  GCAGACTCCG TGAAGGGCCG GTTCACCATC TCCAGAGACA ATCCCAAGAA CACGCTGTAT
      a  d  s   v  k  g   r  f  t   i  s  r   d  n  p   k  n  t  l  y
241  CTGCAAATGA ACAGCCTGAG AGCCGAGGAC ACGGCCGTGT ATTACTGTGC GAAGGACCTA
      l  q  m   n  s  l   r  a  e   d  t  a   v  y  y   c  a  k  d  l
301  ACAGTGGGTG GTCCCTGGTA CTACTTTGAC TACTGGGGCC AAGGAACCCT GGTCACCGTC
      t  v  g   g  p  w   y  y  f   d  y  w   g  q  g   t  l  v  t  v
361  TCGAGT (SEQ ID NO:19)
      s  s  (SEQ ID NO:20)
```

Fig. 3A

VH PROTEIN SEQUENCE

```
                         (SEQ ID NO:3)              (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNPKNTLY LQMNSLRAED TAVYYCAKDL TVGGPWYYFD YWGQGTLVTV
121  SS (SEQ ID NO:20)                           (SEQ ID NO:21)
```

Fig. 3B

VL NUCLEOTIDE SEQUENCE

```
  1  AATTTTATGC TGACTCAGCC CCACTCTGTG TCGGAGTCTC CGGGGAAGAC GGTAACCATC
      n  f  m   l  t  q   p  h  s   v  s  e   s  p  g   k  t  v  t  i
 61  TCCTGCACCC GCAGCAGTGG CAGCATTGTC AGCAACTATG TGCAGTGGTA CCAGCAGCGC
      s  c  t   r  s  s   g  s  i   v  s  n   y  v  q   w  y  q  q  r
121  CCGGGCAGTG CCCCCACCAC TGTGATCTTT GACGATGACC AAAGACCCTC TGGGGTCCCT
      p  g  s   a  p  t   t  v  i   f  d  d   d  q  r   p  s  g  v  p
181  GGTCGGTTCT CTGGCTCCCT CGACAGCTCC TCCAACTCTG CCTCCCTCAC CATCTCTGGG
      g  r  f   s  g  s   l  d  s   s  n  s   a  s  l   t  i  s  g
241  CTGCAGACTG AGGACGAGGC TGACTACTAC TGTCAGTCTT ATGATAGCAG CAATGTGGTA
      l  q  t   e  d  e   a  d  y   y  c  q   s  y  d   s  s  n  v  v
301  TTCGGCGGGG GGACCAAGGT CACCGTCCTA GGT (SEQ ID NO:22)
      f  g  g   g  t  k   v  t  v   l  g (SEQ ID NO:23)
```

Fig. 3C

VL PROTEIN SEQUENCE

```
                         (SEQ ID NO:8)                       (SEQ ID NO:25)
  1  NFMLTQPHSV SESPGKTVTI SCTRSSGSIV SNYVQWYQQR PGSAPTTVIF DDDQRPSGVP
 61  GRFSGSLDSS SNSASLTISG LQTEDEADYY CQSYDSSNVV FGGGTKVTVL G (SEQ ID NO:23)
                                         (SEQ ID NO:26)
```

Fig. 3D

VH NUCLEOTIDE SEQUENCE

```
  1  GAGGTGCAGC TGTTGGAGTC TGGGGGAGGC TTGGTACAGC CTGGGGGGTC CCTGAGACTC
      e  v  q   l  l  e    s  g  g    l  v  q    p  g  g    s  l  r  l
 61  TCCTGTGCAG CCTCTGGATT CACCTTTAGC AGCTATGCCA TGAGCTGGGT CCGCCAGGCT
      s  c  a   s  g  f    t  f  s    s  y  a    m  s  w    v  r  q  a
121  CCAGGGAAGG GGCTGGAGTG GGTCTCAGCT ATTAGTGGTA GTGGTGGTAG CACATACTAC
      p  g  k   g  l  e    w  v  s  a  i  s  g   s  g  g    s  t  y  y
181  GCAGACTCCG TGAAGGGCCG GTTCACCATC TCCAGAGACA ATTCCAAGAA CACGCTGTAT
      a  d  s   v  k  g    r  f  t  i  s  r  d   n  s  k    n  t  l  y
241  CTGCAAATGA ACAGCCTGAG AGCCGAGGAC ACGGCCGTGT ATTACTGTGC GAAAGATGGA
      l  q  m   n  s  l    r  a  e  d  t  a  v   y  y  c    a  k  d  g
301  TGGAACGCGC TGGGATGGCT TGAATCCTGG GGCCGGGGCA CCCTGGTCAC
      w  n  a   l  g  w    l  e  s  w  g  r  g   t  l  v
351  CGTCTCGAGT (SEQ ID NO:27)
      t  v  s  s  (SEQ ID NO:28)
```

Fig. 4A

VH PROTEIN SEQUENCE

```
                          (SEQ ID NO:3)          (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDG WNALGWLESW GRGTLVTVSS (SEQ
ID NO:28)                                        (SEQ ID NO:29)
```

Fig. 4B

VL NUCLEOTIDE SEQUENCE

```
  1  AATTTTATGC TGACTCAGCC CCACTCTGTG TCGGAGTCTC CGGGGAGGAC GATAACCATC
      n  f  m   l  t  q    p  h  s  v  s  e  s   p  g  r    t  i  t  i
 61  TCCTGCACCC GCAGTGGTGG CAGCATTGGC AGCTACTATG TGCAGTGGTA CCAGCAGCGC
      s  c  t   r  s  g    g  s  i  g  s  y  y   v  q  w    y  q  q  r
121  CCGGGCACTG CCCCCACCAC TGTGATCTAT GACGATAAAA AAGACCCTC TGGGGTCCCT
      p  g  t   a  p  t    t  v  i  y  d  d  k   k  r  p    s  g  v  p
181  GATCGGTTCT CTGGCTCCAT CGACAGCTCC TCCAACTCTG CCTCCCTCAC CATCTCTGGA
      d  r  f   s  g  s    i  d  s  s  s  n  s   a  s  l    t  i  s  g
241  CTGAAGACTG AGGACGAGGC TGACTACTAT TGTCAGTCTT ATGATAGCAA CAATCTTGTG
      l  k  t   e  d  e    a  d  y  y  c  q  s   y  d  s    n  n  l  v
301  GTTTTCGGCG GAGGGACCAA GGTCACCGTC CTAGGT (SEQ ID NO:30)
      v  f  g   g  g  t    k  v  t  v  l  g  (SEQ ID NO:31)
```

Fig. 4C

VL PROTEIN SEQUENCE

```
                          (SEQ ID NO:32)                  (SEQ ID NO:33)
  1  NFMLTQPHSV SESPGRTITI SCTRSGGSIG SYYVQWYQQR PGTAPTTVIY DDKKRPSGVP
 61  DRFSGSIDSS SNSASLTISG LKTEDEADYY CQSYDSNNLV VFGGGTKVTV LG (SEQ ID NO:31)
                                      (SEQ ID NO:34)
```

Fig. 4D

VH NUCLEOTIDE SEQUENCE

```
  1  GAGGTGCAGC TGTTGGAGTC TGGGGGAGGC TTGGTACAGC CTGGGGGGTC CCTGAGACTC
      e  v  q  l  l  e  s  g  g  g  l  v  q  p  g  g  s  l  r  l
 61  TCCTGTGCAG CCTCTGGATT CACCTTTAGC AGCTATGCCA TGAGCTGGGT CCGCCAGGCT
      s  c  a  a  s  g  f  t  f  s  s  y  a  m  s  w  v  r  q  a
121  CCAGGGAAGG GGCTGGAGTG GGTCTCAGCT ATTAGTGGTA GTGGTGGTAG CACATACTAC
      p  g  k  g  l  e  w  v  s  a  i  s  g  s  g  g  s  t  y  y
181  GCAGACTCCG TGAAGGGCCG GTTCACCATC TCCAGAGACA ATTCCAAGAA CACGCTGTAT
      a  d  s  v  k  g  r  f  t  i  s  r  d  n  s  k  n  t  l  y
241  CTGCAAATGA ACAGCCTGAG AGCCGAGGAC ACGGCCGTAT ATTACTGTGC GAAAGATGGT
      l  q  m  n  s  l  r  a  e  d  t  a  v  y  y  c  a  k  d  g
301  AGCAGTGGCT GGTACGTACC ACACTGGTTC GACCCCTGGG GCAGGGGAC AATGGTCACC
      s  s  g  w  y  v  p  h  w  f  d  p  w  g  r  g  t  m  v  t
361  GTCTCGAGT (SEQ ID NO:35)
      v  s  s  (SEQ ID NO:36)
```

Fig. 5A

VH PROTEIN SEQUENCE

```
                                  (SEQ ID NO:3)          (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDG SSGWYVPHWF DPWGRGTMVT
121  VSS (SEQ ID NO:36)                          (SEQ ID NO:5)
```

Fig. 5B

VL NUCLEOTIDE SEQUENCE

```
  1  AATTTTATGC TGACTCAGCC CCACTCTGTG TCGGAGTCTC CGGGGAAGAC GGTAACCATC
      n  f  m  l  t  q  p  h  s  v  s  e  s  p  g  k  t  v  t  i
 61  TCCTGCACCC GCAGCAGTGG CACCATTGCC AGCAACTATG TGCAGTGGTA CCAGCAGCGC
      s  c  t  r  s  s  g  t  i  a  s  n  y  v  q  w  y  q  q  r
121  CCGGGCAGTT CCCCCACCAC TGTGATCTAT GAGGATAACC AAAGACCCTC TGGGGTCCCT
      p  g  s  s  p  t  t  v  i  y  e  d  n  q  r  p  s  g  v  p
181  GATCGGTTCT CTGGCTCCAT CGACAGCTCC TCCAACTCTG CCTCCCTCAC CATCTCTGGA
      d  r  f  s  g  s  i  d  s  s  n  s  a  s  l  t  i  s  g
241  CTGAAGACTG AGGACGAGGC TGACTACTAC TGTCAGTCTT ATGATAACAG CAATCATTGG
      l  k  t  e  d  e  a  d  y  y  c  q  s  y  d  n  s  n  h  w
301  GTGTTCGGCG GAGGGACCAA GGTCACCGTC CTAGGT (SEQ ID NO:37)
      v  f  g  g  g  t  k  v  t  v  l  g  (SEQ ID NO:38)
```

Fig. 5C

VL PROTEIN SEQUENCE

```
                   (SEQ ID NO:39)                  (SEQ ID NO:17)
  1  NFMLTQPHSV SESPGKTVTI SCTRSSGTIA SNYVQWYQQR PGSSPTTVIY EDNQRPSGVP
 61  DRFSGSIDSS SNSASLTISG LKTEDEADYY CQSYDNSNHW VFGGGTKVTV LG (SEQ ID NO:38)
                                      (SEQ ID NO:40)
```

Fig. 5D

VH NUCLEOTIDE SEQUENCE

```
  1  GAGGTGCAGC TGTTGGAGTC TGGGGGAGGC TTGGTACAGC CAGGGGGGTC CCTGAAACTC
        e  v  q  l  l  e  s  g  g  g  l  v  q  p  g  g  s  l  k  l
 61  TCCTGTGCAG CCTCTGGATT CACCTTTAGC AGCAATGCCA TGAGTTGGGT CCGCCAGGCT
        s  c  a  a  s  g  f  t  f  s  s  n  a  m  s  w  v  r  q  a
121  CCAGGGAAGG GGCTGGAGTG GGTCTCAACT CTTACTGGTA GTGGTGGTAC CGCATACTAC
        p  g  k  g  l  e  w  v  s  t  l  t  g  s  g  g  t  a  y  y
181  GCAGACTCCG TGGAGGGCCG GTTCAGCATC TCCAGAGACA ATTCCAAGAA CACACTGTAT
        a  d  s  v  e  g  r  f  s  i  s  r  d  n  s  k  n  t  l  y
241  CTGCAAATGA ACAGCCTGAG AGCCGAGGAC ACGGCCGTAT ATTACTGTGC GAAGGGCACG
        l  q  m  n  s  l  r  a  e  d  t  a  v  y  y  c  a  k  g  t
301  GAACTCGTGG GAGGAGGACT TGACAACTGG GGCCAAGGCA CCCTGGTCAC
        e  l  v  g  g  g  l  d  n  w  g  q  g  t  l  v
351  CGTCTCGAGT (SEQ ID NO:41)
        t  v  s  s  (SEQ ID NO:42)
```

Fig. 6A

VH PROTEIN SEQUENCE

```
                              (SEQ ID NO:43)      (SEQ ID NO:44)
  1  EVQLLESGGG LVQPGGSLKL SCAASGFTFS SNAMSWVRQA PGKGLEWVST LTGSGGTAYY
 61  ADSVEGRFSI SRDNSKNTLY LQMNSLRAED TAVYYCAKGT ELVGGGLDNW GQGTLVTVSS (SEQ
ID NO:42)                                         (SEQ ID NO:45)
```

Fig. 6B

VL NUCLEOTIDE SEQUENCE

```
  1  AATTTTATGC TGACTCAGCC CCACTCTCTG TCGGAGTCTC CGGGGAAGAC GGTGACGATC
        n  f  m  l  t  q  p  h  s  l  s  e  s  p  g  k  t  v  t  i
 61  TCCTGCACCG GCAGCGGAGG CAGCATTGCC ACCAACTATG TGCAGTGGTA TCAGCAGCGC
        s  c  t  g  s  g  g  s  i  a  t  n  y  v  q  w  y  q  q  r
121  CCGGGCAGTG CCCCCACCAC TGTGATCCAT GAGGATAACC AAAGACCCTC TGGGGTCCCT
        p  g  s  a  p  t  t  v  i  h  e  d  n  q  r  p  s  g  v  p
181  GATCGGTTCT CTGGCTCCAT CGACGGCTCC TCCAACTCTG CCTCCCTCAC CATCTCTGGA
        d  r  f  s  g  s  i  d  g  s  s  n  s  a  s  l  t  i  s  g
241  CTGCAGCCTG AGGACGAGGC TGATTACTAC TGTCAGTCTT ATGATAGTGA CAATCATCAT
        l  q  p  e  d  e  a  d  y  y  c  q  s  y  d  s  d  n  h  h
301  GTGGTATTCG GCGGAGGGAC CAAGCTGACC GTCCTAGGT (SEQ ID NO:46)
        v  v  f  g  g  g  t  k  l  t  v  l  g  (SEQ ID NO:47)
```

Fig. 6C

VL PROTEIN SEQUENCE

```
                (SEQ ID NO:48)                    (SEQ ID NO:17)
  1  NFMLTQPHSL SESPGKTVTI SCTGSGGSIA TNYVQWYQQR PGSAPTTVIH EDNQRPSGVP
 61  DRFSGSIDGS SNSASLTISG LQPEDEADYY CQSYDSDNHH VVFGGGTKLT VLG (SEQ ID NO:47)
                                      (SEQ ID NO:49)
```

Fig. 6D

VH NUCLEOTIDE SEQUENCE

```
  1 GAGGTGCAGC TGTTGGAGTC TGGGGGAGGC TTGGTACAGC CTGGGGGGTC CCTGAGACTC
     e  v  q   l  l  e   s  g  g   l  v  q   p  g  g   s  l  r  l
 61 TCCTGTGCAG CCTCTGGATT CACCTTTAGC AGCTATGCCA TGAGCTGGGT CCGCCAGGCT
     s  c  a   a  s  g   f  t  f  s   s  y  a  m  s   w  v  r  q  a
121 CCAGGGAAGG GGCTGGAGTG GGTCTCAGCT ATTAGTGGTA GTGGTGGTAG CACATACTAC
     p  g  k   g  l  e   w  v  s  a  i  s  g   s  g  g   s  t  y  y
181 GCAGACTCCG TGAAGGGCCG GTTCACCATC TCCAGAGACA ATTCCAAGAA CACGCTGTAT
     a  d  s   v  k  g   r  f  t  i   s  r  d   n  s  k   n  t  l  y
241 CTGCAAATGA ACAGCCTGAG AGCCGAGGAC ACGGCCGTGT ATTACTGTGC GAAAGATGGA
     l  q  m   n  s  l   r  a  e  d   t  a  v   y  y  c   a  k  d  g
301 TGGAACGCGC TGGGATGGCT TGAATCCTGG GGCAAGGGGA CAATGGTCAC
     w  n  a   l  g  w   l  e  s  w   g  k  g   t  m  v
351 CGTCTCGAGT (SEQ ID NO:50)
     t  v  s  s (SEQ ID NO:51)
```

Fig. 7A

VH PROTEIN SEQUENCE

```
                                  (SEQ ID NO:3)          (SEQ ID NO:4)
  1 EVQLLESGGG LVQPGGSLRL SCAASGFTFS SYAMSWVRQA PGKGLEWVSA ISGSGGSTYY
 61 ADSVKGRFTI SRDNSKNTLY LQMNSLRAED TAVYYCAKDG WNALGWLESW GKGTMVTVSS (SEQ
ID NO:51)                                       (SEQ ID NO:29)
```

Fig. 7B

VL NUCLEOTIDE SEQUENCE

```
  1 AATTTTATGC TGACTCAGCC CCACTCTGTG TCGGAGTCTC CGGGGAAGAC GGTAACCATC
     n  f  m   l  t  q   p  h  s  v   s  e  s   p  g  k   t  v  t  i
 61 TCCTGCACCG GCAGCAGTGG CAGCATTGCC AGCAACTATG TGCAGTGGTA CCAGCAGCGC
     s  c  t   g  s  s   g  s  i  a   s  n  y   v  q  w   y  q  q  r
121 CCGGGCAGTG CCCCCACCAC TGTGATCTAT GAGGATAACC AAAGACCCTC TGGGGTCCCT
     p  g  s   a  p  t   t  v  i  y   e  d  n   q  r  p   s  g  v  p
181 GATCGGTTCT CTGGCTCCAT CGACAGCTCC TCCAACTCTG CCTCCCTCAC CATCTCTGGA
     d  r  f   s  g  s   i  d  s  s   s  n  s   a  s  l   t  i  s  g
241 CTGAAGACTG AGGACGAGGC TGACTACTAC TGTCAGTCTT ATGATAGCAG CAATCAAGAG
     l  k  t   e  d  e   a  d  y  y   c  q  s   y  d  s   s  n  q  e
301 GTGGTATTCG GCGGAGGGAC CAAGCTGACC GTCCTAGGT (SEQ ID NO:53)
     v  v  f   g  g  g   t  k  l  t   v  l  g (SEQ ID NO:54)
```

Fig. 7C

VL PROTEIN SEQUENCE

```
                     (SEQ ID NO:55)                      (SEQ ID NO:17)
  1 NFMLTQPHSV SESPGKTVTI SCTGSSGSIA SNYVQWYQQR PGSAPTTVIY EDNQRPSGVP
 61 DRFSGSIDSS SNSASLTISG LKTEDEADYY CQSYDSSNQE VVFGGGTKLT VLG (SEQ ID
NO:54)                                (SEQ ID NO:56)
```

Fig. 7D

VH NUCLEOTIDE SEQUENCE

```
  1  GAGGTGCAGC TGTTGGAGTC TGGGGGAGGC TTGGTACAGC CTGGGGGGTC CCTGAGACTC
        e  v  q   l  l  e   s  g  g   l  v  q   p  g  g   s  l  r  l
 61  TCCTGTGCAG CCTCTGGATT CACCTTTAGC AGCTATGCCA TGAGCTGGGT CCGCCAGGCT
        s  c  a   a  s  g   f  t  f   s  s  y   a  m  s   w  v  r  q  a
121  CCAGGGAAGG GGCTGGAGTG GGTCTCAGCT ATTAGTGGTA GTGGTGGTAG CACATACTAC
        p  g  k   g  l  e   w  v  s   a  i  s   g  s  g   g  s  t  y  y
181  GCAGACTCCG TGAAGGGCCG GTTCACCATC TCCAGAGACA ATTCCAAGAA CACGCTGTAT
        a  d  s   v  k  g   r  f  t   i  s  r   d  n  s   k  n  t  l  y
241  CTGCAAATGA ACAGCCTGAG AGCCGAGGAC ACGGCCGTAT ATTACTGTGC GAAAGATGGT
        l  q  m   n  s  l   r  a  e   d  t  a   v  y  y   c  a  k  d  g
301  AGCAGTGGCT GGTACGTACC ACACTGGTTC GACCCCTGGG GCCAGGGAAC CCTGGTCACC
        s  s  g   w  y  v   p  h  w   f  d  p   w  g  q   g  t  l  v  t
361  GTCTCGAGT (SEQ ID NO:57)
        v  s  s (SEQ ID NO:58)
```

Fig. 8A

VH PROTEIN SEQUENCE

```
                      (SEQ ID NO:3)           (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDG SSGWYVPHWF DPWGQGTLVT
121  VSS (SEQ ID NO:58)                           (SEQ ID NO:5)
```

Fig. 8B

VL NUCLEOTIDE SEQUENCE

```
  1  AATTTTATGC TGACTCAGCC CCACTCTGTG TCGGAGTCTC CGGGGAAGAC GGTTACCATC
        n  f  m   l  t  q   p  h  s   v  s  e   s  p  g   k  t  v  t  i
 61  TCCTGCACCC GCAGCAGTGG CAGCATTGTC AGCAACTATG TACAGTGGTA CCAGCAGCGC
        s  c  t   r  s  s   g  s  i   v  s  n   y  v  q   w  y  q  q  r
121  CCGGGCAGTT CCCCCACCAC TGTGATCTAT GAGGATAACC AAAGACCCTC TGGGGTCCCT
        p  g  s   s  p  t   t  v  i   y  e  d   n  q  r   p  s  g  v  p
181  GATCGGTTCT CTGGCTCCAT CGACAGCTCC TCCAACTCTG CCTCCCTCAC CATCTCTGGA
        d  r  f   s  g  s   i  d  s   s  s  n   s  a  s   l  t  i  s  g
241  CTGAAGACTG AGGACGAGGC TGACTACTAC TGTCAGTCTT ATGATAGCAA CAATTTTTGG
        l  k  t   e  d  e   a  d  y   y  c  q   s  y  d   s  n  n  f  w
301  GTGTTCGGCG GAGGGACCAA GCTGACCGTC CTAGGT (SEQ ID NO:59)
        v  f  g   g  g  t   k  l  t   v  l  g (SEQ ID NO:60)
```

Fig. 8C

VL PROTEIN SEQUENCE

```
                     (SEQ ID NO:8)                    (SEQ ID NO:17)
  1  NFMLTQPHSV SESPGKTVTI SCTRSSGSIV SNYVQWYQQR PGSSPTTVIY EDNQRPSGVP
 61  DRFSGSIDSS SNSASLTISG LKTEDEADYY CQSYDSNNFW VFGGGTKLTV LG (SEQ ID
NO:60)
                                           (SEQ ID NO:61)
```

Fig. 8D

VH NUCLEOTIDE SEQUENCE

```
  1 GAGGTGCAGC TGTTGGAGTC TGGGGGAGGC TTGGTACAGC CTGGGGGGTC CCTGAGACTC
     e  v  q   l  l  e   s  g  g   l  v  q   p  g  g   s  l  r  l
 61 TCCTGTGCAG CCTCTGGATT CACCTTTAGC AGCTATGCCA TGAGCTGGGT CCGCCAGGCT
     s  c  a   a  s  g   f  t  f   s  s  y  a  m  s  w  v  r  q  a
121 CCAGGGAAGG GGCTGGAGTG GGTCTCAGCT ATTAGTGGTA GTGGTGGTAG CACATACTAC
     p  g  k   g  l  e   w  v  s  a  i  s  g   s  g  g   s  t  y  y
181 GCAGACTCCG TGAAGGGCCG GTTCACCATC TCCAGAGACA ATTCCAAGAA CACGCTGTAT
     a  d  s   v  k  g   r  f  t  i   s  r  d   n  s  k   n  t  l  y
241 CTGCAAATGA ACAGCCTGAG AGCCGAGGAC ACGGCCGTGT ATTACTGTGT GAAAAGGTCC
     l  q  m   n  s  l   r  a  e  d   t  a  v   y  y  c  v  k  r  s
301 TTTGATAGTG GTGGGTCCTT TGAGTACTGG GGCCAGGGGA CAATGGTCAC
     f  d  s   g  g  s   f  e  y  w   g  q  g   t  m  v
351 CGTCTCGAGT (SEQ ID NO:62)
     t  v  s  s (SEQ ID NO:63)
```

Fig. 9A

VH PROTEIN SEQUENCE

```
                            (SEQ ID NO:3)        (SEQ ID NO:4)
 1 EVQLLESGGG LVQPGGSLRL SCAASGFTFS SYAMSWVRQA PGKGLEWVSA ISGSGGSTYY
61 ADSVKGRFTI SRDNSKNTLY LQMNSLRAED TAVYYCVKRS FDSGGSFEYW GQGTMVTVSS (SEQ
ID NO:63)                                     (SEQ ID NO:64)
```

Fig. 9B

VL NUCLEOTIDE SEQUENCE

```
  1 AATTTTATGC TGACTCAGCC CCACTCTGTG TCGGAGTCTC CGGGGAAGAC GGTCACCATC
     n  f  m   l  t  q   p  h  s  v   s  e  s   p  g  k   t  v  t  i
 61 TCCTGCACCC GCAGCAGTGG CTACATTGCC AGCTCCTATG TGCAGTGGTA CCAGCAGCGC
     s  c  t   r  s  s   g  y  i  a   s  s  y   v  q  w   y  q  q  r
121 CCGGGCAGTT CCCCCACCAC TGTAATCTTT GAGGATGACC GGAGACCCTC TGGGGTCCCT
     p  g  s   s  p  t   t  v  i  f   e  d  d   r  r  p   s  g  v  p
181 GATCGGTTCT CTGGCTCCAT CGACGGCTCC TCCAACTCTG CCTCCCTCAC CATCTCTGGA
     d  r  f   s  g  s   i  d  g  s   s  n  s  a  s  l   t  i  s  g
241 CTGAGGACTG AGGACGAGGC TGACTACTAC TGTCAGTCTT ATGATGACAC CACTCCCTGG
     l  r  t   e  d  e   a  d  y  y   c  q  s   y  d  d   t  t  p  w
301 GTGTTCGGCG GAGGGACCAA GCTGACCGTC CTAGGT (SEQ ID NO:65)
     v  f  g   g  g  t   k  l  t  v   l  g (SEQ ID NO:66)
```

Fig. 9C

VL PROTEIN SEQUENCE

```
                       (SEQ ID NO:8)                 (SEQ ID NO:25)
 1 NFMLTQPHSV SESPGKTVTI SCTRSSGYIA SSYVQWYQQR PGSSPTTVIF EDDRRPSGVP
61 DRFSGSIDGS SNSASLTISG LRTEDEADYY CQSYDDTTPW VFGGGTKLTV LG (SEQ ID NO:66)
                                   (SEQ ID NO:26)
```

Fig. 9D

VH NUCLEOTIDE SEQUENCE

```
  1  GAGGTGCAGC TGTTGGAGTC TGGGGGAGGC TTGGTACAGC CTGGGGGGTC CCTGAGACTC
        e  v  q   l  l  e   s  g  g   g  l  v   q  p  g   g  s  l  r  l
 61  TCCTGTGCAG CCTCTGGATT CACCTTTAGC AGCTATGCCA TGAGCTGGGT CCGCCAGGCT
        s  c  a   a  s  g   f  t  f   s  s  y   a  m  s   w  v  r  q  a
121  CCAGGGAAGG GGCTGGAGTG GGTCTCAGCT ATTAGTGGTA GTGGTGGTAG CACATACTAC
        p  g  k   g  l  e   w  v  s   a  i  s   g  s  g   g  s  t  y  y
181  GCAGACTCCG TGAAGGGCCG GTTCACCATC TCCAGAGACA ATTCCAAGAA CACGCTGTAT
        a  d  s   v  k  g   r  f  t   i  s  r   d  n  s   k  n  t  l  y
241  CTGCAAATGA ACAGCCTGAG AGCCGAGGAC ACGGCCGTGT ATTACTGTGC GAGAGTCGGC
        l  q  m   n  s  l   r  a  e   d  t  a   v  y  y   c  a  r  v  g
301  AGCTGGTACC TGGAAGATTT TGATATCTGG GGCCGGGGGA CAATGGTCAC
        s  w  y   l  e  d   f  d  i   w  g  r   g  t  m   v
351  CGTCTCGAGT (SEQ ID NO:67)
        t  v  s  s (SEQ ID NO:68)
```

Fig. 10A

VH PROTEIN SEQUENCE

```
                                    (SEQ ID NO:3)        (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCARVG SWYLEDFDIW GRGTMVTVSS (SEQ
ID NO:68)                                        (SEQ ID NO:69)
```

Fig. 10B

VL NUCLEOTIDE SEQUENCE

```
  1  AATTTTATGC TGACTCAGCC CCACTCTGTG TCGGAGTCTC CGGGGAAGAC GGTTACCATC
        n  f  m   l  t  q   p  h  s   v  s  e   s  p  g   k  t  v  t  i
 61  TCCTGCACCC GCAGCAGTGG CAGCATTGCC AGCAACTATG TTCACTGGTA TCAGCAGCGC
        s  c  t   r  s  s   g  s  i   a  s  n   y  v  h   w  y  q  q  r
121  CCGGGCAGTT CACCCACCAC TGTGATCTAT GAGGATAACC GAAGACCCTC TGGGGTCCCT
        p  g  s   s  p  t   t  v  i   y  e  d   n  r  r   p  s  g  v  p
181  GCTCGGTTCT CTGGCTCCAT CGACAGCTCC TCCAACTCTG CCTCCCTCAC CATCTCTGGA
        a  r  f   s  g  s   i  d  s   s  s  n   s  a  s   l  t  i  s  g
241  CTGGAGACTG ACGACGAGGC TGACTACTAC TGTCAGTCTT CTGATACCAC CTATCATGGA
        l  e  t   d  d  e   a  d  y   y  c  q   s  s  d   t  t  y  h  g
301  GGTGTGGTAT TCGGCGGAGG GACCAAGCTG ACCGTCCTAG GT (SEQ ID NO:70)
        g  v  v   f  g  g   g  t  k   l  t  v   l  g (SEQ ID NO:71)
```

Fig. 10C

VL PROTEIN SEQUENCE

```
                                    (SEQ ID NO:72)        (SEQ ID NO:9)
  1  NFMLTQPHSV SESPGKTVTI SCTRSSGSIA SNYVHWYQQR PGSSPTTVIY EDNRRPSGVP
 61  ARFSGSIDSS SNSASLTISG LETDDEADYY CQSSDTTYHG GVVFGGGTKL TVLG (SEQ ID NO:71)
                                      (SEQ ID NO:73)
```

Fig. 10D

VH NUCLEOTIDE SEQUENCE

```
  1  GAGGTGCAGC TGTTGGAGTC TGGGGGAGGC TTGGTACAGC CTGGGGGGTC CCTGAGACTC
        e  v  q   l  l  e   s  g  g    l  v  q   p  g  g    s  l  r  l
 61  TCCTGTGCAG CCTCTGGATT CACCTTTAGC AGCTATGCCA TGAGCTGGGT CCGCCAGGCT
      s  c  a   a  s  g   f  t  f  s  s  y  a   m  s  w    v  r  q  a
121  CCAGGGAAGG GGCTGGAGTG GGTCTCAGCT ATTAGTGGTA GTGGTGGTAG CACATACTAC
      p  g  k   g  l  e   w  v  s  a  i  s  g   s  g  g    s  t  y  y
181  GCAGACTCCG TGAAGGGCCG GTTCACCATC TCCAGAGACA ATTCCAAGAA CACGCTGTAT
      a  d  s   v  k  g   r  f  t  i  s  r  d   n  s  k    n  t  l  y
241  CTGCAAATGA ACAGCCTGAG AGCCGAGGAC ACGGCCGTGT ATTACTGTGC GAAAGGCGGT
      l  q  m   n  s  l   r  a  e  d  t  a  v   y  y  c    a  k  g  g
301  AACTACGGTG ATTACTTCGA CTACTTTGAC TACTGGGGCA GAGGGACAAT GGTCACCGTC
      n  y  g   d  y  f   d  y  f  d  y  w  g   r  g  t    m  v  t  v
361  TCGAGT (SEQ ID NO:74)
      s  s  (SEQ ID NO:75)
```

Fig. 11A

VH PROTEIN SEQUENCE

```
                               (SEQ ID NO:3)         (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKGG NYGDYFDYFD YWGRGTMVTV
121  SS (SEQ ID NO:75)                           (SEQ ID NO:76)
```

Fig. 11B

VL NUCLEOTIDE SEQUENCE

```
  1  AATTTTATGC TGACTCAGCC CCACTCTGTG TCGGAGTCTC CGGGGAAGAC GGTAACCATC
      n  f  m   l  t  q   p  h  s  v  s  e  s   p  g  k    t  v  t  i
 61  TCCTGCACCC GCAGCAGTGG CAGCATTGCC AGCAATTATG TGCAGTGGTA CCAGCAGCGC
      s  c  t   r  s  s   g  s  i  a  s  n  y   v  q  w    y  q  q  r
121  CCGGGCAGTG CCCCCACCAT TGTGATCTAT GAAGATAACC AAAGACCCTC TGGGGTCCCT
      p  g  s   a  p  t   i  v  i  y  e  d  n   q  r  p    s  g  v  p
181  CATCGGTTCT CTGGCTCCAT CGACAGCTCC TCCAACTCTG CCTCCCTCAC CATCTCTGGA
      h  r  f   s  g  s   i  d  s  s  s  n  s   a  s  l    t  i  s  g
241  CTGAAGACTG AGGACGAGGC TGACTACTAC TGTCAGTCTT ATGAGGGGTT CGGCGGAGGG
      l  k  t   e  d  e   a  d  y  y  c  q  s   y  e  g    f  g  g  g
301  ACCAAGCTGA CCGTCCTAGG T (SEQ ID NO:77)
      t  k  l   t  v  l   g (SEQ ID NO:78)
```

Fig. 11C

VL PROTEIN SEQUENCE

```
                  (SEQ ID NO:16)                  (SEQ ID NO:17)
  1  NFMLTQPHSV SESPGKTVTI SCTRSSGSIA SNYVQWYQQR PGSAPTIVIY EDNQRPSGVP
 61  HRFSGSIDSS SNSASLTISG LKTEDEADYY CQSYEGFGGG TKLTVLG (SEQ ID NO:78)
                                      (SEQ ID NO:79)
```

Fig. 11D

VH NUCLEOTIDE SEQUENCE

```
  1  GAGGTGCAGC TGTTGGAGTC TGGGGGAGGC TTGGTACAGC CTGGGGGGTC CCTGAGACTC
       e  v  q   l  l  e   s  g  g  g   l  v  q   p  g  g   s  l  r  l
 61  TCCTGTGCAG CCTCTGGATT CACCTTTAGC AGCTATGCCA TGAGCTGGGT CCGCCAGGCT
       s  c  a   a  s  g   f  t  f  s   s  y  a   m  s  w   v  r  q  a
121  CCAGGGAAGG GGCTGGAGTG GGTCTCAGCT ATTAGTGGTA GTGGTGGTAG CACATACTAC
       p  g  k   g  l  e   w  v  s  a   i  s  g   s  g  g   s  t  y  y
181  GCAGACTCCG TGAAGGGCCG GTTCACTATC TCCAGAGACA ATTCCAAGAA CACGCTGTAT
       a  d  s   v  k  g   r  f  t  i   s  r  d   n  s  k   n  t  l  y
241  CTGCAAATGA ACAGCCTGAG AGCCGAGGAC ACGGCCGTGT ATTACTGTGC GAAAGATGGA
       l  q  m   n  s  l   r  a  e  d   t  a  v   y  y  c   a  k  d  g
301  TGGAACGCGC TGGGATGGCT TGAATCCTGG GGCCAGGGGA CAATGGTCAC
       w  n  a   l  g  w   l  e  s  w   g  q  g   t  m  v
351  CGTCTCGAGT (SEQ ID NO:80)
       t  v  s  s (SEQ ID NO:81)
```

Fig. 12A

VH PROTEIN SEQUENCE (SEQ ID NO:3)      (SEQ ID NO:4)

1 EVQLLESGGG LVQPGGSLRL SCAASGFTFS SYAMSWVRQA PGKGLEWVSA ISGSGGSTYY
 61 ADSVKGRFTI SRDNSKNTLY LQMNSLRAED TAVYYCAKDG WNALGWLESW GQGTMVTVSS (SEQ
ID NO:81)                                 (SEQ ID NO:29)

Fig. 12B

VL NUCLEOTIDE SEQUENCE

```
  1  AATTTTATGC TGACTCAGCC CCACGCTGTG TCGGAGTCTC CGGGGAAGAC GGTGACCATT
       n  f  m   l  t  q   p  h  a  v   s  e  s   p  g  k   t  v  t  i
 61  TCCTGCACCG GCAGAAATGG CAACATTGCC AGCAACTATG TGCAGTGGTA CCAGCAGCGC
       s  c  t   g  r  n   g  n  i  a   s  n  y   v  q  w   y  q  q  r
121  CCGGACAGTG CCCCCACCCT TATAATCTTT GAAGATACCC AAAGACCCTC TGGGGTCCCT
       p  d  s   a  p  t   l  i  i  f   e  d  t   q  r  p   s  g  v  p
181  ACTCGGCTCT CAGGCTCCAT CGACACCTCC TCCAATTCTG CCTCCCTCAT CATCTCTTCA
       t  r  l   s  g  s   i  d  t  s   s  n  s   a  s  l   i  i  s  s
241  TTGAGGACTG AGGACGAGGC TGATTACTAC TGTCAATCTT CTGATTCCAA CAGGGTGCTG
       l  r  t   e  d  e   a  d  y  y   c  q  s   s  d  s   n  r  v  l
301  TTCGGCGGAG GGACCAAGGT CACCGTCCTA GGT (SEQ ID NO:82)
       f  g  g   g  t  k   v  t  v  l   g (SEQ ID NO:83)
```

Fig. 12C

VL PROTEIN SEQUENCE (SEQ ID NO:84)          (SEQ ID NO:85)

1 NFMLTQPHAV SESPGKTVTI SCTGRNGNIA SNYVQWYQQR PDSAPTLIIF EDTQRPSGVP
 61 TRLSGSIDTS SNSASLIISS LRTEDEADYY CQSSDSNRVL FGGGTKVTVL G (SEQ ID NO:83)
                                           (SEQ ID NO:86)

Fig. 12D

VH NUCLEOTIDE SEQUENCE

```
  1  GAGGTGCAGC TGTTGGAGTC TGGGGGAGGC TTGGTACAGC CTGGGGGGTC CCTGAGACTC
      e  v  q   l  l  e   s  g  g   l  v  q   p  g  g   s  l  r  l
 61  TCCTGTGCAG CCTCTGGATT CACCTTTAGC AGCTATGCCA TGAGCTGGGT CCGCCAGGCT
      s  c  a   a  s  g   f  t  f   s  s  y   a  m  s   w  v  r  q  a
121  CCAGGGAAGG GGCTGGAGTG GGTCTCAGCT ATTAGTGGTA GTGGTGGTAG CACATACTAC
      p  g  k   g  l  e   w  v  s   a  i  s   g  s  g   g  s  t  y  y
181  GCAGACTCCG TGAAGGGCCG GTTCACCATC TCCAGAGACA ATTCCAAGAA CACGCTGTAT
      a  d  s   v  k  g   r  f  t   i  s  r   d  n  s   k  n  t  l  y
241  CTGCAAATGA ACAGCCTGAG AGCCGAGGAC ACGGCCGTGT ATTACTGTGC GAAAGATTTT
      l  q  m   n  s  l   r  a  e   d  t  a   v  y  y   c  a  k  d  f
301  TGGGTTATTA CGAGTGGGAA TGACTACTGG GGGCGGGGGA CCACGGTCAC
      w  v  i   t  s  g   n  d  y   w  g  r   g  t  t   v
351  CGTCTCGAGT (SEQ ID NO:87)
      t  v  s  s (SEQ ID NO:88)
```

Fig. 13A

VH PROTEIN SEQUENCE

```
                       (SEQ ID NO:3)          (SEQ ID NO:4)
  1  EVQLLESGGG LVQPGGSLRL SCAASGFTFS SYAMSWVRQA PGKGLEWVSA ISGSGGSTYY
 61  ADSVKGRFTI SRDNSKNTLY LQMNSLRAED TAVYYCAKDF WVITSGNDYW GRGTTVTVSS
     (SEQ ID NO:88)                            (SEQ ID NO:89)
```

Fig. 13B

VL NUCLEOTIDE SEQUENCE

```
  1  AATTTTATGC TGACTCAGCC CCACTCTGTG TCGGAGTCTC CGGGGAAGAC GGTGACCATC
      n  f  m   l  t  q   p  h  s   v  s  e   s  p  g   k  t  v  t  i
 61  TCCTGCACCC GCAGCAGTGG CAGCATTGCT AGCAATTATG TGCAGTGGTA CCAGCAGCGC
      s  c  t   r  s  s   g  s  i   a  s  n   y  v  q   w  y  q  q  r
121  CCGGGCAGTT CCCCCACCAC TGTGATCTTT GAAGATAACC GAAGACCCTC TGGGGTCCCT
      p  g  s   s  p  t   t  v  i  f   e  d  n   r  r  p   s  g  v  p
181  GATCGGTTTT CTGGCTCCAT CGACACCTCC TCCAACTCTG CCTCCCTCAC CATCTCTGGA
      d  r  f   s  g  s   i  d  t   s  s  n   s  a  s   l  t  i  s  g
241  CTGAAGACTG AGGACGAGGC TGACTACTAC TGTCAGTCTT TTGATAGCAC CAATCTTGTG
      l  k  t   e  d  e   a  d  y   y  c  q   s  f  d   s  t  n  l  v
301  GTGTTCGGCG GAGGGACCAA GCTGACCGTC CTAGGT (SEQ ID NO:90)
      v  f  g   g  g  t   k  l  t   v  l  g (SEQ ID NO:91)
```

Fig. 13C

VL PROTEIN SEQUENCE

```
                      (SEQ ID NO:16)             (SEQ ID NO:9)
  1  NFMLTQPHSV SESPGKTVTI SCTRSSGSIA SNYVQWYQQR PGSSPTTVIF EDNRRPSGVP
 61  DRFSGSIDTS SNSASLTISG LKTEDEADYY CQSFDSTNLV VFGGGTKLTV LG (SEQ ID NO:91)
                                      (SEQ ID NO:92)
```

Fig. 13D

VH NUCLEOTIDE SEQUENCE

```
  1 GAGGTGCAGC TGTTGGAGTC TGGGGGAGGC TTGGTACAGC CTGGGGGGTC CCTGAGACTC
     e  v  q   l  l  e    s  g  g   l  v  q    p  g  g    s  l  r  l
 61 TCCTGTGCAG CCTCTGGATT CACCTTTAGC AGCTATGCCA TGAGCTGGGT CCGCCAGGCT
     s  c  a   a  s  g    f  t  f   s  y  a    m  s  w    v  r  q  a
121 CCAGGGAAGG GGCTGGAGTG GGTCTCAGCT ATTAGTGGTA GTGGTGGTAG CACATACTAC
     p  g  k   g  l  e    w  v  s   a  i  s    g  s  g    g  s  t  y  y
181 GCAGACTCCG TGAAGGGCCG GTTCACCATC TCCAGAGACA ATTCCAAGAA CACGCTGTAT
     a  d  s   v  k  g    r  f  t   i  s  r    d  n  s    k  n  t  l  y
241 CTGCAAATGA ACAGCCTGAG AGCCGAGGAC ACGGCCGTGT ATTACTGTGC GAAAGATGGA
     l  q  m   n  s  l    r  a  e   d  t  a    v  y  y    c  a  k  d  g
301 TGGAACGCGC TGGGATGGCT TGAATCCTGG GGAAGGGGA CCACGGTCAC
     w  n  a   l  g  w    l  e  s   w  g  k    g  t  t    v
351 CGTCTCGAGT (SEQ ID NO:93)
     t  v  s  s (SEQ ID NO:94)
```

Fig. 14A

VH PROTEIN SEQUENCE

```
                         (SEQ ID NO:3)         (SEQ ID NO:4)
  1 EVQLLESGGG LVQPGGSLRL SCAASGFTFS SYAMSWVRQA PGKGLEWVSA ISGSGGSTYY
 61 ADSVKGRFTI SRDNSKNTLY LQMNSLRAED TAVYYCAKDG WNALGWLESW GKGTTVTVSS (SEQ
ID NO:94)                                       (SEQ ID NO:29)
```

Fig. 14B

VL NUCLEOTIDE SEQUENCE

```
  1 AATTTTATGC TGACTCAGCC CCACTCTGTG TCGGAGTCTC CGGGGAAGAC GGTAACCATC
     n  f  m   l  t  q    p  h  s   v  s  e    s  p  g    k  t  v  t  i
 61 TCCTGCGCCG GCAGCAGTGG CAGCATTGCC AGCAACTATG TGCAGTGGTA CCAGCAGCGC
     s  c  a   g  s  s    g  s  i   a  s  n    y  v  q    w  y  q  q  r
121 CCGGGCAGTG CCCCCACCGC TGTGATCTAT GAGGATAACC AAAGACCCTC TGGGGTCCCT
     p  g  s   a  p  t    a  v  i   y  e  d    n  q  r    p  s  g  v  p
181 GATCGATTCT CTGGCTCCAT CGACAGCTCC TCCAACTCTG CCTCCCTCAC CATCTCTGGA
     d  r  f   s  g  s    i  d  s   s  s  n    s  a  s    l  t  i  s  g
241 CTGAAGACTG AGGACGAGGC TGACTACTAC TGTCAATCTT ACTCTTACAA CAATCAGGTC
     l  k  t   e  d  e    a  d  y   y  c  q    s  y  s    y  n  n  q  v
301 GTGTTCGGCG AGGGGACCAA GGTCACCGTC CTAGGT (SEQ ID NO:95)
     v  f  g   g  g  t    k  v  t   v  l  g  (SEQ ID NO:96)
```

Fig. 14C

VL PROTEIN SEQUENCE

```
                        (SEQ ID NO:97)         (SEQ ID NO:17)
  1 NFMLTQPHSV SESPGKTVTI SCAGSSGSIA SNYVQWYQQR PGSAPTAVIY EDNQRPSGVP
 61 DRFSGSIDSS SNSASLTISG LKTEDEADYY CQSYSYNNQV VFGGGTKVTV LG (SEQ ID NO:96)
                                    (SEQ ID NO:98)
```

Fig. 14D

SEQUENCE LISTING

```
<160> NUMBER OF SEQ ID NOS: 118

<210> SEQ ID NO 1
<211> LENGTH: 369
<212> TYPE: DNA
<213> ORGANISM: Homo sapiens

<400> SEQUENCE: 1
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatggt    300
agcagtggct ggtacgtacc acactggttc gacccctggg gccagggcac cctggtcacc    360
gtctcctca                                                            369

<210> SEQ ID NO 2
<211> LENGTH: 123
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
            100                 105                 110

Trp Gly Gln Gly Thr Leu Val Thr Val Ser Ser
        115                 120

<210> SEQ ID NO 3
<211> LENGTH: 5
```

```
<212> TYPE: PRT
<213> ORGANISM: Homo sapiens

<400> SEQUENCE: 3

Ser Tyr Ala Met Ser
1               5

<210> SEQ ID NO 4
<211> LENGTH: 17
<212> TYPE: PRT
<213> ORGANISM: Homo sapiens

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 14
<212> TYPE: PRT
<213> ORGANISM: Homo sapiens

<400> SEQUENCE: 5

Asp Gly Ser Ser Gly Trp Tyr Val Pro His Trp Phe Asp Pro
1               5                   10

<210> SEQ ID NO 6
<211> LENGTH: 333
<212> TYPE: DNA
<213> ORGANISM: Homo sapiens

<400> SEQUENCE: 6
aattttatgc tgactcagcc ccactctgtg tcggagtctc cggggaagac ggtaaccatc      60
tcctgcactc gcagcagtgg cagcattgcc agcaactatg tgcagtggta ccaacagcgc     120
ccgggcagtt cccccaccac tgtcatctat gaggataacc agagaccctc tggggtccct     180
gatcggttct ctggctccat cgacagctcc tccaattctg cctccctcac catctctggg     240
ctgaagactg aggacgaggc tgactactac tgtcagtctt atgatggcag caatcgttgg     300
atgttcggcg gagggaccaa gctgaccgtc cta                                  333

<210> SEQ ID NO 7
<211> LENGTH: 111
<212> TYPE: PRT
<213> ORGANISM: Homo sapiens

<400> SEQUENCE: 7

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Ser Asn Arg Trp Met Phe Gly Gly Gly Thr Lys Leu Thr Val Leu
```

<210> SEQ ID NO 8
<211> LENGTH: 13
<212> TYPE: PRT
<213> ORGANISM: Homo sapiens

<400> SEQUENCE: 8

Thr Arg Ser Ser Gly Ser Ile Ala Ser Asn Tyr Val Gln
1               5                   10

<210> SEQ ID NO 9
<211> LENGTH: 7
<212> TYPE: PRT
<213> ORGANISM: Homo sapiens

<400> SEQUENCE: 9

Glu Asp Asn Gln Arg Pro Ser
1               5

<210> SEQ ID NO 10
<211> LENGTH: 10
<212> TYPE: PRT
<213> ORGANISM: Homo sapiens

<400> SEQUENCE: 10

Gln Ser Tyr Asp Gly Ser Asn Arg Trp Met
1               5                   10

<210> SEQ ID NO 11
<211> LENGTH: 369
<212> TYPE: DNA
<213> ORGANISM: Homo sapiens

<400> SEQUENCE: 11

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatcat    300
agcagtggct ggtacgtaat ctccggtatg gacgtctggg gccagggac aatggtcacc    360
gtctcgagt                                                             369
```

<210> SEQ ID NO 12
<211> LENGTH: 123
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Asp His Ser Ser Gly Trp Tyr Val Ile Ser Gly Met Asp Val
            100                 105                 110

Trp Gly Arg Gly Thr Met Val Thr Val Ser Ser
        115                 120
```

<210> SEQ ID NO 13
<211> LENGTH: 14
<212> TYPE: PRT
<213> ORGANISM: Homo sapiens

<400> SEQUENCE: 13

```
Asp His Ser Ser Gly Trp Tyr Val Ile Ser Gly Met Asp Val
1               5                   10
```

<210> SEQ ID NO 14
<211> LENGTH: 333
<212> TYPE: DNA
<213> ORGANISM: Homo sapiens

<400> SEQUENCE: 14

```
aattttatgc tgactcagcc ccactctgtg tcggagtctc cggggaagac ggtaaccatc     60
tcctgcaccc gcagcagtgg cagcattgcc agcaactatg tgcagtggta ccagcagcgc    120
ccgggcagtt cccccaccac tgtgatctct gaggataacc aaagaccctc tggggtccct    180
gatcggttct ctggctccgt cgacagctcc tccaactctg cctccctcac catttctgga    240
ctgaggactg aggacgaggc tgactattac tgtcagtcta atgattccga caatgtggtt    300
ttcggcggag ggaccaagct gaccgtccta ggt                                 333
```

<210> SEQ ID NO 15
<211> LENGTH: 111
<212> TYPE: PRT
<213> ORGANISM: Homo sapiens

<400> SEQUENCE: 15

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Ser Glu Asp Asn Gln Arg Pro Ser Gly Val Pro Asp Arg Phe Ser
    50                  55                  60

Gly Ser Val Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Asn Asp Ser
                85                  90                  95

Asp Asn Val Val Phe Gly Gly Gly Thr Lys Leu Thr Val Leu Gly
            100                 105                 110
```

<210> SEQ ID NO 16
<211> LENGTH: 13
<212> TYPE: PRT
<213> ORGANISM: Homo sapiens

<400> SEQUENCE: 16

```
Thr Arg Ser Ser Gly Ser Ile Ala Ser Asn Tyr Val Gln
```

<210> SEQ ID NO 17
<211> LENGTH: 7
<212> TYPE: PRT
<213> ORGANISM: Homo sapiens

<400> SEQUENCE: 17

Glu Asp Asn Gln Arg Pro Ser
1               5

<210> SEQ ID NO 18
<211> LENGTH: 9
<212> TYPE: PRT
<213> ORGANISM: Homo sapiens

<400> SEQUENCE: 18

Gln Ser Asn Asp Ser Asp Asn Val Val
1               5

<210> SEQ ID NO 19
<211> LENGTH: 366
<212> TYPE: DNA
<213> ORGANISM: Homo sapiens

<400> SEQUENCE: 19
gaggtgcagc tgttggagtc tgggggaggc ttggtacagc ctggggggtc cctgagactc      60
tcctgtgcag cctctggatt caccttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca atcccaagaa cacgctgtat    240
ctgcaaatga acagcctgag agccgaggac acggccgtgt attactgtgc gaaggaccta    300
acagtgggtg gtccctggta ctactttgac tactggggcc aaggaaccct ggtcaccgtc    360
tcgagt                                                                366

<210> SEQ ID NO 20
<211> LENGTH: 122
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Thr Val Gly Gly Pro Trp Tyr Tyr Phe Asp Tyr Trp
            100                 105                 110

Gly Gln Gly Thr Leu Val Thr Val Ser Ser
        115                 120

<210> SEQ ID NO 21
<211> LENGTH: 13
<212> TYPE: PRT
<213> ORGANISM: Homo sapiens

<400> SEQUENCE: 21

Asp Leu Thr Val Gly Gly Pro Trp Tyr Tyr Phe Asp Tyr
1               5                   10

<210> SEQ ID NO 22
<211> LENGTH: 333
<212> TYPE: DNA
<213> ORGANISM: Homo sapiens

<400> SEQUENCE: 22
aattttatgc tgactcagcc ccactctgtg tcggagtctc cggggaagac ggtaaccatc      60
tcctgcaccc gcagcagtgg cagcattgtc agcaactatg tgcagtggta ccagcagcgc     120
ccgggcagtg cccccaccac tgtgatcttt gacgatgacc aaagaccctc tggggtccct     180
ggtcggttct ctggctccct cgacagctcc tccaactctg cctccctcac catctctggg     240
ctgcagactg aggacgaggc tgactactac tgtcagtctt atgatagcag caatgtggta     300
ttcggcgggg ggaccaaggt caccgtccta ggt                                  333

<210> SEQ ID NO 23
<211> LENGTH: 111
<212> TYPE: PRT
<213> ORGANISM: Homo sapiens

<400> SEQUENCE: 23

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ala Pro Thr Thr Val
        35                  40                  45

Ile Phe Asp Asp Asp Gln Arg Pro Ser Gly Val Pro Gly Arg Phe Ser
    50                  55                  60

Gly Ser Leu Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ser Asn Val Val Phe Gly Gly Gly Thr Lys Val Thr Val Leu Gly
            100                 105                 110

<210> SEQ ID NO 24
<211> LENGTH: 60
<212> TYPE: PRT
<213> ORGANISM: Homo sapiens

<400> SEQUENCE: 24

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro
    50                  55                  60

<210> SEQ ID NO 25
<211> LENGTH: 7
<212> TYPE: PRT
<213> ORGANISM: Homo sapiens

<400> SEQUENCE: 25

Asp Asp Asp Gln Arg Pro Ser
1               5

<210> SEQ ID NO 26
<211> LENGTH: 9
<212> TYPE: PRT
<213> ORGANISM: Homo sapiens

<400> SEQUENCE: 26

Gln Ser Tyr Asp Ser Ser Asn Val Val
1               5

<210> SEQ ID NO 27
<211> LENGTH: 360
<212> TYPE: DNA
<213> ORGANISM: Homo sapiens

<400> SEQUENCE: 27
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaagatgga     300
tggaacgcgc tggatggct tgaatcctgg ggccggggca ccctggtcac cgtctcgagt     360

<210> SEQ ID NO 28
<211> LENGTH: 120
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Arg
            100                 105                 110

Gly Thr Leu Val Thr Val Ser Ser
        115                 120

<210> SEQ ID NO 29
<211> LENGTH: 11
<212> TYPE: PRT
<213> ORGANISM: Homo sapiens

<400> SEQUENCE: 29

Asp Gly Trp Asn Ala Leu Gly Trp Leu Glu Ser
1               5                   10

<210> SEQ ID NO 30
<211> LENGTH: 336
<212> TYPE: DNA
<213> ORGANISM: Homo sapiens

<400> SEQUENCE: 30

```
aattttatgc tgactcagcc ccactctgtg tcggagtctc cggggaggac gataaccatc    60
tcctgcaccc gcagtggtgg cagcattggc agctactatg tgcagtggta ccagcagcgc   120
ccgggcactg cccccaccac tgtgatctat gacgataaaa aaagaccctc tggggtccct   180
gatcggttct ctggctccat cgacagctcc tccaactctg cctccctcac catctctgga   240
ctgaagactg aggacgaggc tgactactat tgtcagtctt atgatagcaa caatcttgtg   300
gttttcggcg agggaccaa ggtcaccgtc ctaggt                              336
```

<210> SEQ ID NO 31
<211> LENGTH: 112
<212> TYPE: PRT
<213> ORGANISM: Homo sapiens

<400> SEQUENCE: 31

Asn Phe Met Leu Thr Gln Pro His Ser Val Ser Glu Ser Pro Gly Arg
1               5                   10                  15

Thr Ile Thr Ile Ser Cys Thr Arg Ser Gly Gly Ser Ile Gly Ser Tyr
            20                  25                  30

Tyr Val Gln Trp Tyr Gln Gln Arg Pro Gly Thr Ala Pro Thr Thr Val
        35                  40                  45

Ile Tyr Asp Asp Lys Lys Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Val Thr Val Leu Gly
            100                 105                 110

<210> SEQ ID NO 32
<211> LENGTH: 13
<212> TYPE: PRT
<213> ORGANISM: Homo sapiens

<400> SEQUENCE: 32

Thr Arg Ser Gly Gly Ser Ile Gly Ser Tyr Tyr Val Gln
1               5                   10

<210> SEQ ID NO 33
<211> LENGTH: 7
<212> TYPE: PRT
<213> ORGANISM: Homo sapiens

<400> SEQUENCE: 33

Asp Asp Lys Lys Arg Pro Ser
1               5

<210> SEQ ID NO 34

<211> LENGTH: 10
<212> TYPE: PRT
<213> ORGANISM: Homo sapiens

<400> SEQUENCE: 34

Gln Ser Tyr Asp Ser Asn Asn Leu Val Val
1               5                   10

<210> SEQ ID NO 35
<211> LENGTH: 369
<212> TYPE: DNA
<213> ORGANISM: Homo sapiens

<400> SEQUENCE: 35

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatggt     300
agcagtggct ggtacgtacc acactggttc gaccccctggg gcaggggac aatggtcacc     360 gtctcgagt                                                             369
```

<210> SEQ ID NO 36
<211> LENGTH: 123
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
            100                 105                 110

Trp Gly Arg Gly Thr Met Val Thr Val Ser Ser
        115                 120

<210> SEQ ID NO 37
<211> LENGTH: 336
<212> TYPE: DNA
<213> ORGANISM: Homo sapiens

<400> SEQUENCE: 37

```
aattttatgc tgactcagcc ccactctgtg tcggagtctc cggggaagac ggtaaccatc      60
tcctgcaccc gcagcagtgg caccattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
```

```
ctgaagactg aggacgaggc tgactactac tgtcagtctt atgataacag caatcattgg    300
gtgttcggcg agggaccaa ggtcaccgtc ctaggt                               336
```

<210> SEQ ID NO 38
<211> LENGTH: 112
<212> TYPE: PRT
<213> ORGANISM: Homo sapiens

<400> SEQUENCE: 38

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Thr Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asn
                85                  90                  95

Ser Asn His Trp Val Phe Gly Gly Gly Thr Lys Val Thr Val Leu Gly
            100                 105                 110
```

<210> SEQ ID NO 39
<211> LENGTH: 13
<212> TYPE: PRT
<213> ORGANISM: Homo sapiens

<400> SEQUENCE: 39

```
Thr Arg Ser Ser Gly Thr Ile Ala Ser Asn Tyr Val Gln
1               5                   10
```

<210> SEQ ID NO 40
<211> LENGTH: 10
<212> TYPE: PRT
<213> ORGANISM: Homo sapiens

<400> SEQUENCE: 40

```
Gln Ser Tyr Asp Asn Ser Asn His Trp Val
1               5                   10
```

<210> SEQ ID NO 41
<211> LENGTH: 360
<212> TYPE: DNA
<213> ORGANISM: Homo sapiens

<400> SEQUENCE: 41

```
gaggtgcagc tgttggagtc tgggggaggc ttggtacagc caggggggtc cctgaaactc    60
tcctgtgcag cctctggatt cacctttagc agcaatgcca tgagttgggt ccgccaggct   120
ccagggaagg ggctggagtg gtctcaact cttactggta gtggtggtac cgcatactac    180
gcagactccg tgagggccg gttcagcatc tccagagaca attccaagaa cacactgtat    240
ctgcaaatga acagcctgag agccgaggac acggccgtat attactgtgc gaagggcacg    300
gaactcgtgg gaggaggact tgacaactgg ggccaaggca ccctggtcac cgtctcgagt    360
```

<210> SEQ ID NO 42
<211> LENGTH: 120
<212> TYPE: PRT

<213> ORGANISM: Homo sapiens

<400> SEQUENCE: 42

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Ala | Ser | Gly | Phe | Thr | Phe | Ser | Ser | Asn |
|---|---|---|---|---|---|---|---|---|---|---|---|---|---|---|---|
| | | 20 | | | | | 25 | | | | | 30 | | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Thr | Leu | Thr | Gly | Ser | Gly | Gly | Thr | Ala | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Glu | Gly | Arg | Phe | Ser | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Gly | Thr | Glu | Leu | Val | Gly | Gly | Gly | Leu | Asp | Asn | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

<210> SEQ ID NO 43
<211> LENGTH: 5
<212> TYPE: PRT
<213> ORGANISM: Homo sapiens

<400> SEQUENCE: 43

| Ser | Asn | Ala | Met | Ser |
|---|---|---|---|---|
| 1 | | | | 5 |

<210> SEQ ID NO 44
<211> LENGTH: 17
<212> TYPE: PRT
<213> ORGANISM: Homo sapiens

<400> SEQUENCE: 44

| Thr | Leu | Thr | Gly | Ser | Gly | Gly | Thr | Ala | Tyr | Tyr | Ala | Asp | Ser | Val | Glu |
|---|---|---|---|---|---|---|---|---|---|---|---|---|---|---|---|
| 1 | | | | 5 | | | | | 10 | | | | | 15 | |

| Gly |
|---|
| |

<210> SEQ ID NO 45
<211> LENGTH: 11
<212> TYPE: PRT
<213> ORGANISM: Homo sapiens

<400> SEQUENCE: 45

| Gly | Thr | Glu | Leu | Val | Gly | Gly | Gly | Leu | Asp | Asn |
|---|---|---|---|---|---|---|---|---|---|---|
| 1 | | | | 5 | | | | | 10 | |

<210> SEQ ID NO 46
<211> LENGTH: 339
<212> TYPE: DNA
<213> ORGANISM: Homo sapiens

<400> SEQUENCE: 46

```
aattttatgc tgactcagcc ccactctctg tcggagtctc cggggaagac ggtgacgatc      60
tcctgcaccg gcagcggagg cagcattgcc accaactatg tgcagtggta tcagcagcgc     120
ccgggcagtg cccccaccac tgtgatccat gaggataacc aaagaccctc tggggtccct     180
gatcggttct ctggctccat cgacggctcc tccaactctg cctccctcac catctctgga     240
```

```
ctgcagcctg aggacgaggc tgattactac tgtcagtctt atgatagtga caatcatcat    300
gtggtattcg gcggagggac caagctgacc gtcctaggt                          339
```

<210> SEQ ID NO 47
<211> LENGTH: 113
<212> TYPE: PRT
<213> ORGANISM: Homo sapiens

<400> SEQUENCE: 47

```
Asn Phe Met Leu Thr Gln Pro His Ser Leu Ser Glu Ser Pro Gly Lys
1               5                   10                  15

Thr Val Thr Ile Ser Cys Thr Gly Ser Gly Gly Ser Ile Ala Thr Asn
            20                  25                  30

Tyr Val Gln Trp Tyr Gln Gln Arg Pro Gly Ser Ala Pro Thr Thr Val
        35                  40                  45

Ile His Glu Asp Asn Gln Arg Pro Ser Gly Val Pro Asp Arg Phe Ser
    50                  55                  60

Gly Ser Ile Asp Gly Ser Ser Asn Ser Ala Ser Leu Thr Ile Ser Gly
65                  70                  75                  80

Leu Gln Pro Glu Asp Glu Ala Asp Tyr Tyr Cys Gln Ser Tyr Asp Ser
                85                  90                  95

Asp Asn His His Val Val Phe Gly Gly Gly Thr Lys Leu Thr Val Leu
            100                 105                 110

Gly
```

<210> SEQ ID NO 48
<211> LENGTH: 13
<212> TYPE: PRT
<213> ORGANISM: Homo sapiens

<400> SEQUENCE: 48

```
Thr Gly Ser Gly Gly Ser Ile Ala Thr Asn Tyr Val Gln
1               5                   10
```

<210> SEQ ID NO 49
<211> LENGTH: 11
<212> TYPE: PRT
<213> ORGANISM: Homo sapiens

<400> SEQUENCE: 49

```
Gln Ser Tyr Asp Ser Asp Asn His His Val Val
1               5                   10
```

<210> SEQ ID NO 50
<211> LENGTH: 360
<212> TYPE: DNA
<213> ORGANISM: Homo sapiens

<400> SEQUENCE: 50

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaagatgga   300
tggaacgcgc tgggatggct tgaatcctgg ggcaagggga caatggtcac cgtctcgagt   360
```

<210> SEQ ID NO 51

```
<211> LENGTH: 120
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Lys
            100                 105                 110

Gly Thr Met Val Thr Val Ser Ser
        115                 120

<210> SEQ ID NO 52
<211> LENGTH: 60
<212> TYPE: PRT
<213> ORGANISM: Homo sapiens

<400> SEQUENCE: 52

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Arg Arg Pro Ser Gly Val Pro
    50                  55                  60

<210> SEQ ID NO 53
<211> LENGTH: 339
<212> TYPE: DNA
<213> ORGANISM: Homo sapiens

<400> SEQUENCE: 53
aattttatgc tgactcagcc ccactctgtg tcggagtctc cggggaagac ggtaaccatc      60
tcctgcaccg gcagcagtgg cagcattgcc agcaactatg tgcagtggta ccagcagcgc     120
ccgggcagtg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatcaagag     300
gtggtattcg gcggagggac caagctgacc gtcctaggt                           339

<210> SEQ ID NO 54
<211> LENGTH: 113
<212> TYPE: PRT
<213> ORGANISM: Homo sapiens

<400> SEQUENCE: 54

Asn Phe Met Leu Thr Gln Pro His Ser Val Ser Glu Ser Pro Gly Lys
```

```
1               5                   10                  15
Thr Val Thr Ile Ser Cys Thr Gly Ser Ser Gly Ser Ile Ala Ser Asn
            20                  25                  30
Tyr Val Gln Trp Tyr Gln Gln Arg Pro Gly Ser Ala Pro Thr Thr Val
            35                  40                  45
Ile Tyr Glu Asp Asn Gln Arg Pro Ser Gly Val Pro Asp Arg Phe Ser
    50                  55                  60
Gly Ser Ile Asp Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Asp Ser
                85                  90                  95
Ser Asn Gln Glu Val Val Phe Gly Gly Gly Thr Lys Leu Thr Val Leu
            100                 105                 110
Gly

<210> SEQ ID NO 55
<211> LENGTH: 13
<212> TYPE: PRT
<213> ORGANISM: Homo sapiens

<400> SEQUENCE: 55

Thr Gly Ser Ser Gly Ser Ile Ala Ser Asn Tyr Val Gln
1               5                   10

<210> SEQ ID NO 56
<211> LENGTH: 11
<212> TYPE: PRT
<213> ORGANISM: Homo sapiens

<400> SEQUENCE: 56

Gln Ser Tyr Asp Ser Ser Asn Gln Glu Val Val
1               5                   10

<210> SEQ ID NO 57
<211> LENGTH: 369
<212> TYPE: DNA
<213> ORGANISM: Homo sapiens

<400> SEQUENCE: 57
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatggt    300
agcagtggct ggtacgtacc acactggttc gaccccctggg gccagggaac cctggtcacc    360
gtctcgagt                                                            369

<210> SEQ ID NO 58
<211> LENGTH: 123
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Gly Ser Ser Gly Trp Tyr Val Pro His Trp Phe Asp Pro
            100                 105                 110
Trp Gly Gln Gly Thr Leu Val Thr Val Ser Ser
        115                 120
```

```
<210> SEQ ID NO 59
<211> LENGTH: 336
<212> TYPE: DNA
<213> ORGANISM: Homo sapiens

<400> SEQUENCE: 59
aattttatgc tgactcagcc ccactctgtg tcggagtctc cggggaagac ggttaccatc      60
tcctgcaccc gcagcagtgg cagcattgtc agcaactatg tacagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatagcaa caattttggg    300
gtgttcggcg gagggaccaa gctgaccgtc ctaggt                              336
```

```
<210> SEQ ID NO 60
<211> LENGTH: 112
<212> TYPE: PRT
<213> ORGANISM: Homo sapiens

<400> SEQUENCE: 60

Asn Phe Met Leu Thr Gln Pro His Ser Val Ser Glu Ser Pro Gly Lys
  1               5                  10                  15
Thr Val Thr Ile Ser Cys Thr Arg Ser Ser Gly Ser Ile Val Ser Asn
                 20                  25                  30
Tyr Val Gln Trp Tyr Gln Gln Arg Pro Gly Ser Ser Pro Thr Thr Val
             35                  40                  45
Ile Tyr Glu Asp Asn Gln Arg Pro Ser Gly Val Pro Asp Arg Phe Ser
 50                  55                  60
Gly Ser Ile Asp Ser Ser Ser Asn Ser Ala Ser Leu Thr Ile Ser Gly
 65                  70                  75                  80
Leu Lys Thr Glu Asp Glu Ala Asp Tyr Tyr Cys Gln Ser Tyr Asp Ser
                 85                  90                  95
Asn Asn Phe Trp Val Phe Gly Gly Gly Thr Lys Leu Thr Val Leu Gly
            100                 105                 110
```

```
<210> SEQ ID NO 61
<211> LENGTH: 10
<212> TYPE: PRT
<213> ORGANISM: Homo sapiens

<400> SEQUENCE: 61

Gln Ser Tyr Asp Ser Asn Asn Phe Trp Val
  1               5                  10
```

<210> SEQ ID NO 62
<211> LENGTH: 360
<212> TYPE: DNA
<213> ORGANISM: Homo sapiens

<400> SEQUENCE: 62

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgt gaaaggtcc     300 tttgatagtg gtgggtcctt tgagtactgg ggccagggga caatggtcac cgtctcgagt    360
```

<210> SEQ ID NO 63
<211> LENGTH: 120
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Arg Ser Phe Asp Ser Gly Gly Ser Phe Glu Tyr Trp Gly Gln
            100                 105                 110

Gly Thr Met Val Thr Val Ser Ser
        115                 120

<210> SEQ ID NO 64
<211> LENGTH: 11
<212> TYPE: PRT
<213> ORGANISM: Homo sapiens

<400> SEQUENCE: 64

Arg Ser Phe Asp Ser Gly Gly Ser Phe Glu Tyr
1               5                   10

<210> SEQ ID NO 65
<211> LENGTH: 336
<212> TYPE: DNA
<213> ORGANISM: Homo sapiens

<400> SEQUENCE: 65

```
aattttatgc tgactcagcc ccactctgtg tcggagtctc cggggaagac ggtcaccatc      60
tcctgcaccc gcagcagtgg ctacattgcc agctcctatg tgcagtggta ccagcagcgc    120
ccgggcagtt cccccaccac tgtaatcttt gaggatgacc ggagaccctc tggggtccct    180
gatcggttct ctggctccat cgacggctcc tccaactctg cctccctcac catctctgga    240
```
ctgaggactg aggacgaggc tgactactac tgtcagtctt atgatgacac cactccctgg    300
gtgttcggcg agggaccaa gctgaccgtc ctaggt    336

<210> SEQ ID NO 66
<211> LENGTH: 112
<212> TYPE: PRT
<213> ORGANISM: Homo sapiens

<400> SEQUENCE: 66

Asn Phe Met Leu Thr Gln Pro His Ser Val Ser Glu Ser Pro Gly Lys
1               5                   10                  15

Thr Val Thr Ile Ser Cys Thr Arg Ser Ser Gly Tyr Ile Ala Ser Ser
            20                  25                  30

Tyr Val Gln Trp Tyr Gln Gln Arg Pro Gly Ser Ser Pro Thr Thr Val
        35                  40                  45

Ile Phe Glu Asp Asp Arg Arg Pro Ser Gly Val Pro Asp Arg Phe Ser
    50                  55                  60

Gly Ser Ile Asp Gly Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Asp
                85                  90                  95

Thr Thr Pro Trp Val Phe Gly Gly Gly Thr Lys Leu Thr Val Leu Gly
            100                 105                 110

<210> SEQ ID NO 67
<211> LENGTH: 360
<212> TYPE: DNA
<213> ORGANISM: Homo sapiens

<400> SEQUENCE: 67
gaggtgcagc tgttggagtc tgggggaggc ttggtacagc ctgggggggtc cctgagactc    60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagtcggc    300
agctggtacc tggaagattt tgatatctgg ggccggggga caatggtcac cgtctcgagt    360

<210> SEQ ID NO 68
<211> LENGTH: 120
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Trp Tyr Leu Glu Asp Phe Asp Ile Trp Gly Arg
            100                 105                 110

Gly Thr Met Val Thr Val Ser Ser
        115                 120

<210> SEQ ID NO 69
<211> LENGTH: 11
<212> TYPE: PRT
<213> ORGANISM: Homo sapiens

<400> SEQUENCE: 69

Val Gly Ser Trp Tyr Leu Glu Asp Phe Asp Ile
1               5                   10

<210> SEQ ID NO 70
<211> LENGTH: 342
<212> TYPE: DNA
<213> ORGANISM: Homo sapiens

<400> SEQUENCE: 70
aattttatgc tgactcagcc ccactctgtg tcggagtctc cggggaagac ggttaccatc      60
tcctgcaccc gcagcagtgg cagcattgcc agcaactatg ttcactggta tcagcagcgc     120
ccgggcagtt cacccaccac tgtgatctat gaggataacc gaagaccctc tggggtccct     180
gctcggttct ctggctccat cgacagctcc tccaactctg cctccctcac catctctgga     240
ctggagactg acgacgaggc tgactactac tgtcagtctt ctgataccac ctatcatgga     300
ggtgtggtat tcggcggagg gaccaagctg accgtcctag gt                        342

<210> SEQ ID NO 71
<211> LENGTH: 114
<212> TYPE: PRT
<213> ORGANISM: Homo sapiens

<400> SEQUENCE: 71

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val His Trp Tyr Gln Gln Arg Pro Gly Ser Ser Pro Thr Thr Val
        35                  40                  45

Ile Tyr Glu Asp Asn Arg Arg Pro Ser Gly Val Pro Ala Arg Phe Ser
    50                  55                  60

Gly Ser Ile Asp Ser Ser Ser Asn Ser Ala Ser Leu Thr Ile Ser Gly
65                  70                  75                  80

Leu Glu Thr Asp Asp Glu Ala Asp Tyr Tyr Cys Gln Ser Ser Asp Thr
                85                  90                  95

Thr Tyr His Gly Gly Val Val Phe Gly Gly Gly Thr Lys Leu Thr Val
            100                 105                 110

Leu Gly

<210> SEQ ID NO 72
<211> LENGTH: 13
<212> TYPE: PRT
<213> ORGANISM: Homo sapiens

<400> SEQUENCE: 72

Thr Arg Ser Ser Gly Ser Ile Ala Ser Asn Tyr Val His
1               5                   10

<210> SEQ ID NO 73
<211> LENGTH: 12
<212> TYPE: PRT
<213> ORGANISM: Homo sapiens

<400> SEQUENCE: 73

Gln Ser Ser Asp Thr Thr Tyr His Gly Gly Val Val
1               5                   10

<210> SEQ ID NO 74
<211> LENGTH: 366
<212> TYPE: DNA
<213> ORGANISM: Homo sapiens

<400> SEQUENCE: 74

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaaggcggt     300
aactacggtg attacttcga ctactttgac tactggggca gggacaat ggtcaccgtc       360 tcgagt                                                                366
```

<210> SEQ ID NO 75
<211> LENGTH: 122
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asn Tyr Gly Asp Tyr Phe Asp Tyr Phe Asp Tyr Trp
            100                 105                 110

Gly Arg Gly Thr Met Val Thr Val Ser Ser
        115                 120

<210> SEQ ID NO 76
<211> LENGTH: 13
<212> TYPE: PRT
<213> ORGANISM: Homo sapiens

<400> SEQUENCE: 76

Gly Gly Asn Tyr Gly Asp Tyr Phe Asp Tyr Phe Asp Tyr
1               5                   10

<210> SEQ ID NO 77
<211> LENGTH: 321

<212> TYPE: DNA
<213> ORGANISM: Homo sapiens

<400> SEQUENCE: 77

```
aattttatgc tgactcagcc ccactctgtg tcggagtctc cggggaagac ggtaaccatc    60
tcctgcaccc gcagcagtgg cagcattgcc agcaattatg tgcagtggta ccagcagcgc   120
ccgggcagtg cccccaccat tgtgatctat gaagataacc aaagaccctc tggggtccct   180
catcggttct ctggctccat cgacagctcc tccaactctg cctccctcac catctctgga   240
ctgaagactg aggacgaggc tgactactac tgtcagtctt atgaggggtt cggcggaggg   300
accaagctga ccgtcctagg t                                             321
```

<210> SEQ ID NO 78
<211> LENGTH: 107
<212> TYPE: PRT
<213> ORGANISM: Homo sapiens

<400> SEQUENCE: 78

```
Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Ile Ala Ser Asn
            20                  25                  30
Tyr Val Gln Trp Tyr Gln Gln Arg Pro Gly Ser Ala Pro Thr Ile Val
        35                  40                  45
Ile Tyr Glu Asp Asn Gln Arg Pro Ser Gly Val Pro His Arg Phe Ser
    50                  55                  60
Gly Ser Ile Asp Ser Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Glu Gly
                85                  90                  95
Phe Gly Gly Gly Thr Lys Leu Thr Val Leu Gly
            100                 105
```

<210> SEQ ID NO 79
<211> LENGTH: 6
<212> TYPE: PRT
<213> ORGANISM: Homo sapiens

<400> SEQUENCE: 79

```
Gln Ser Tyr Glu Gly Phe
1               5
```

<210> SEQ ID NO 80
<211> LENGTH: 360
<212> TYPE: DNA
<213> ORGANISM: Homo sapiens

<400> SEQUENCE: 80

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcactatc tccagagaca attccaagaa cacgctgtat    240
ctgcaaatga acagcctgag agccgaggac acggccgtgt attactgtgc gaaagatgga    300
tggaacgcgc tgggatggct tgaatcctgg ggccaggga caatggtcac cgtctcgagt     360
```

<210> SEQ ID NO 81

```
<211> LENGTH: 120
<212> TYPE: PRT
<213> ORGANISM: Homo sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Gln
            100                 105                 110

Gly Thr Met Val Thr Val Ser Ser
        115                 120

<210> SEQ ID NO 82
<211> LENGTH: 333
<212> TYPE: DNA
<213> ORGANISM: Homo sapiens

<400> SEQUENCE: 82
aattttatgc tgactcagcc ccacgctgtg tcggagtctc cggggaagac ggtgaccatt      60
tcctgcaccg gcagaaatgg caacattgcc agcaactatg tgcagtggta ccagcagcgc     120
ccggacagtg ccccacccct tataatcttt gaagataccc aaagaccctc tggggtccct     180
actcggctct caggtccat cgacacctcc tccaattctg cctccctcat catctcttca      240
ttgaggactg aggacgaggc tgattactac tgtcaatctt ctgattccaa cagggtgctg     300
ttcggcggag ggaccaaggt caccgtccta ggt                                  333

<210> SEQ ID NO 83
<211> LENGTH: 111
<212> TYPE: PRT
<213> ORGANISM: Homo sapiens

<400> SEQUENCE: 83

Asn Phe Met Leu Thr Gln Pro His Ala Val Ser Glu Ser Pro Gly Lys
1               5                   10                  15

Thr Val Thr Ile Ser Cys Thr Gly Arg Asn Gly Asn Ile Ala Ser Asn
            20                  25                  30

Tyr Val Gln Trp Tyr Gln Gln Arg Pro Asp Ser Ala Pro Thr Leu Ile
        35                  40                  45

Ile Phe Glu Asp Thr Gln Arg Pro Ser Gly Val Pro Thr Arg Leu Ser
    50                  55                  60

Gly Ser Ile Asp Thr Ser Ser Asn Ser Ala Ser Leu Ile Ile Ser Ser
65                  70                  75                  80

Leu Arg Thr Glu Asp Glu Ala Asp Tyr Tyr Cys Gln Ser Ser Asp Ser
                85                  90                  95

Asn Arg Val Leu Phe Gly Gly Gly Thr Lys Val Thr Val Leu Gly
            100                 105                 110
```

<210> SEQ ID NO 84
<211> LENGTH: 13
<212> TYPE: PRT
<213> ORGANISM: Homo sapiens

<400> SEQUENCE: 84

Thr Gly Arg Asn Gly Asn Ile Ala Ser Asn Tyr Val Gln
1               5                   10

<210> SEQ ID NO 85
<211> LENGTH: 7
<212> TYPE: PRT
<213> ORGANISM: Homo sapiens

<400> SEQUENCE: 85

Glu Asp Thr Gln Arg Pro Ser
1               5

<210> SEQ ID NO 86
<211> LENGTH: 9
<212> TYPE: PRT
<213> ORGANISM: Homo sapiens

<400> SEQUENCE: 86

Gln Ser Ser Asp Ser Asn Arg Val Leu
1               5

<210> SEQ ID NO 87
<211> LENGTH: 360
<212> TYPE: DNA
<213> ORGANISM: Homo sapiens

<400> SEQUENCE: 87
gaggtgcagc tgttggagtc tgggggaggc ttggtacagc ctgggggtc cctgagactc     60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaagatttt    300
tgggttatta cgagtgggaa tgactactgg gggcgggga ccacggtcac cgtctcgagt    360

<210> SEQ ID NO 88
<211> LENGTH: 120
<212> TYPE: PRT
<213> ORGANISM: Homo sapiens

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Phe Trp Val Ile Thr Ser Gly Asn Asp Tyr Trp Gly Arg
            100                 105                 110

Gly Thr Thr Val Thr Val Ser Ser
        115                 120

<210> SEQ ID NO 89
<211> LENGTH: 11
<212> TYPE: PRT
<213> ORGANISM: Homo sapiens

<400> SEQUENCE: 89

Asp Phe Trp Val Ile Thr Ser Gly Asn Asp Tyr
1               5                   10

<210> SEQ ID NO 90
<211> LENGTH: 336
<212> TYPE: DNA
<213> ORGANISM: Homo sapiens

<400> SEQUENCE: 90
aattttatgc tgactcagcc ccactctgtg tcggagtctc cggggaagac ggtgaccatc      60
tcctgcaccc gcagcagtgg cagcattgct agcaattatg tgcagtggta ccagcagcgc    120
ccgggcagtt cccccaccac tgtgatcttt gaagataacc gaagaccctc tggggtccct    180
gatcggtttt ctggctccat cgacacctcc tccaactctg cctccctcac catctctgga    240
ctgaagactg aggacgaggc tgactactac tgtcagtctt ttgatagcac caatcttgtg    300
gtgttcggcg gagggaccaa gctgaccgtc ctaggt                              336

<210> SEQ ID NO 91
<211> LENGTH: 112
<212> TYPE: PRT
<213> ORGANISM: Homo sapiens

<400> SEQUENCE: 91

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Phe Glu Asp Asn Arg Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Leu Val Val Phe Gly Gly Gly Thr Lys Leu Thr Val Leu Gly
            100                 105                 110

<210> SEQ ID NO 92
<211> LENGTH: 10
<212> TYPE: PRT
<213> ORGANISM: Homo sapiens

<400> SEQUENCE: 92

Gln Ser Phe Asp Ser Thr Asn Leu Val Val
1               5                   10

<210> SEQ ID NO 93
```

<211> LENGTH: 360
<212> TYPE: DNA
<213> ORGANISM: Homo sapiens

<400> SEQUENCE: 93

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaaagatgga    300
tggaacgcgc tgggatggct tgaatcctgg gggaagggga ccacggtcac cgtctcgagt    360
```

<210> SEQ ID NO 94
<211> LENGTH: 120
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Lys
            100                 105                 110

Gly Thr Thr Val Thr Val Ser Ser
        115                 120

<210> SEQ ID NO 95
<211> LENGTH: 336
<212> TYPE: DNA
<213> ORGANISM: Homo sapiens

<400> SEQUENCE: 95

```
aattttatgc tgactcagcc ccactctgtg tcggagtctc cggggaagac ggtaaccatc      60
tcctgcgccg gcagcagtgg cagcattgcc agcaactatg tgcagtggta ccagcagcgc    120
ccgggcagtg cccccaccgc tgtgatctat gaggataacc aaagaccctc tggggtccct    180
gatcgattct ctggctccat cgacagctcc tccaactctg cctccctcac catctctgga    240
ctgaagactg aggacgaggc tgactactac tgtcaatctt actcttacaa caatcaggtc    300
gtgttcggcg gagggaccaa ggtcaccgtc ctaggt                              336
```

<210> SEQ ID NO 96
<211> LENGTH: 112
<212> TYPE: PRT
<213> ORGANISM: Homo sapiens

<400> SEQUENCE: 96

Asn Phe Met Leu Thr Gln Pro His Ser Val Ser Glu Ser Pro Gly Lys

```
                1               5                   10                  15
            Thr Val Thr Ile Ser Cys Ala Gly Ser Ser Gly Ser Ile Ala Ser Asn
                            20                  25                  30
            Tyr Val Gln Trp Tyr Gln Gln Arg Pro Gly Ser Ala Pro Thr Ala Val
                        35                  40                  45
            Ile Tyr Glu Asp Asn Gln Arg Pro Ser Gly Val Pro Asp Arg Phe Ser
                    50                  55                  60
            Gly Ser Ile Asp Ser Ser Asn Ser Ala Ser Leu Thr Ile Ser Gly
            65                  70                  75                  80
            Leu Lys Thr Glu Asp Glu Ala Asp Tyr Tyr Cys Gln Ser Tyr Ser Tyr
                            85                  90                  95
            Asn Asn Gln Val Val Phe Gly Gly Gly Thr Lys Val Thr Val Leu Gly
                            100                 105                 110

<210> SEQ ID NO 97
<211> LENGTH: 13
<212> TYPE: PRT
<213> ORGANISM: Homo sapiens

<400> SEQUENCE: 97

Ala Gly Ser Ser Gly Ser Ile Ala Ser Asn Tyr Val Gln
1               5                   10

<210> SEQ ID NO 98
<211> LENGTH: 10
<212> TYPE: PRT
<213> ORGANISM: Homo sapiens

<400> SEQUENCE: 98

Gln Ser Tyr Ser Tyr Asn Asn Gln Val Val
1               5                   10

<210> SEQ ID NO 99
<211> LENGTH: 296
<212> TYPE: DNA
<213> ORGANISM: Homo sapiens

<400> SEQUENCE: 99
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaga         296

<210> SEQ ID NO 100
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 100
ctcttctgag atgagttttt g                                                21

<210> SEQ ID NO 101
<211> LENGTH: 30
<212> TYPE: DNA
<213> ORGANISM: Artificial Sequence
<220> FEATURE:
<223> OTHER INFORMATION: chemically synthesized primer
```

<400> SEQUENCE: 101
ttattattcg caattccttt agttgttcct                                           30

<210> SEQ ID NO 102
<211> LENGTH: 369
<212> TYPE: DNA
<213> ORGANISM: Homo sapiens

<400> SEQUENCE: 102
gaggtgcagc tgttggagtc tggggaggc ttggtacagc ctggggggtc cctgagactc          60
tcctgtgcag cctctggatt cacctttagc agctatgcca tgagctgggt ccgccaggct        120
ccagggaagg ggctggagtg gtctcagct attagtggta gtggtggtag cacatactac         180
gcagactccg tgaagggccg gttcaccatc tccagagaca attccaagaa cacgctgtat        240
ctgcaaatga acagcctgag agccgaggac acggccgtat attactgtgc gaaagatggt       300
agcagtggct ggtacgtacc acactggttc gaccccctggg gccggggcac cctggtcacc      360
gtctcgagt                                                                369

<210> SEQ ID NO 103
<211> LENGTH: 123
<212> TYPE: PRT
<213> ORGANISM: Homo sapiens

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
            100                 105                 110

Trp Gly Arg Gly Thr Leu Val Thr Val Ser Ser
        115                 120

<210> SEQ ID NO 104
<211> LENGTH: 336
<212> TYPE: DNA
<213> ORGANISM: Homo sapiens

<400> SEQUENCE: 104
aattttatgc tgactcagcc ccactctgtg tcggagtctc cggggaagac ggtaaccatc          60
tcctgcactc gcagcagtgg cagcattgtc agcaactatg tgcagtggta ccaacagcgc        120
ccgggcagtg cccccaccac tgtcatctat gaggataacc ggagaccctc tggggtccct        180
gatcggttct ctggctccat cgacagctcc tccaatactg cctccctcac catctctggg        240
ctggaggctg aggacgaggc tgactactac tgtcagtctt atgatggcag caatcgttgg        300
atgttcggcg gagggaccaa gctgaccgtc ctaggt                                   336

<210> SEQ ID NO 105
<211> LENGTH: 112
<212> TYPE: PRT
<213> ORGANISM: Homo sapiens

<400> SEQUENCE: 105

```
Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Ile Val Ser Asn
            20                  25                  30
Tyr Val Gln Trp Tyr Gln Gln Arg Pro Gly Ser Ala Pro Thr Thr Val
        35                  40                  45
Ile Tyr Glu Asp Asn Arg Arg Pro Ser Gly Val Pro Asp Arg Phe Ser
    50                  55                  60
Gly Ser Ile Asp Ser Ser Ser Asn Thr Ala Ser Leu Thr Ile Ser Gly
65                  70                  75                  80
Leu Glu Ala Glu Asp Glu Ala Asp Tyr Tyr Cys Gln Ser Tyr Asp Gly
                85                  90                  95
Ser Asn Arg Trp Met Phe Gly Gly Gly Thr Lys Leu Thr Val Leu Gly
            100                 105                 110
```

<210> SEQ ID NO 106
<211> LENGTH: 13
<212> TYPE: PRT
<213> ORGANISM: Homo sapiens

<400> SEQUENCE: 106

```
Thr Arg Ser Ser Gly Ser Ile Val Ser Asn Tyr Val Gln
1               5                   10
```

<210> SEQ ID NO 107
<211> LENGTH: 7
<212> TYPE: PRT
<213> ORGANISM: Homo sapiens

<400> SEQUENCE: 107

```
Glu Asp Asn Arg Arg Pro Ser
1               5
```

<210> SEQ ID NO 108
<211> LENGTH: 296
<212> TYPE: DNA
<213> ORGANISM: Homo sapiens

<400> SEQUENCE: 108

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgatagcag caatca       296
```

<210> SEQ ID NO 109
<211> LENGTH: 52
<212> TYPE: DNA
<213> ORGANISM: Homo sapiens

<400> SEQUENCE: 109

```
accacactgg ttcgacccct ggggccgggg caccctggtc accgtctcga gt            52
```

<210> SEQ ID NO 110
<211> LENGTH: 17
<212> TYPE: PRT
<213> ORGANISM: Homo sapiens

<400> SEQUENCE: 110

Pro His Trp Phe Asp Pro Trp Gly Arg Gly Thr Leu Val Thr Val Ser
1               5                   10                  15

Ser

<210> SEQ ID NO 111
<211> LENGTH: 52
<212> TYPE: DNA
<213> ORGANISM: Homo sapiens

<400> SEQUENCE: 111
ctactggtac ttcgatctct ggggccgtgg caccctggtc actgtctcct ca        52

<210> SEQ ID NO 112
<211> LENGTH: 17
<212> TYPE: PRT
<213> ORGANISM: Homo sapiens

<400> SEQUENCE: 112

Tyr Trp Tyr Phe Asp Leu Trp Gly Arg Gly Thr Leu Val Thr Val Ser
1               5                   10                  15

Ser

<210> SEQ ID NO 113
<211> LENGTH: 50
<212> TYPE: DNA
<213> ORGANISM: Homo sapiens

<400> SEQUENCE: 113
cacactggtt cgacccctgg ggccggggca ccctggtcac cgtctcgagt            50

<210> SEQ ID NO 114
<211> LENGTH: 16
<212> TYPE: PRT
<213> ORGANISM: Homo sapiens

<400> SEQUENCE: 114

His Trp Phe Asp Pro Trp Gly Arg Gly Thr Leu Val Thr Val Ser Ser
1               5                   10                  15

<210> SEQ ID NO 115
<211> LENGTH: 50
<212> TYPE: DNA
<213> ORGANISM: Homo sapiens

<400> SEQUENCE: 115
acaactggtt cgacccctgg ggccagggaa ccctggtcac cgtctcctca            50

<210> SEQ ID NO 116
<211> LENGTH: 16
<212> TYPE: PRT
<213> ORGANISM: Homo sapiens

<400> SEQUENCE: 116

Asn Trp Phe Asp Pro Trp Gly Gln Gly Thr Leu Val Thr Val Ser Ser
1               5                   10                  15

```
<210> SEQ ID NO 117
<211> LENGTH: 38
<212> TYPE: PRT
<213> ORGANISM: Homo sapiens

<400> SEQUENCE: 117

Asp Arg Phe Ser Gly Ser Ile Asp Ser Ser Asn Ser Ala Ser Leu
1               5                   10                  15

Thr Ile Ser Gly Leu Lys Thr Glu Asp Glu Ala Asp Tyr Tyr Cys Gln
            20                  25                  30

Ser Tyr Asp Ser Ser Asn
            35

<210> SEQ ID NO 118
<211> LENGTH: 52
<212> TYPE: PRT
<213> ORGANISM: Homo sapiens

<400> SEQUENCE: 118

Asp Arg Phe Ser Gly Ser Ile Asp Ser Ser Asn Thr Ala Ser Leu
1               5                   10                  15

Thr Ile Ser Gly Leu Glu Ala Glu Asp Glu Ala Asp Tyr Tyr Cys Gln
            20                  25                  30

Ser Tyr Asp Gly Ser Asn Arg Trp Met Phe Gly Gly Gly Thr Lys Leu
            35                  40                  45

Thr Val Leu Gly
    50
```

ANTI-INTERFERON GAMMA ANTIBODIES AND METHODS OF USE THEREOF

RELATED APPLICATION

This application is a continuation application of U.S. application Ser. No. 12/702,013, filed Feb. 8, 2010, which is a continuation application of U.S. application Ser. No. 11/342,020, filed Jan. 27, 2006, now issued as U.S. Pat. No. 7,700,098, which claims the benefit of and priority under 35 U.S.C. §119(e) to U.S. Provisional Application No. 60/648,219, filed Jan. 27, 2005, each of which is hereby incorporated by reference in its entirety.

INCORPORATION OF SEQUENCE LISTING

The contents of the text file named "409C02USseqlist.txt," which was created on Oct. 18, 2013 and is 58.9 KB in size, are hereby incorporated by reference in their entirety.

FIELD OF THE INVENTION

This invention relates generally to fully human anti-interferon gamma antibodies as well as to methods for use thereof.

BACKGROUND OF THE INVENTION

Human interferon gamma (IFNγ, IFN-gamma) is a lymphokine produced by activated T-lymphocytes and natural killer cells. It manifests anti-proliferative, antiviral and immunomodulatory activities and binds to IFNγ-R, a heterodimeric receptor on most primary cells of the immune system, and triggers a cascade of events leading to inflammation. The antiviral and immunomodulatory activity of IFNγ is known to have beneficial effects in a number of clinical conditions. However, there are many clinical settings in which IFNγ-activity is known to have deleterious effects. For example, autoimmune diseases are associated with high levels of IFNγ in the blood and diseased tissue from autoimmune patients. IFNγ-activity has also been linked to such disease states as cachexia and septic shock.

Accordingly, there exists a need for therapies that target IFNγ activity.

SUMMARY OF THE INVENTION

The present invention provides fully human monoclonal antibodies specifically directed against interferon gamma (IFNγ, also referred to herein as IFN-gamma). Exemplary monoclonal antibodies include NI-0501; AC1.2R3P2_A6 (also referred to herein as "A6"); AC1.2R3P2_B4 (also referred to herein as "B4"); AD1.4R4P1_B9 (also referred to herein as "B9"); AD1.4R4P2_C9 (also referred to herein as "C9"); AC1.4R4P2_C10 (also referred to herein as "C10"); AC1.2R3P7_D3 (also referred to herein as "D3"); AD1.2R2P2_D6 (also referred to herein as "D6"); AC1.2R2P2_D8 (also referred to herein as "D8"); AD1.3R3P6_E1 (also referred to herein as "E1"); AD1.3R3P5_F8 (also referred to herein as "F8"); AD1.3R3P6_F9 (also referred to herein as "F9"); AD1.4R4P2_G7 (also referred to herein as "G7"); AD1.1R3P3_G9 (also referred to herein as "G9"); and AD1.3R3P6_G10 (also referred to herein as "G10") described herein. Alternatively, the monoclonal antibody is an antibody that binds to the same epitope as NI-0501; AC1.2R3P2_B4; AD1.4R4P1_B9; AD1.4R4P2_C9; AC1.4R4P2_C10; AC1.2R3P7_D3; AD1.2R2P2_D6; AC1.2R2P2_D8; AD1.3R3P6_E1; AD1.3R3P5_F8; AD1.3R3P6_F9; AD1.4R4P2_G7; AD1.1R3P3_G9; or AD1.3R3P6_G10. The antibodies are respectively referred to herein as huIFNγ antibodies.

A huIFNγ antibody contains a heavy chain variable having the amino acid sequence of SEQ ID NOS: 2, 12, 20, 28, 36, 42, 51, 58, 63, 68, 75, 81, 88, 94, or 103 and a light chain variable having the amino acid sequence of SEQ ID NOS: 7, 15, 23, 31, 38, 47, 54, 60, 66, 71, 78, 83, 91, 96 or 105. Preferably, the three heavy chain complementarity determining regions (CDRs) include an amino acid sequence at least 90%, 92%, 95%, 97% 98%, 99% or more identical a sequence selected from the group consisting of SYAMS (SEQ ID NO:3); AISGSGGSTYYADSVKG (SEQ ID NO:4); DGSSGWYVPHWF DP (SEQ ID NO:5); DHSSGWYVISGMDV (SEQ ID NO:13); DLTVGGPWYYFDY (SEQ ID NO:21); DGWNALGWLES (SEQ ID NO:29); SNAMS (SEQ ID NO:43); TLTGSGGTAYYADSVEG (SEQ ID NO:44); GTELVGGGLDN (SEQ ID NO:45); RSFDSGGSFEY (SEQ ID NO:64); VGSWYLEDFDI (SEQ ID NO:69); GGNYGDYFDYFDY (SEQ ID NO:76); and DFWVITSGNDY (SEQ ID NO:89); and a light chain with three CDR that include an amino acid sequence at least 90%, 92%, 95%, 97% 98%, 99% or more identical to a sequence selected from the group consisting of the amino acid sequence of TRSSGSIASNYVQ (SEQ ID NO:8); EDNQRPS (SEQ ID NO:9); QSYDGSNRWM (SEQ ID NO:10); TRSSGSIASNYVQ (SEQ ID NO:16); EDNQRPS (SEQ ID NO:17); QSNDSDNVV (SEQ ID NO:18); DDDQRPS (SEQ ID NO:25); QSYDSSNVV (SEQ ID NO:26); TRSGGSIGSYYVQ (SEQ ID NO:32); DDKKRPS (SEQ ID NO:33); QSYDSNNLVV (SEQ ID NO:34); TRSSGTIASNYVQ (SEQ ID NO:39); QSYDNSNHWV (SEQ ID NO:40); TGSGGSIATNYVQ (SEQ ID NO:48); QSYDSDNHHVV (SEQ ID NO:49); TGSSGSIASNYVQ (SEQ ID NO:55); QSYDSSNQEVV (SEQ ID NO:56); QSYDSNNFWV (SEQ ID NO:61); TRSSGSIASNYVH (SEQ ID NO:72); QSSDTTYHGGVV (SEQ ID NO:73); QSYEGF (SEQ ID NO:79); TGRNGNIASNYVQ (SEQ ID NO:84); EDTQRPS (SEQ ID NO:85); QSSDSNRVL (SEQ ID NO:86); QSFDSTNLVV (SEQ ID NO:92); AGSSGSIASNYVQ (SEQ ID NO:97); QSYSYNNQVV (SEQ ID NO:98); TRSSGSIVSNYVQ (SEQ ID NO:106); EDNRRPS (SEQ ID NO:107). The antibody binds IFNγ.

The huIFNγ antibodies of the invention include a V$_H$ CDR1 region comprising the amino acid sequence SYAMS (SEQ ID NO:3) or SNAMS (SEQ ID NO:43); a V$_H$ CDR2 region comprising the amino acid sequence AISGSGGSTYYADSVKG (SEQ ID NO:4) or TLTGSGGTAYYADSVEG (SEQ ID NO:44), and a V$_H$ CDR3 region comprising an amino acid sequence selected from the group consisting of DGSSGWYVPHWFDP (SEQ ID NO:5); DHSSGWYVISGMDV (SEQ ID NO:13); DLTVGGPWYYFDY (SEQ ID NO:21); DGWNALGWLES (SEQ ID NO:29); GTELVGGGLDN (SEQ ID NO:45); RSFDSGGSFEY (SEQ ID NO:64); VGSWYLEDFDI (SEQ ID NO:69); GGNYGDYFDYFDY (SEQ ID NO:76); and DFWVITSGNDY (SEQ ID NO:89).

The huIFNγ antibodies include a V$_L$ CDR1 region comprising an amino acid sequence selected from the group consisting of TRSSGSIASNYVQ (SEQ ID NO:8); TRSSGSIASNYVQ (SEQ ID NO:16); TRSGGSIGSYYVQ (SEQ ID NO:32); TRSSGTIASNYVQ (SEQ ID NO:39); TGSGGSIATNYVQ (SEQ ID NO:48); TGSSGSIASNYVQ (SEQ ID NO:55); TRSSGSIASNYVH (SEQ ID NO:72);

TGRNGNIASNYVQ (SEQ ID NO:84); AGSSGSIASNYVQ (SEQ ID NO:97) and TRSSGSIVSNYVQ (SEQ ID NO:106); a $V_L$ CDR2 region comprising an amino acid sequence selected from the group consisting of EDNQRPS (SEQ ID NO:9); EDNQRPS (SEQ ID NO:17); DDDQRPS (SEQ ID NO:25); DDKKRPS (SEQ ID NO:33); EDTQRPS (SEQ ID NO:85) and EDNRRPS (SEQ ID NO:107); and a $V_L$ CDR3 region comprising an amino acid sequence selected from the group consisting of QSYDGSNRWM (SEQ ID NO:10); QSNDSDNVV (SEQ ID NO:18); QSYDSSNVV (SEQ ID NO:26); QSYDSNN-LVV (SEQ ID NO:34); QSYDNSNHWV (SEQ ID NO:40); QSYDSDNHHVV (SEQ ID NO:49); QSYDSSNQEVV (SEQ ID NO:56); QSYDSNNFWV (SEQ ID NO:61); QSS-DTTYHGGVV (SEQ ID NO:73); QSYEGF (SEQ ID NO:79); QSSDSNRVL (SEQ ID NO:86); QSFDSTNLVV (SEQ ID NO:92); and QSYSYNNQVV (SEQ ID NO:98).

The huIFNγ antibodies include, for example, a $V_H$ CDR1 region comprising the amino acid sequence SYAMS (SEQ ID NO:3) or SNAMS (SEQ ID NO:43); a $V_H$ CDR2 region comprising the amino acid sequence AISGSGGSTYYADS-VKG (SEQ ID NO:4) or TLTGSGGTAYYADSVEG (SEQ ID NO:44); a $V_H$ CDR3 region comprising an amino acid sequence selected from the group consisting of DGSS-GWYVPHWFDP (SEQ ID NO:5); DHSSGWYVISGMDV (SEQ ID NO:13); DLTVGGPWYYFDY (SEQ ID NO:21); DGWNALGWLES (SEQ ID NO:29); GTELVGGGLDN (SEQ ID NO:45); RSFDSGGSFEY (SEQ ID NO:64); VGSWYLEDFDI (SEQ ID NO:69); GGNYGDYFDYFDY (SEQ ID NO:76); and DFWVITSGNDY (SEQ ID NO:89); a $V_L$ CDR1 region comprising an amino acid sequence selected from the group consisting of TRSSGSIASNYVQ (SEQ ID NO:8); TRSSGSIASNYVQ (SEQ ID NO:16); TRSGGSIGSYYVQ (SEQ ID NO:32); TRSSGTIASNYVQ (SEQ ID NO:39); TGSGGSIATNYVQ (SEQ ID NO:48); TGSSGSIASNYVQ (SEQ ID NO:55); TRSSGSIASNYVH (SEQ ID NO:72); TGRNGNIASNYVQ (SEQ ID NO:84); AGSSGSIASNYVQ (SEQ ID NO:97) and TRSSGSIVSNYVQ (SEQ ID NO:106); a $V_L$ CDR2 region comprising an amino acid sequence selected from the group consisting of EDNQRPS (SEQ ID NO:9); EDNQRPS (SEQ ID NO:17); DDDQRPS (SEQ ID NO:25); DDKKRPS (SEQ ID NO:33); EDTQRPS (SEQ ID NO:85) and EDNRRPS (SEQ ID NO:107); and a $V_L$ CDR3 region comprising an amino acid sequence selected from the group consisting of QSYDGSNRWM (SEQ ID NO:10); QSNDSDNVV (SEQ ID NO:18); QSYDSSNVV (SEQ ID NO:26); QSYDSNN-LVV (SEQ ID NO:34); QSYDNSNHWV (SEQ ID NO:40); QSYDSDNHHVV (SEQ ID NO:49); QSYDSSNQEVV (SEQ ID NO:56); QSYDSNNFWV (SEQ ID NO:61); QSS-DTTYHGGVV (SEQ ID NO:73); QSYEGF (SEQ ID NO:79); QSSDSNRVL (SEQ ID NO:86); QSFDSTNLVV (SEQ ID NO:92); and QSYSYNNQVV (SEQ ID NO:98).

The heavy chain of a huIFNγ antibody is derived from a germ line V (variable) gene such as, for example, the DP47 (IGHV3-23) germline gene (GenBank Accession No. M99660) or a nucleic acid sequence homologous to the human DP47 germline gene sequence. The nucleic acid sequence for the DP47 (IGHV 3-23) germline gene includes, for example, the nucleic acid sequence shown below:

```
(SEQ ID NO: 99)
GAGGTGCAGCTGTTGGAGTCTGGGGGAGGCTTGGTACAGCCTGGGGGGTCCCTGAGACTC

TCCTGTGCAGCCTCTGGATTCACCTTTAGCAGCTATGCCATGAGCTGGGTCCGCCAGGCT

CCAGGGAAGGGGCTGGAGTGGGTCTCAGCTATTAGTGGTAGTGGTGGTAGCACATACTAC

GCAGACTCCGTGAAGGGCCGGTTCACCATCTCCAGAGACAATTCCAAGAACACGCTGTAT

CTGCAAATGAACAGCCTGAGAGCCGAGGACACGGCCGTATATTACTGTGCGAAAGA
```

The light chain of a huIFNγ antibody is derived from a Ig lambda light chain variable region germline gene such as, for example, the IGLV6-57 or V1-22 (GenBank Accession No. Z73673) or a nucleic acid sequence homologous to the human IGLV6-57 germline gene sequence. The nucleic acid sequence for the IGLV6-57 germline gene includes, for example, the nucleic acid sequence shown below:

```
(SEQ ID NO: 108)
AATTTTATGCTGACTCAGCCCCACTCTGTGTCGGAGTCTCCGGGGAAGACGGTAACCATC

TCCTGCACCCGCAGCAGTGGCAGCATTGCCAGCAACTATGTGCAGTGGTACCAGCAGCGC

CCGGGCAGTTCCCCCACCACTGTGATCTATGAGGATAACCAAAGACCCTCTGGGGTCCCT

GATCGGTTCTCTGGCTCCATCGACAGCTCCTCCAACTCTGCCTCCCTCACCATCTCTGGA

CTGAAGACTGAGGACGAGGCTGACTACTACTGTCAGTCTTATGATAGCAGCAATCA
```

In another aspect, the invention provides methods of treating, preventing or alleviating a symptom of an immune-related disorder by administering a huIFNγ antibody to a subject. For example, the huIFNγ antibodies are used to treat, prevent or alleviate a symptom associated with immune-related disorders such as Crohn's Disease, systemic lupus erythematosus, psoriasis, sarcoidosis, rheumatoid arthritis, vasculitis, atopic dermatitis and secondary progressive multiple sclerosis. Optionally, the subject is further administered with a second agent such as, but not limited to, an anti-cytokine or anti-chemokine reagent that recognizes cytokines such as interleukin 1 (IL-1), IL-2, IL-4, IL-6, IL-12, IL-13, IL-15, IL-17, IL-18, IL-20, IL-21, IL-22, IL-23, IL-27 and IL-31, and/or chemokines such as MIP1 alpha, MIP1 beta, RANTES, MCP1, IP-10, ITAC, MIG, SDF and fractalkine.

The subject is suffering from or is predisposed to developing an immune related disorder, such as, for example, an autoimmune disease or an inflammatory disorder.

BRIEF DESCRIPTION OF THE DRAWINGS

FIGS. 1A, 1B, 1C, 1D, 1E, 1F, 1G and 1H are a series of representations of the nucleotide sequence and amino acid sequences for the variable light and variable heavy regions of the huIFNγ antibodies NI-0501 and AC1.2R3P2_A6. FIG. 1A depicts the nucleotide sequence encoding the variable region of the heavy chain of NI-0501, and FIG. 1B represents the amino acid sequence encoded by the nucleotide sequence shown in FIG. 1A. The complementarity determining regions (CDRs) are underlined in FIG. 1B. FIG. 1C depicts the nucleotide sequence encoding the variable region of the light chain of NI-0501, and FIG. 1D represents the amino acid sequence encoded by the nucleotide sequence shown in FIG. 1C. The CDRs are underlined in FIG. 1D. FIG. 1E depicts the nucleotide sequence encoding the variable region of the heavy chain of AC1.2R3P2_A6, and FIG. 1F represents the amino acid sequence encoded by the nucleotide sequence shown in FIG. 1E. The CDRs are underlined in FIG. 1F. FIG. 1G depicts the nucleotide sequence encoding the variable region of the light chain of AC1.2R3P2_A6, and FIG. 1H represents the amino acid sequence encoded by the nucleotide sequence shown in FIG. 1G. The CDRs are underlined in FIG. 1H.

FIGS. 2A, 2B, 2C and 2D are a series of representations of the nucleotide sequence and amino acid sequences for the variable light and variable heavy regions of the huIFNγ antibody AC1.2R3P2_B4. FIG. 2A depicts the nucleotide sequence encoding the variable region of the heavy chain, and FIG. 2B represents the amino acid sequence encoded by the nucleotide sequence shown in FIG. 2A. The CDRs are underlined in FIG. 2B. FIG. 2C depicts the nucleotide sequence encoding the variable region of the light chain, and FIG. 2D represents the amino acid sequence encoded by the nucleotide sequence shown in FIG. 2C. The CDRs are underlined in FIG. 2D.

FIGS. 3A, 3B, 3C and 3D are a series of representations of the nucleotide sequence and amino acid sequences for the variable light and variable heavy regions of the huIFNγ antibody AD1.4R4P1_B9. FIG. 3A depicts the nucleotide sequence encoding the variable region of the heavy chain, and FIG. 3B represents the amino acid sequence encoded by the nucleotide sequence shown in FIG. 3A. The CDRs are underlined in FIG. 3B. FIG. 3C depicts the nucleotide sequence encoding the variable region of the light chain, and FIG. 3D represents the amino acid sequence encoded by the nucleotide sequence shown in FIG. 3C. The CDRs are underlined in FIG. 3D.

FIGS. 4A, 4B, 4C and 4D are a series of representations of the nucleotide sequence and amino acid sequences for the variable light and variable heavy regions of the huIFNγ antibody AD1.4R4P2_C9. FIG. 4A depicts the nucleotide sequence encoding the variable region of the heavy chain, and FIG. 4B represents the amino acid sequence encoded by the nucleotide sequence shown in FIG. 4A. The CDRs are underlined in FIG. 4B. FIG. 4C depicts the nucleotide sequence encoding the variable region of the light chain, and FIG. 4D represents the amino acid sequence encoded by the nucleotide sequence shown in FIG. 4C. The CDRs are underlined in FIG. 4D.

FIGS. 5A, 5B, 5C and 5D are a series of representations of the nucleotide sequence and amino acid sequences for the variable light and variable heavy regions of the huIFNγ antibody AC1.4R4P2_C10. FIG. 5A depicts the nucleotide sequence encoding the variable region of the heavy chain, and FIG. 5B represents the amino acid sequence encoded by the nucleotide sequence shown in FIG. 5A. The CDRs are underlined in FIG. 5B. FIG. 5C depicts the nucleotide sequence encoding the variable region of the light chain, and FIG. 5D represents the amino acid sequence encoded by the nucleotide sequence shown in FIG. 5C. The CDRs are underlined in FIG. 5D.

FIGS. 6A, 6B, 6C and 6D are a series of representations of the nucleotide sequence and amino acid sequences for the variable light and variable heavy regions of the huIFNγ antibody AC1.2R3P7_D3. FIG. 6A depicts the nucleotide sequence encoding the variable region of the heavy chain, and FIG. 6B represents the amino acid sequence encoded by the nucleotide sequence shown in FIG. 6A. The CDRs are underlined in FIG. 6B. FIG. 6C depicts the nucleotide sequence encoding the variable region of the light chain, and FIG. 6D represents the amino acid sequence encoded by the nucleotide sequence shown in FIG. 6C. The CDRs are underlined in FIG. 6D.

FIGS. 7A, 7B, 7C and 7D are a series of representations of the nucleotide sequence and amino acid sequences for the variable light and variable heavy regions of the huIFNγ antibody AD1.2R2P2_D6. FIG. 7A depicts the nucleotide sequence encoding the variable region of the heavy chain, and FIG. 7B represents the amino acid sequence encoded by the nucleotide sequence shown in FIG. 7A. The CDRs are underlined in FIG. 7B. FIG. 7C depicts the nucleotide sequence encoding the variable region of the light chain, and FIG. 7D represents the amino acid sequence encoded by the nucleotide sequence shown in FIG. 7C. The CDRs are underlined in FIG. 7D.

FIGS. 8A, 8B, 8C and 8D are a series of representations of the nucleotide sequence and amino acid sequences for the variable light and variable heavy regions of the huIFNγ antibody AC1.2R2P2_D8. FIG. 8A depicts the nucleotide sequence encoding the variable region of the heavy chain, and FIG. 8B represents the amino acid sequence encoded by the nucleotide sequence shown in FIG. 8A. The CDRs are underlined in FIG. 8B. FIG. 8C depicts the nucleotide sequence encoding the variable region of the light chain, and FIG. 8D represents the amino acid sequence encoded by the nucleotide sequence shown in FIG. 8C. The CDRs are underlined in FIG. 8D.

FIGS. 9A, 9B, 9C and 9D are a series of representations of the nucleotide sequence and amino acid sequences for the variable light and variable heavy regions of the huIFNγ antibody AD1.3R3P6_E1. FIG. 9A depicts the nucleotide sequence encoding the variable region of the heavy chain, and FIG. 9B represents the amino acid sequence encoded by the nucleotide sequence shown in FIG. 9A. The CDRs are underlined in FIG. 9B. FIG. 9C depicts the nucleotide sequence encoding the variable region of the light chain, and FIG. 9D represents the amino acid sequence encoded by the nucleotide sequence shown in FIG. 9C. The CDRs are underlined in FIG. 9D.

FIGS. 10A, 10B, 10C and 10D are a series of representations of the nucleotide sequence and amino acid sequences for the variable light and variable heavy regions of the huIFNγ antibody AD1.3R3P5_F8. FIG. 10A depicts the nucleotide sequence encoding the variable region of the heavy chain, and FIG. 10B represents the amino acid sequence encoded by the nucleotide sequence shown in FIG. 10A. The CDRs are underlined in FIG. 10B. FIG. 10C depicts the nucleotide sequence encoding the variable region of the light chain, and FIG. 10D represents the amino acid sequence encoded by the nucleotide sequence shown in FIG. 10C. The CDRs are underlined in FIG. 10D.

FIGS. 11A, 11B, 11C and 11D are a series of representations of the nucleotide sequence and amino acid sequences for the variable light and variable heavy regions of the huIFNγ antibody AD1.3R3P6_F9. FIG. 11A depicts the nucleotide sequence encoding the variable region of the heavy chain, and FIG. 11B represents the amino acid sequence encoded by the nucleotide sequence shown in FIG. 11A. The CDRs are underlined in FIG. 11B. FIG. 11C depicts the nucleotide sequence encoding the variable region of the light chain, and FIG. 11D represents the amino acid sequence encoded by the nucleotide sequence shown in FIG. 11C. The CDRs are underlined in FIG. 11D.

FIGS. 12A, 12B, 12C and 12D are a series of representations of the nucleotide sequence and amino acid sequences for the variable light and variable heavy regions of the huIFNγ antibody AD1.4R4P2_G7. FIG. 12A depicts the nucleotide sequence encoding the variable region of the heavy chain, and FIG. 12B represents the amino acid sequence encoded by the nucleotide sequence shown in FIG. 12A. The CDRs are underlined in FIG. 12B. FIG. 12C depicts the nucleotide sequence encoding the variable region of the light chain, and FIG. 12D represents the amino acid sequence encoded by the nucleotide sequence shown in FIG. 12C. The CDRs are underlined in FIG. 12D.

FIGS. 13A, 13B, 13C and 13D are a series of representations of the nucleotide sequence and amino acid sequences for the variable light and variable heavy regions of the huIFNγ antibody AD1.1R3P3_G9. FIG. 13A depicts the nucleotide sequence encoding the variable region of the heavy chain, and FIG. 13B represents the amino acid sequence encoded by the nucleotide sequence shown in FIG. 13A. The CDRs are underlined in FIG. 13B. FIG. 13C depicts the nucleotide sequence encoding the variable region of the light chain, and FIG. 13D represents the amino acid sequence encoded by the nucleotide sequence shown in FIG. 13C. The CDRs are underlined in FIG. 13D.

FIGS. 14A, 14B, 14C and 14D are a series of representations of the nucleotide sequence and amino acid sequences for the variable light and variable heavy regions of the huIFNγ antibody AD1.3R3P6_G10. FIG. 14A depicts the nucleotide sequence encoding the variable region of the heavy chain, and FIG. 14B represents the amino acid sequence encoded by the nucleotide sequence shown in FIG. 14A. The CDRs are underlined in FIG. 14B. FIG. 14C depicts the nucleotide sequence encoding the variable region of the light chain, and FIG. 14D represents the amino acid sequence encoded by the nucleotide sequence shown in FIG. 14C. The CDRs are underlined in FIG. 14D.

DETAILED DESCRIPTION

Figure 15:
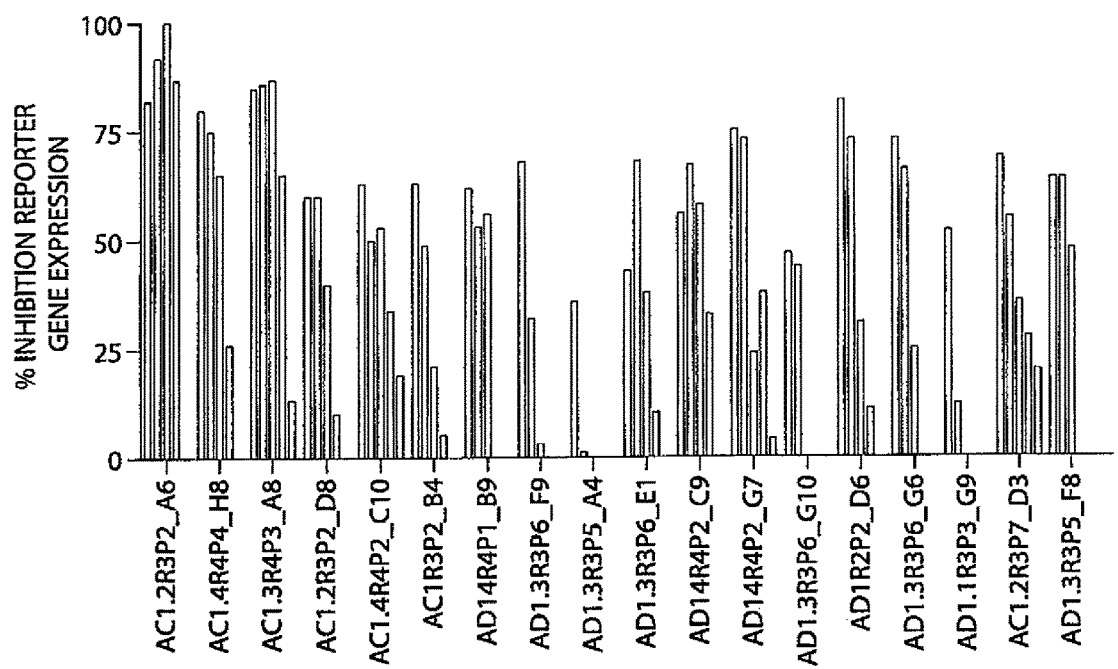
FIG. 15 is a graph depicting the inhibition of IFNγ-induced reporter gene expression using periplasmic scFv extracts. Quantified scFv extracts inhibited the IFNγ-induced reporter gene in a dose dependant fashion. For each scFv clone various concentrations (2.7, 0.68, 0.17, 0.043 and 0.011 nM) were tested as shown by the columns above each clone name (descending concentration from left to right, see also Table 3 below).
Figure 16:
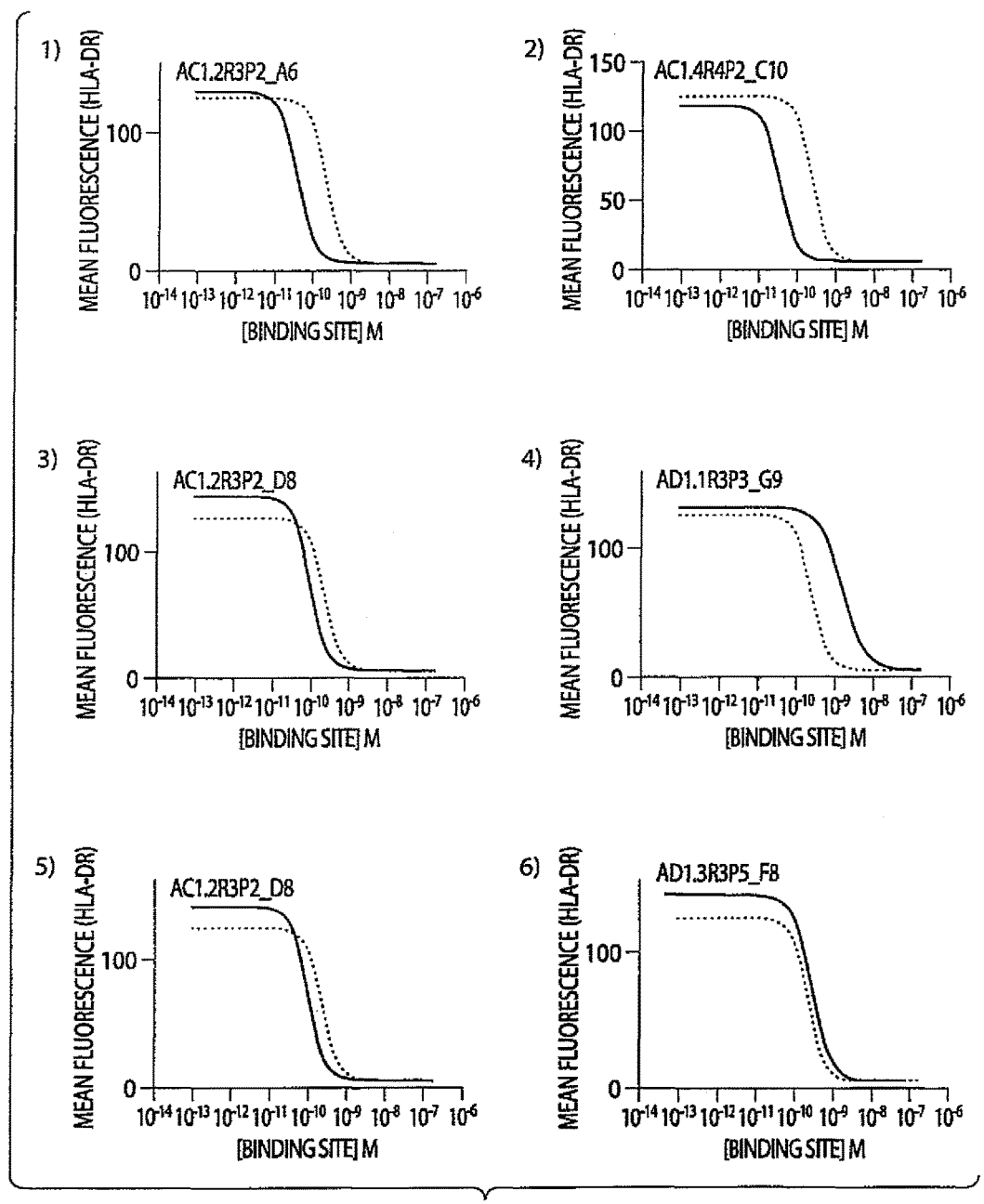
FIG. 16, Panels 1-12 are a series of graphs depicting the inhibition of IFNγ-induced MHC class II expression on melanoma cells using scFv extracts. Purified fully human scFv inhibited IFNγ-induced MHC II expression on melanoma cells. scFv clones (-) and the mouse anti-human IFNγ mAb 16C3 ( - - - ) are depicted.
Figure 16:
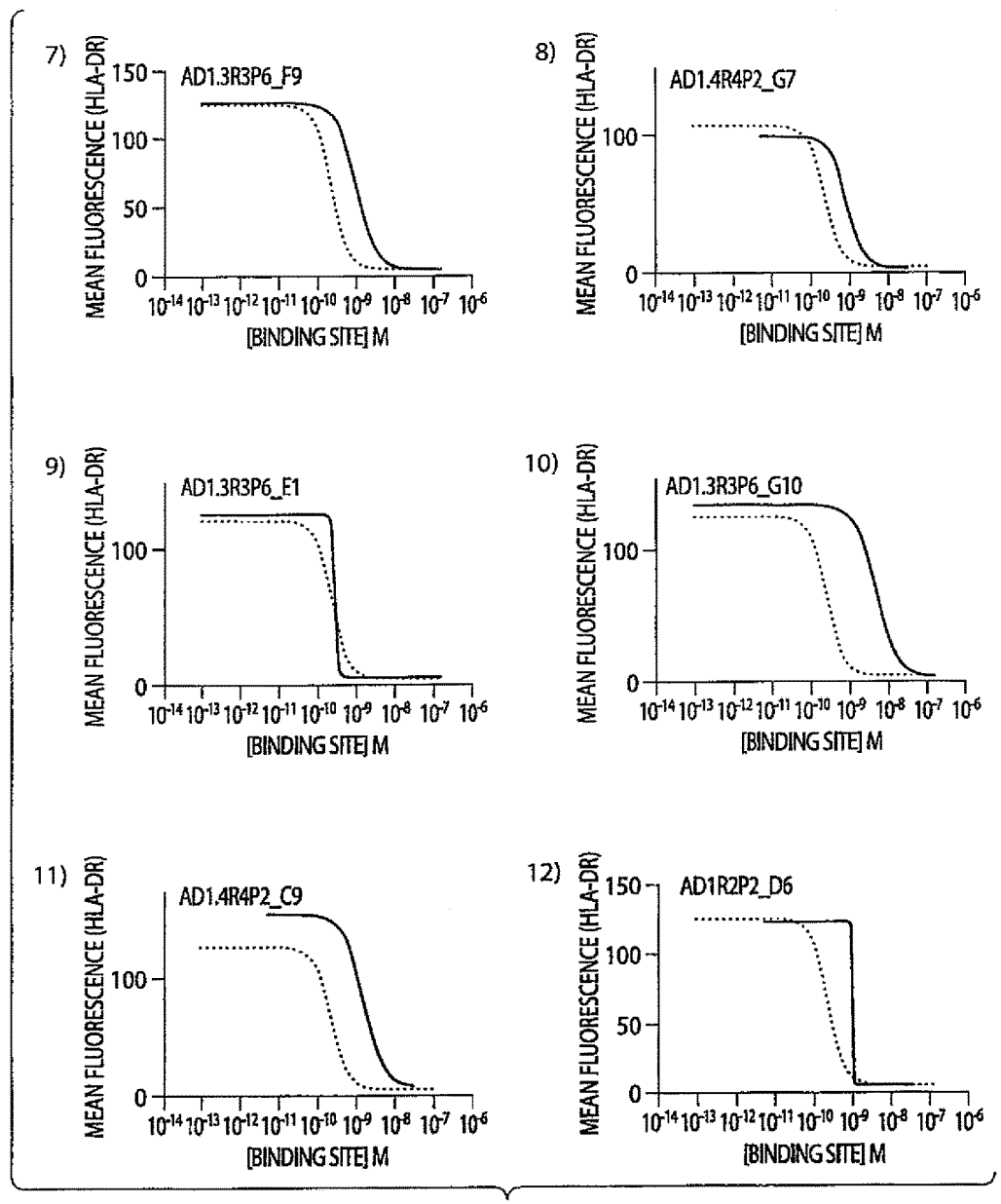
Figure 17:
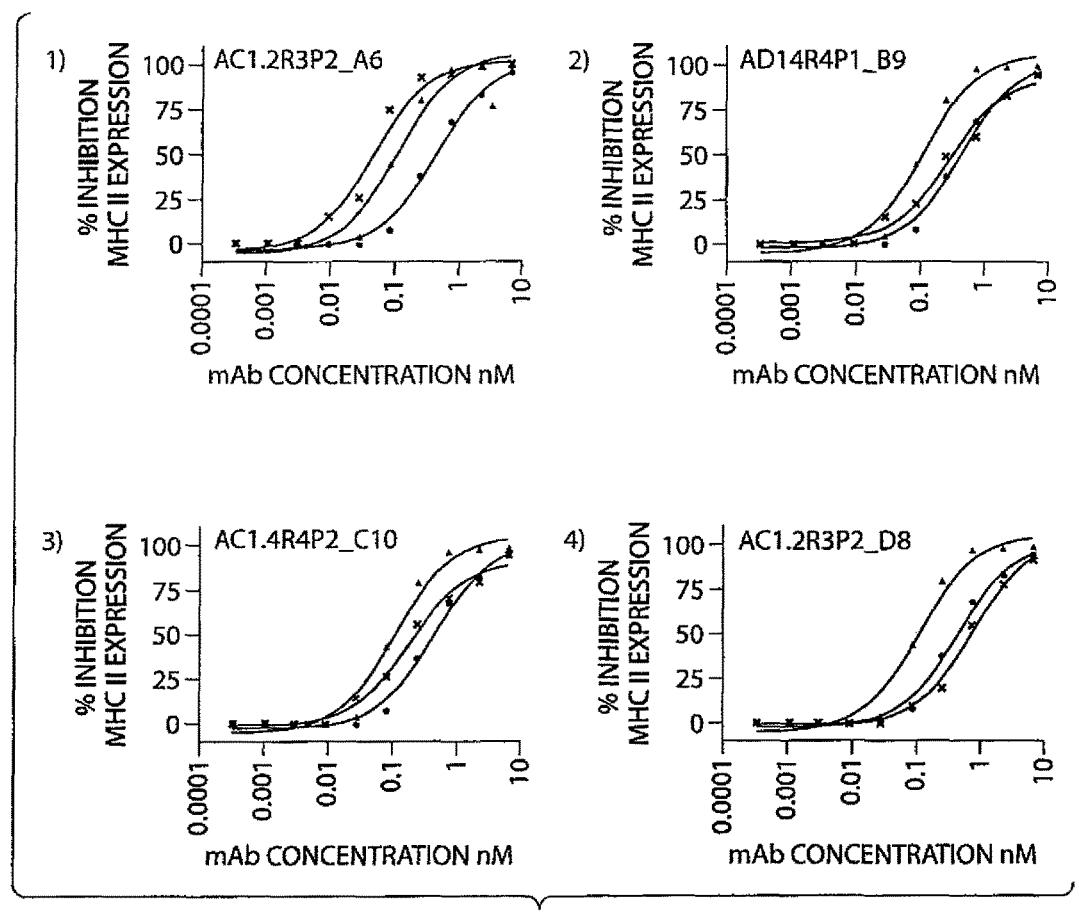
FIG. 17, Panels 1-7 are a series of graphs depicting the inhibition of IFNγ-induced MHC class II expression on melanoma cells using scFv extracts that were reformatted onto a fully human IgG backbone. Purified fully IgG mAbs inhibited IFNγ-induced MHC II expression on melanoma cells. Fully IgG clones (-x-), the mouse anti-human IFNγ mAb 16C3 (-▲-), and the R&D Systems, Inc. (Minneapolis, Minn.) mouse anti-human IFNγ MAB285 (-•-) are depicted.
Figure 17:
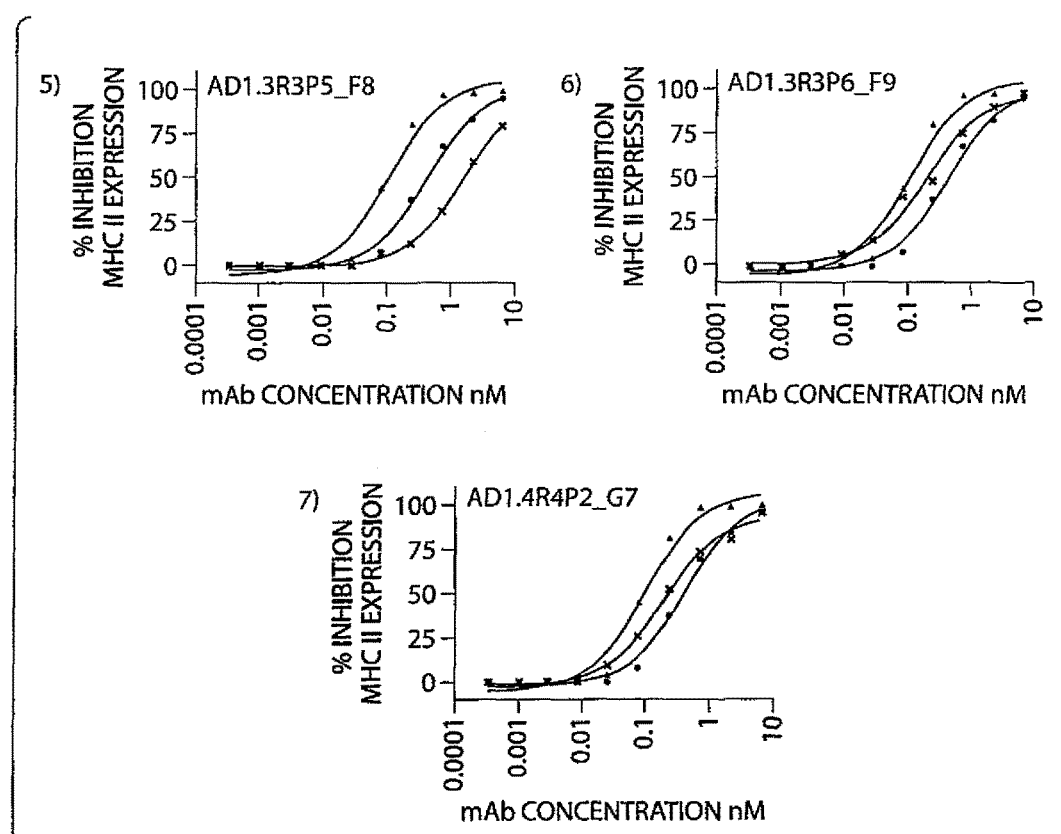

The present invention provides fully human monoclonal antibodies specific against interferon gamma (IFNγ). The antibodies are collectively referred to herein is huIFNγ antibodies.

The huIFNγ antibodies are, for example, IFNγ antagonists or inhibitors that modulate at least one biological activity of IFNγ. Biological activities of IFNγ include, for example, binding the IFNγ receptor (IFNγ-R), modulating, e.g., reducing or inhibiting, major histocompatibility complex (MHC) class II expression on a cell surface, and modulating, e.g., reducing or inhibiting, cell proliferation. For example, the huIFNγ antibodies completely or partially inhibit IFNγ activity by partially or completely blocking the binding of IFNγ and the IFNγ receptor (IFNγ-R). The IFNγ antibodies are considered to completely inhibit IFNγ activity when the level of IFNγ activity in the presence of the huIFNγ antibody is decreased by at least 95%, e.g., by 96%, 97%, 98%, 99% or 100% as compared to the level of IFNγ activity in the absence of binding with a huIFNγ antibody described herein. The IFNγ antibodies are considered to partially inhibit IFNγ activity when the level of IFNγ activity in the presence of the huIFNγ antibody is decreased by less than 95%, e.g., 10%, 20%, 25%, 30%, 40%, 50%, 60%, 75%, 80%, 85% or 90% as compared to the level of IFNγ activity in the absence of binding with a huIFNγ antibody described herein.

Additionally, the huIFNγ antibodies of the invention inhibit IFNγ-induced MHC class II expression on cells (see e.g., Examples 4 and 5). Preferably, the huIFNγ antibodies exhibit greater than 50% inhibition of IFNγ-induced MHC class II expression in the human melanoma cell line Me67.8 at a concentration of at least 0.02 nM. For example, the antibodies exhibit greater than 50% inhibition of IFNγ-induced MHC class II expression in the Me67.8 cell line at a concentration in the range of 0.022 nM to 0.044 nM, e.g., at a concentration of 0.022 nM, 0.028 nM or 0.044 nM.

The huIFNγ antibodies modulate an immune response in a subject, e.g., in a human subject. Preferably, the huIFNγ antibodies modulate an adaptive immune response in a subject. More preferably, the huIFNγ antibodies modulate the cellular or cell-mediated immune response, also known as Th1-type or Th1-mediated response.

For example, the huIFNγ antibodies described herein modulate, e.g., reduce, inhibit or prevent an exaggerated Th1-mediated immune response, such as an exaggerated Th1-mediated immune response associated with an autoimmune or inflammatory disorder such as, for example, Crohn's disease, system lupus erythematosus, psoriasis, sarcoidosis, rheumatoid arthritis, vasculitis, atopic dermatitis and secondary progressive multiple sclerosis. As used herein, the term "exaggerated" Th1-mediated immune response refers to the presence of an elevated level of Th1 cytokine(s), such as IL-2, IL-3, TNF-alpha (TNFα) and IFNγ, in a subject as compared to the level of Th1 cytokine production in a subject not suffering from a disease or disorder associated with an exaggerated Th1 immune response. To classify a Th1-mediated immune response as an exaggerated response, the level of a Th1 cytokine production response is evaluated, e.g., by measuring and analyzing the level of secreted cytokines using an ELISA or other assay.

The huIFNγ antibodies described herein modulate, e.g., inhibit, reduce or prevent, class switching to an IgG isotype, such as IFNγ-induced class switching. These huIFNγ antibodies modulate, e.g., inhibit, prevent or reduce a Th1-mediated response and consequently decrease IFNγ-induced switching.

The huIFNγ antibodies of the invention were produced by immunizing an animal with IFNγ, such as, for example, murine or human IFNγ (see e.g., Genbank Accession No. X13274) or an immunogenic fragment, derivative or variant thereof. Alternatively, the animal is immunized with cells transfected with a vector containing a nucleic acid molecule encoding IFNγ, such that IFNγ is expressed and associated with the surface of the transfected cells. Alternatively, the antibodies are obtained by screening a library that contains antibody or antigen binding domain sequences for binding to IFNγ. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

huIFNγ antibodies of the invention include, for example, the heavy chain complementarity determining regions (CDRs) shown below in Table 1, the light chain CDRs shown in Table 2, and combinations thereof.

TABLE 1

VH sequences from antibody clones that bind and neutralize IFNγ

| Clone Name | VH CDR1 | VH CDR2 | VH CDR3 |
| --- | --- | --- | --- |
| NI-0501 | SYAMS (SEQ ID NO: 3) | AISGSGGSTYYADSVKG (SEQ ID NO: 4) | DGSSGWYVPHWFDP (SEQ ID NO: 5) |
| AC1.2R2P2_A6 | SYAMS (SEQ ID NO: 3) | AISGSGGSTYYADSVKG (SEQ ID NO: 4) | DGSSGWYVPHWFDP (SEQ ID NO: 5) |
| AC1.2R3P2_D8 | SYAMS (SEQ ID NO: 3) | AISGSGGSTYYADSVKG (SEQ ID NO: 4) | DGSSGWYVPHWFDP (SEQ ID NO: 5) |
| AC1.4R4P2_C10 | SYAMS (SEQ ID NO: 3) | AISGSGGSTYYADSVKG (SEQ ID NO: 4) | DGSSGWYVPHWFDP (SEQ ID NO: 5) |
| AC1R3P2_B4 | SYAMS (SEQ ID NO: 3) | AISGSGGSTYYADSVKG (SEQ ID NO: 4) | DHSSGWYVISGMDV (SEQ ID NO: 13) |
| AD14R4P1_B9 | SYAMS (SEQ ID NO: 3) | AISGSGGSTYYADSVKG (SEQ ID NO: 4) | DLTVGGPWYYFDY (SEQ ID NO: 21) |
| AD1.3R3P5_F8 | SYAMS (SEQ ID NO: 3) | AISGSGGSTYYADSVKG (SEQ ID NO: 4) | VGSWYLEDFDI (SEQ ID NO: 69) |
| AD1.3R3P6_F9 | SYAMS (SEQ ID NO: 3) | AISGSGGSTYYADSVKG (SEQ ID NO: 4) | GGNYGDYFDYFDY (SEQ ID NO: 76) |
| AD1.3R3P6_E1 | SYAMS (SEQ ID NO: 3) | AISGSGGSTYYADSVKG (SEQ ID NO: 4) | RSFDSGGSFEY (SEQ ID NO: 64) |
| AD14R4P2_C9 | SYAMS (SEQ ID NO: 3) | AISGSGGSTYYADSVKG (SEQ ID NO: 4) | DGWNALGWLES (SEQ ID NO: 29) |
| AD14R4P2_G7 | SYAMS (SEQ ID NO: 3) | AISGSGGSTYYADSVKG (SEQ ID NO: 4) | DGWNALGWLES (SEQ ID NO: 29) |
| AD1.3R3P6_G10 | SYAMS (SEQ ID NO: 3) | AISGSGGSTYYADSVKG (SEQ ID NO: 4) | DGWNALGWLES (SEQ ID NO: 29) |
| AD1R2P2_D6 | SYAMS (SEQ ID NO: 3) | AISGSGGSTYYADSVKG (SEQ ID NO: 4) | DGWNALGWLES (SEQ ID NO: 29) |
| AD1.1R3P3_G9 | SYAMS (SEQ ID NO: 3) | AISGSGGSTYYADSVKG (SEQ ID NO: 4) | DFWVITSGNDY (SEQ ID NO: 89) |
| AC1.2R3P7_D3 | SNAMS (SEQ ID NO: 43) | TLTGSGGTAYYADSVEG (SEQ ID NO: 44) | GTELVGGGLDN (SEQ ID NO: 45) |

TABLE 2

VL sequences from antibody clones that bind and neutralize IFNγ

| Clone Name | VL CDR1 | VL CDR2 | VL CDR3 |
|---|---|---|---|
| NI-0501 | TRSSGSIASNYVQ (SEQ ID NO: 8) | EDNQRPS (SEQ ID NO: 9) | QSYDGSNRWM (SEQ ID NO: 10) |
| AC1.2R3P2_A6 | TRSSGSIV SNYVQ (SEQ ID NO: 106) | EDNRRPS (SEQ ID NO: 107) | QSYDGSNRWM (SEQ ID NO: 10) |
| AC1.2R3P2_D8 | TRSSGSIV SNYVQ (SEQ ID NO: 8) | EDNQRPS (SEQ ID NO: 17) | QSYDSNNFWV (SEQ ID NO: 61) |
| AC1.4R4P2_C10 | TRSSGTIASNYVQ (SEQ ID NO: 39) | EDNQRPS (SEQ ID NO: 17) | QSYDNSNHWV (SEQ ID NO: 40) |
| AC1R3P2_B4 | TRSSGSIASNYVQ (SEQ ID NO: 16) | EDNQRPS (SEQ ID NO: 17) | QSNDSDNVV (SEQ ID NO: 18) |
| AD14R4P1_B9 | TRSSGSIV SNYVQ (SEQ ID NO: 8) | DDDQRPS (SEQ ID NO: 25) | QSYDSSNVV (SEQ ID NO: 26) |
| AD1.3R3P5_F8 | TRSSGSIASNYVH (SEQ ID NO: 72) | EDNRRPS (SEQ ID NO: 9) | QSSDTTYHGGVV (SEQ ID NO: 73) |
| AD1.3R3P6_F9 | TRSSGSIASNYVQ (SEQ ID NO: 16) | EDNQRPS (SEQ ID NO: 17) | QSYEGF (SEQ ID NO: 79) |
| AD1.3R3P6_E1 | TRSSGYIASSYVQ (SEQ ID NO: 8) | EDDRRPS (SEQ ID NO: 25) | QSYDDTTPWV (SEQ ID NO: 26) |
| AD14R4P2_C9 | TRSGGSIGSYYVQ (SEQ ID NO: 32) | DDKKRPS (SEQ ID NO: 33) | QSYDSNNLVV (SEQ ID NO: 34) |
| AD14R4P2_G7 | TGRNGNIASNYVQ (SEQ ID NO: 84) | EDTQRPS (SEQ ID NO: 85) | QSSDSNRVL (SEQ ID NO: 86) |
| AD1.3R3P6_G10 | AGSSGSIASNYVQ (SEQ ID NO: 97) | EDNQRPS (SEQ ID NO: 17) | QSYSYNNQVV (SEQ ID NO: 98) |
| AD1R2P2_D6 | TGSSGSIASNYVQ (SEQ ID NO: 55) | EDNQRPS (SEQ ID NO: 17) | QSYDSSNQEVV (SEQ ID NO: 56) |
| AD1.1R3P3_G9 | TRSSGSIASNYVQ (SEQ ID NO: 16) | EDNRRPS (SEQ ID NO: 9) | QSFDSTNLVV (SEQ ID NO: 92) |
| AC1.2R3P7_D3 | TGSGGSIATNYVQ (SEQ ID NO: 48) | EDNQRPS (SEQ ID NO: 17) | QSYDSDNHHVV (SEQ ID NO: 49) |

An exemplary huIFNγ monoclonal antibody is the NI-0501 antibody described herein. The NI-0501 antibody is a back-mutated version of the AC1.2R3.P2_A6 antibody. As used herein, the term "back-mutated" refers to mutating a nucleotide or amino acid residue back to the nucleotide or residue found at the corresponding location in the germline sequence. The NI-0501 antibody includes a heavy chain variable region (SEQ ID NO:2) encoded by the nucleic acid sequence shown in SEQ ID NO:1, and a light chain variable region (SEQ ID NO:7) encoded by the nucleic acid sequence shown in SEQ ID NO:6 (FIGS. 1A-1D).

The amino acids encompassing the complementarity determining regions (CDR) as defined by Chothia et al. and E. A. Kabat et al. are underline in FIGS. 1B and 1D. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the A6 antibody have the following sequences: SYAMS (SEQ ID NO:3); AISGSGGSTYYADSVKG (SEQ ID NO:4); and DGSSGWYVPHWFDP (SEQ ID NO:5). The light chain CDRs of the A6 antibody have the following sequences: TRSSGSIASNYVQ (SEQ ID NO:8); EDNQRPS (SEQ ID NO:9); and QSYDGSNRWM (SEQ ID NO:10).

Another exemplary huIFNγ monoclonal antibody is the AC1.2R3.P2_A6 antibody ("A6") described herein. The A6 antibody includes a heavy chain variable region (SEQ ID NO:103) encoded by the nucleic acid sequence shown in SEQ ID NO:102, and a light chain variable region (SEQ ID NO:105) encoded by the nucleic acid sequence shown in SEQ ID NO:104 (FIGS. 1E-1H). The amino acids encompassing the complementarity determining regions (CDR) as defined by Chothia et al. and E. A. Kabat et al. are underline in FIGS. 1F and 1H. (See Chothia, C, et al., Nature 342: 877-883 (1989); Kabat, E A, et al., Sequences of Protein of immunological interest, Fifth Edition, US Department of Health and Human Services, US Government Printing Office (1991)). The heavy chain CDRs of the A6 antibody have the following sequences: SYAMS (SEQ ID NO:3); AISGSGGSTYYADSVKG (SEQ ID NO:4); and DGSSGWYVPHWFDP (SEQ ID NO:5). The light chain CDRs of the A6 antibody have the following sequences: TRSSGSIVSNYVQ (SEQ ID NO:106); EDNRRPS (SEQ ID NO:107); and QSYDGSNRWM (SEQ ID NO:10).

The AC1.2R3P2_B4 antibody (also referred to herein as "B4") includes a heavy chain variable region (SEQ ID NO:12) encoded by the nucleic acid sequence shown in SEQ ID NO:11, and a light chain variable region (SEQ ID NO:15)

encoded by the nucleic acid sequence shown in SEQ ID NO:14 (FIGS. 2A-2D). The amino acids encompassing the CDR as defined by Chothia et al. 1989, E. A. Kabat et al., 1991 are underlined in FIGS. 2B and 2D. The heavy chain CDRs of the B4 antibody have the following sequences: SYAMS (SEQ ID NO:3); AISGSGGSTYYADSVKG (SEQ ID NO:4); and DHSSGWYVISGMDV (SEQ ID NO:13). The light chain CDRs of the B4 antibody have the following sequences: TRSSGSIASNYVQ (SEQ ID NO:16); EDNQRPS (SEQ ID NO:17); and QSNDSDNVV (SEQ ID NO:18).

The AD1.4R4P1_B9 antibody (also referred to herein as "B9") includes a heavy chain variable region (SEQ ID NO:20) encoded by the nucleic acid sequence shown in SEQ ID NO:19, and a light chain variable region (SEQ ID NO:23) encoded by the nucleic acid sequence shown in SEQ ID NO:22 (FIGS. 3A-3D). The amino acids encompassing the CDR as defined by Chothia et al. 1989, E. A. Kabat et al., 1991 are underlined in FIGS. 3B and 3D. The heavy chain CDRs of the B9 antibody have the following sequences: SYAMS (SEQ ID NO:3); AISGSGGSTYYADSVKG (SEQ ID NO:4); and DLTVGGPWYYFDY (SEQ ID NO:21). The light chain CDRs of the B9 antibody have the following sequences: TRSSGSIVSNYVQ (SEQ ID NO:8); DDDQRPS (SEQ ID NO:25); and QSYDSSNVV (SEQ ID NO:26).

The AD1.4R4P2_C9 antibody (also referred to herein as "C9") includes a heavy chain variable region (SEQ ID NO:28) encoded by the nucleic acid sequence shown in SEQ ID NO:27, and a light chain variable region (SEQ ID NO:31) encoded by the nucleic acid sequence shown in SEQ ID NO:30 (FIGS. 4A-4D). The amino acids encompassing the CDR as defined by Chothia et al. 1989, E. A. Kabat et al., 1991 are underlined in FIGS. 4B and 4D. The heavy chain CDRs of the C9 antibody have the following sequences: SYAMS (SEQ ID NO:3); AISGSGGSTYYADSVKG (SEQ ID NO:4); and DGWNALGWLES (SEQ ID NO:29). The light chain CDRs of the C9 antibody have the following sequences: TRSGGSIGSYYVQ (SEQ ID NO:32); DDKKRPS (SEQ ID NO:33); and QSYDSNNLVV (SEQ ID NO:34).

The AC1.4R4P2_C10 antibody (also referred to herein as "C10") includes a heavy chain variable region (SEQ ID NO:36) encoded by the nucleic acid sequence shown in SEQ ID NO:35, and a light chain variable region (SEQ ID NO:38) encoded by the nucleic acid sequence shown in SEQ ID NO:37 (FIGS. 5A-5D). The amino acids encompassing the CDR as defined by Chothia et al. 1989, E. A. Kabat et al., 1991 are underlined in FIGS. 5B and 5D. The heavy chain CDRs of the C10 antibody have the following sequences: SYAMS (SEQ ID NO:3); AISGSGGSTYYADSVKG (SEQ ID NO:4); and DGSSGWYVPHWF DP (SEQ ID NO:5). The light chain CDRs of the C10 antibody have the following sequences: TRSSGTIASNYVQ (SEQ ID NO:39); EDNQRPS (SEQ ID NO:17); and QSYDNSNHWV (SEQ ID NO:40).

The AC1.2R3P7_D3 antibody (also referred to herein as "D3") includes a heavy chain variable region (SEQ ID NO:42) encoded by the nucleic acid sequence shown in SEQ ID NO:41, and a light chain variable region (SEQ ID NO:47) encoded by the nucleic acid sequence shown in SEQ ID NO:46 (FIGS. 6A-6D). The amino acids encompassing the CDR as defined by Chothia et al. 1989, E. A. Kabat et al., 1991 are underlined in FIGS. 6B and 6D. The heavy chain CDRs of the D3 antibody have the following sequences: SNAMS (SEQ ID NO:43); TLTGSGGTAYYADSVEG (SEQ ID NO:44); and GTELVGGGLDN (SEQ ID NO:45). The light chain CDRs of the D3 antibody have the following sequences: TGSGGSIATNYVQ (SEQ ID NO:48); EDNQRPS (SEQ ID NO:17) and QSYDSDNHHVV (SEQ ID NO:49).

The AD1.2R2P2 D6 antibody (also referred to herein as "D6") includes a heavy chain variable region (SEQ ID NO:51) encoded by the nucleic acid sequence shown in SEQ ID NO:50, and a light chain variable region (SEQ ID NO:54) encoded by the nucleic acid sequence shown in SEQ ID NO:53 (FIGS. 7A-7D). The amino acids encompassing the CDR as defined by Chothia et al. 1989, E. A. Kabat et al., 1991 are underlined in FIGS. 7B and 7D. The heavy chain CDRs of the D6 antibody have the following sequences: SYAMS (SEQ ID NO:3); AISGSGGSTYYADSVKG (SEQ ID NO:4); and DGWNALGWLES (SEQ ID NO:29). The light chain CDRs of the D6 antibody have the following sequences: TGSSGSIASNYVQ (SEQ ID NO:55); EDNQRPS (SEQ ID NO:17); and QSYDSSNQEVV (SEQ ID NO:56).

The AC1.2R2P2_D8 antibody (also referred to herein as "D8") includes a heavy chain variable region (SEQ ID NO:58) encoded by the nucleic acid sequence shown in SEQ ID NO:57, and a light chain variable region (SEQ ID NO:60) encoded by the nucleic acid sequence shown in SEQ ID NO:59 (FIGS. 8A-8D). The amino acids encompassing the CDR as defined by Chothia et al. 1989, E. A. Kabat et al., 1991 are underlined in FIGS. 8B and 8D. The heavy chain CDRs of the D8 antibody have the following sequences: SYAMS (SEQ ID NO:3); AISGSGGSTYYADSVKG (SEQ ID NO:4); and DGSSGWYVPHWF DP (SEQ ID NO:5). The light chain CDRs of the D8 antibody have the following sequences: TRSSGSIVSNYVQ (SEQ ID NO:8); EDNQRPS (SEQ ID NO:17); and QSYDSNNFWV (SEQ ID NO:61).

The AD1.3R3P6_E1 antibody (also referred to herein as "E1") includes a heavy chain variable region (SEQ ID NO:63) encoded by the nucleic acid sequence shown in SEQ ID NO:62, and a light chain variable region (SEQ ID NO:66) encoded by the nucleic acid sequence shown in SEQ ID NO:65 (FIGS. 9A-9D). The amino acids encompassing the CDR as defined by Chothia et al. 1989, E. A. Kabat et al., 1991 are underlined in FIGS. 9B and 9D. The heavy chain CDRs of the E1 antibody have the following sequences: SYAMS (SEQ ID NO:3); AISGSGGSTYYADSVKG (SEQ ID NO:4); and RSFDSGGSFEY (SEQ ID NO:64). The light chain CDRs of the E1 antibody have the following sequences: TRSSGSIVSNYVQ (SEQ ID NO:8); DDDQRPS (SEQ ID NO:25); and QSYDSSNVV (SEQ ID NO:26).

The AD1.3R3P5_F8 antibody (also referred to herein as "F8") includes a heavy chain variable region (SEQ ID NO:68) encoded by the nucleic acid sequence shown in SEQ ID NO:67, and a light chain variable region (SEQ ID NO:71) encoded by the nucleic acid sequence shown in SEQ ID NO:70 (FIGS. 10A-10D). The amino acids encompassing the CDR as defined by Chothia et al. 1989, E. A. Kabat et al., 1991 are underlined in FIGS. 10B and 10D. The heavy chain CDRs of the F8 antibody have the following sequences: SYAMS (SEQ ID NO:3); AISGSGGSTYYADSVKG (SEQ ID NO:4); and VGSWYLEDFDI (SEQ ID NO:69). The light chain CDRs of the F8 antibody have the following sequences: TRSSGSIASNYVH (SEQ ID NO:72); EDNRRPS (SEQ ID NO:9); and QSSDTTYHGGVV (SEQ ID NO:73).

The AD1.3R3P6_F9 antibody (also referred to herein as "F9") includes a heavy chain variable region (SEQ ID NO:75) encoded by the nucleic acid sequence shown in SEQ ID NO:74, and a light chain variable region (SEQ ID NO:78) encoded by the nucleic acid sequence shown in SEQ ID NO:77 (FIGS. 11A-11D). The amino acids encompassing the CDR as defined by Chothia et al. 1989, E. A. Kabat et al., 1991 are underlined in FIGS. 11B and 11D. The heavy chain CDRs of the F9 antibody have the following sequences: SYAMS (SEQ ID NO:3); AISGSGGSTYYADS-VKG (SEQ ID NO:4); and GGNYGDYFDYFDY (SEQ ID NO:76). The light chain CDRs of the F9 antibody have the following sequences: TRSSGSIASNYVQ (SEQ ID NO:16); EDNQRPS (SEQ ID NO:17); and QSYEGF (SEQ ID NO:79).

The AD1.4R4P2_G7 antibody (also referred to herein as "G7") includes a heavy chain variable region (SEQ ID NO:81) encoded by the nucleic acid sequence shown in SEQ ID NO:80, and a light chain variable region (SEQ ID NO:83) encoded by the nucleic acid sequence shown in SEQ ID NO:82 (FIGS. 12A-12D). The amino acids encompassing the CDR as defined by Chothia et al. 1989, E. A. Kabat et al., 1991 are underlined in FIGS. 12B and 12D. The heavy chain CDRs of the G7 antibody have the following sequences: SYAMS (SEQ ID NO:3); AISGSGGSTYYADS-VKG (SEQ ID NO:4); and DGWNALGWLES (SEQ ID NO:29). The light chain CDRs of the G7 antibody have the following sequences: TGRNGNIASNYVQ (SEQ ID NO:84); EDTQRPS (SEQ ID NO:85); and QSSDSNRVL (SEQ ID NO:86).

The AD1.1R3P3_G9 antibody (also referred to herein as "G9") includes a heavy chain variable region (SEQ ID NO:88) encoded by the nucleic acid sequence shown in SEQ ID NO:87, and a light chain variable region (SEQ ID NO:91) encoded by the nucleic acid sequence shown in SEQ ID NO:90 (FIGS. 13A-13D). The amino acids encompassing the CDR as defined by Chothia et al. 1989, E. A. Kabat et al., 1991 are underlined in FIGS. 13B and 13D. The heavy chain CDRs of the G9 antibody have the following sequences: SYAMS (SEQ ID NO:3); AISGSGGSTYYADS-VKG (SEQ ID NO:4); and DFWVITSGNDY (SEQ ID NO:89). The light chain CDRs of the G9 antibody have the following sequences: TRSSGSIASNYVQ (SEQ ID NO:16); EDNRRPS (SEQ ID NO:9); and QSFDSTNLVV (SEQ ID NO:92).

The AD1.3R3P6_G10 antibody (also referred to herein as "G10") includes a heavy chain variable region (SEQ ID NO:94) encoded by the nucleic acid sequence shown in SEQ ID NO:93, and a light chain variable region (SEQ ID NO:96) encoded by the nucleic acid sequence shown in SEQ ID NO:95 (FIGS. 14A-14D). The amino acids encompassing the CDR as defined by Chothia et al. 1989, E. A. Kabat et al., 1991 are underlined in FIGS. 14B and 14D. The heavy chain CDRs of the G10 antibody have the following sequences: SYAMS (SEQ ID NO:3); AISGSGGSTYYADS-VKG (SEQ ID NO:4); and DGWNALGWLES (SEQ ID NO:29). The light chain CDRs of the G10 antibody have the following sequences: AGSSGSIASNYVQ (SEQ ID NO:97); EDNQRPS (SEQ ID NO:17); and QSYSYN-NQVV (SEQ ID NO:98).

huIFNγ antibodies of the invention also include antibodies that include a heavy chain variable amino acid sequence that is at least 90%, 92%, 95%, 97% 98%, 99% or more identical the amino acid sequence of SEQ ID NO: 2, 12, 20, 28, 36, 42, 51, 58, 63, 68, 75, 81, 88, 94, or 103 (FIGS. 1-14) and/or a light chain variable amino acid that is at least 90%, 92%, 95%, 97% 98%, 99% or more identical the amino acid sequence of SEQ ID NO: 7, 15, 23, 31, 38, 47, 54, 60, 66, 71, 78, 83, 91, 96 or 105 (FIGS. 1-14).

Alternatively, the monoclonal antibody is an antibody that binds to the same epitope as NI-0501, A6, B4, B9, C9, C10, D3, D6, D8, E1, F8, F9, G7, G9 or G10.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ μM; preferably $\leq 100$ nM and most preferably $\leq 10$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an IFNγ epitope when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

Those skilled in the art will recognize that it is possible to determine, without undue experimentation, if a human monoclonal antibody has the same specificity as a human monoclonal antibody of the invention (e.g., monoclonal antibody NI-0501, A6, B4, B9, C9, C10, D3, D6, D8, E1, F8, F9, G7, G9 or G10) by ascertaining whether the former prevents the latter from binding to a IFNγ antigen polypeptide. If the human monoclonal antibody being tested competes with a human monoclonal antibody of the invention, as shown by a decrease in binding by the human monoclonal antibody of the invention, then the two monoclonal antibodies bind to the same, or a closely related, epitope. Another way to determine whether a human monoclonal antibody has the specificity of a human monoclonal antibody of the invention is to pre-incubate the human monoclonal antibody of the invention with the IFNγ antigen polypeptide with which it is normally reactive, and then add the human monoclonal antibody being tested to determine if the human monoclonal antibody being tested is inhibited in its ability to bind the IFNγ antigen polypeptide. If the human monoclonal antibody being tested is inhibited then, in all likelihood, it has the same, or functionally equivalent, epitopic specificity as the monoclonal antibody of the invention.

Various procedures known within the art are used for the production of the monoclonal antibodies directed against a protein such as an IFNγ protein, or against derivatives, fragments, analogs homologs or orthologs thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described in the Examples provided below. Human monoclonal antibodies can be also prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

It is desirable to modify the antibody of the invention with respect to effector function, so as to enhance, e.g., the effectiveness of the antibody in treating immune-related diseases. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also includes $F_v$, $F_{ab}$, $F_{ab'}$ and $F_{(ab')2}$ huIFNγ fragments, single chain huIFNγ antibodies, bispecific huIFNγ antibodies and heteroconjugate huIFNγ antibodies.

Bispecific antibodies are antibodies that have binding specificities for at least two different antigens. In the present case, one of the binding specificities is for IFNγ. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, IFNγ, CD28, or B7), or Fc receptors for IgG (FcγR), such as FcγRI (CD64), FcγRII (IFNγ2) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radio conjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling is accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding is achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Preferred polypeptides in accordance with the invention comprise the human heavy chain immunoglobulin molecules represented by FIGS. 1B, 2B, 3B and 4B and the human light chain immunoglobulin molecules represented by FIGS. 1D, 2D, 3D and 4D, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or anti-sense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end the lefthand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxyterminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to IFNγ, under suitable binding conditions, (2) ability to block appropriate IFNγ binding, or (3) ability to inhibit IFNγ-expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects. The term subject includes humans and other mammals.

Human Antibodies and Humanization of Antibodies

A huIFNγ antibody is generated, for example, using the procedures described in the Examples provided below. An IgG huIFNγ antibody is generated, for example, by converting a scFv clone an IgG format (see e.g., Example 6). Alternatively, such a huIFNγ antibody is developed, for example, using phase-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of IFNγ or fragments thereof.

A huIFNγ antibody is produced by a process wherein at least one step of the process includes immunizing a transgenic, non-human animal with human IFNγ protein. Some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and U.S. Pat. No. 6,150,584. By one strategy, the xenogeneic (human) heavy and light chain immunoglobulin genes are introduced into the host germ line (e.g., sperm or oocytes) and, in separate steps, the corresponding host genes are rendered non-functional by inactivation using homologous recombination. Human heavy and light chain immunoglobulin genes are reconstructed in an appropriate eukaryotic or prokaryotic microorganism, and the resulting DNA fragments are introduced into the appropriate host, for example, the pronuclei of fertilized mouse oocytes or embryonic stem cells. Inactivation of the endogenous host immunoglobulin loci is achieved by targeted disruption of the appropriate loci by homologous recombination in the host cells, particularly embryonic stem cells or pronuclei of fertilized mouse oocytes. The targeted disruption can involve introduction of a lesion or deletion in the target locus, or deletion within the target locus accompanied by insertion into the locus, e.g., insertion of a selectable marker. In the case of embryonic stem cells, chimeric animals are generated which are derived in part from the modified embryonic stem cells and are capable of transmitting the genetic modifications through the germ line. The mating of hosts with introduced human immunoglobulin loci to strains with inactivated endogenous loci will yield animals whose antibody production is purely xenogeneic, e.g., human.

In an alternative strategy, at least portions of the human heavy and light chain immunoglobulin loci are used to replace directly the corresponding endogenous immunoglobulin loci by homologous recombination in embryonic stem cells. This results in simultaneous inactivation and replacement of the endogenous immunoglobulin. This is followed by the generation of chimeric animals in which the embryonic stem cell-derived cells can contribute to the germ lines.

For example, a B cell clone that expresses human anti-IFNγ antibody is removed from the xenogenic non-human animal and immortalized according to various methods known within the art. Such B cells may be derived directly from the blood of the animal or from lymphoid tissues, including but not restricted to spleen, tonsils, lymph nodes, and bone marrow. The resultant, immortalized B cells may be expanded and cultured in vitro to produce large, clinically applicable quantities of huIFNγ antibody. Alternatively, genes encoding the immunoglobulins with one or more human variable regions can be recovered and expressed in a differing cell type, including but not restricted to a mammalian cell culture system, in order to obtain the antibodies directly or individual chains thereof, composed of single chain $F_v$ molecules.

In addition, the entire set of fully human anti-IFNγ antibodies generated by the xenogenic non-human animal may be screened to identify one such clone with the optimal characteristics. Such characteristics include, for example, binding affinity to the human IFNγ protein, stability of the interaction as well as the isotype of the fully human anti-IFNγ antibody. Clones from the entire set which have the desired characteristics then are used as a source of nucleotide sequences encoding the desired variable regions, for further manipulation to generate antibodies with the-se characteristics, in alternative cell systems, using conventional recombinant or transgenic techniques.

This general strategy was demonstrated in connection with generation of the first XenoMouse™ strains as published in 1994. See Green et al. Nature Genetics 7:13-21 (1994). This approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464, 584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med.: 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000.

In an alternative approach, others have utilized a "minilocus" approach. In the minilocus approach, an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877, 397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996).

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against IFNγ in order to vitiate concerns and/or effects of HAMA or HACA response.

The production of antibodies with reduced immunogenicity is also accomplished via humanization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as priers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL-31 sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau PEAS USA 94:4937-4942 (1997) (ribosomal display), Parmley and Smith Gene 73:305-318 (1988) (phage display), Scott TIB5 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to IFNγ expressing cells, IFNγ itself, forms of IFNγ, epitopes or peptides thereof, and expression libraries thereto (See e.g., U.S. Pat. No. 5,703,057) which can thereafter be screened as described above for the activities described above.

Design and Generation of Other Therapeutics

In accordance with the present invention and based on the activity of the antibodies that are produced and characterized herein with respect to IFNγ, the design of other therapeutic modalities beyond antibody moieties is facilitated. Such modalities include, without limitation, advanced antibody therapeutics, such as bispecific antibodies, immunotoxins, and radio labeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to IFNγ and another to a second molecule that are conjugated together, (ii) a single antibody that has one chain specific to IFNγ and a second chain specific to a second molecule, or (iii) a single chain antibody that has specificity to IFNγ and the other molecule. Such bispecific antibodies are generated using techniques that are well known for example, in connection with (i) and (ii) See e.g., Fanger et al. Immunol Methods 4:72-81 (1994) and Wright and Harris, supra, and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing IFNγ, and particularly those cells in which the antibodies of the invention are effective.

In connection with the generation of therapeutic peptides, through the utilization of structural information related to IFNγ and antibodies thereto, such as the antibodies of the invention or screening of peptide libraries, therapeutic peptides can be generated that are directed against IFNγ. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the IFNγ molecule (or a form, such as a splice variant or alternate form) is functionally active in a disease process, it will also be possible to design gene and antisense therapeutics thereto through conventional techniques. Such modalities can be utilized for modulating the function of IFNγ. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the IFNγ molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IFNγ. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oilin-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a huIFNγ antibody of the invention, are used to treat or alleviate a symptom associated with an immune-related disorder, such as, for example, an autoimmune disease or an inflammatory disorder.

For example, administering a huIFNγ antibody to a subject suffering from Crohn's Disease (CD) can act directly on the disease-causing immune cells, thereby providing rapid intervention with minimal suppression of the immune system. Administering a huIFNγ antibody to a subject suffering from Systemic Lupus Erythematosus is another medical indication that provides an opportunity to modify the immune cells responsible for the disease. Administering an huIFNγ antibody, a fully human protein, to a subject suffering from psoriasis avoids the need to treat patients with more aggressive medications (e.g., Methotrexate) that have well documented unwanted side effects (e.g., liver damage). Administering a huIFNγ antibody to a subject suffering from rheumatoid arthritis is another medical indication that provides the opportunity to modulate the upstream generation and function of disease-inducing Th1-mediated response.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The huIFNγ antibodies modulate an immune response in a subject, e.g., in a human subject. For example, the huIFNγ antibodies described herein modulate, e.g., reduce, inhibit or prevent an exaggerated Th1-mediated immune response, such as an exaggerated Th1-mediated immune response associated with an autoimmune or inflammatory disorder such as, for example, Crohn's disease, system lupus erythematosus, psoriasis, sarcoidosis, rheumatoid arthritis, vasculitis, atopic dermatitis and secondary progressive multiple sclerosis. In an exaggerated Th1-mediated immune response, Th1 cytokine(s), such as IL-2, IL-3, TNF-alpha (TNFα) and IFNγ, are presented in a subject at level that is higher than the level of Th1 cytokine production in a subject not suffering from a disease or disorder associated with an exaggerated Th-1 immune response. To classify a Th1-mediated immune response as an exaggerated response, the level of a Th1 cytokine production response is evaluated, e.g., by measuring and analyzing the level of secreted cytokines using an ELISA or other assay.

The huIFNγ antibodies described herein are also used to modulate, e.g., inhibit, reduce or prevent, class switching to an IgG isotype, such as IFNγ-induced class switching. These huIFNγ antibodies modulate, e.g., inhibit, prevent or reduce a Th1-mediated response and consequently decrease IFNγ-induced switching.

In one embodiment, the huIFNγ antibody compositions used to treat an immune-related disorder are administered in combination with any of a variety of anti-cytokine agents or anti-chemokine agents. Suitable anti-cytokine or anti-chemokine reagents recognize, for example, cytokines such as interleukin 1 (IL-1), IL-2, IL-4, IL-6, IL-12, IL-13, IL-15, IL-17, IL-18, IL-20, IL-21, IL-22, IL-23, IL-27 and IL-31, and/or chemokines such as MIP1 alpha, MIP1 beta, RANTES, MCP1, IP-10, ITAC, MIG, SDF and fractalkine.

The present invention also provides methods of treating or alleviating a symptom associated with an immune-related disorder. For example, the compositions of the invention are used to treat or alleviate a symptom of any of the autoimmune diseases and inflammatory disorders described herein. Symptoms associated with immune-related disorders include, for example, inflammation, fever, loss of appetite, weight loss, abdominal symptoms such as, for example, abdominal pain, diarrhea or constipation, joint pain or aches (arthralgia), fatigue, rash, anemia, extreme sensitivity to cold (Raynaud's phenomenon), muscle weakness, muscle fatigue, changes in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

The therapeutic formulations of huIFNγ antibody are administered to a subject suffering from an immune-related disorder, such as an autoimmune disease or an inflammatory disorder. A subject suffering from an autoimmune disease or an inflammatory disorder is identified by methods known in the art. For example, subjects suffering from an autoimmune disease such as Crohn's disease, lupus or psoriasis, are identified using any of a variety of clinical and/or laboratory tests such as, physical examination, radiologic examination and blood, urine and stool analysis to evaluate immune status. For example, patients suffering from lupus are identified, e.g., by using the anti-nuclear antibody test (ANA) to determine if auto-antibodies to cell nuclei are present in the blood. Patients suffering from Crohn's are identified, e.g., using an upper gastrointestinal (GI) series and/or a colonoscopy to evaluate the small and large intestines, respectively. Patients suffering from psoriasis are identified, e.g., using microscopic examination of tissue taken from the affected skin patch, while patients suffering from rheumatoid arthritis are identified using, e.g., blood tests and/or x-ray or other imaging evaluation.

Administration of a huIFNγ antibody to a patient suffering from an immune-related disorder such as an autoimmune disease or an inflammatory disorder if any of a variety of laboratory or clinical results is achieved. For example, administration of a huIFNγ antibody to a patient suffering from an immune-related disorder such as an autoimmune disease or an inflammatory disorder is considered successful one or more of the symptoms associated with the disorder is alleviated, reduced, inhibited or does not progress to a further, i.e., worse, state. Administration of a huIFNγ antibody to a patient suffering from an immune-related disorder such as an autoimmune disease or an inflammatory disorder is considered successful if the disorder, e.g., an autoimmune disorder, enters remission or does not progress to a further, i.e., worse, state.

Diagnostic and Prophylactic Formulations

The fully human anti-IFNγ MAbs of the invention are used in diagnostic and prophylactic formulations. In one embodiment, a huIFNγ MAb of the invention is administered to patients that are at risk of developing one of the aforementioned autoimmune diseases. A patient's predisposition to one or more of the aforementioned autoimmune diseases can be determined using genotypic, serological or biochemical markers.

In another embodiment of the invention, a huIFNγ antibody is administered to human individuals diagnosed with one or more of the aforementioned autoimmune diseases. Upon diagnosis, a huIFNγ antibody is administered to mitigate or reverse the effects of autoimmunity.

Antibodies of the invention are also useful in the detection of IFNγ in patient samples and accordingly are useful as diagnostics. For example, the huIFNγ antibodies of the invention are used in in vitro assays, e.g., ELISA, to detect IFNγ levels in a patient sample.

In one embodiment, a huIFNγ antibody of the invention is immobilized on a solid support (e.g., the well(s) of a microtiter plate). The immobilized antibody serves as a capture antibody for any IFNγ that may be present in a test sample. Prior to contacting the immobilized antibody with a patient sample, the solid support is rinsed and treated with a blocking agent such as mink protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IFNγ antigen in the test sample is determined by comparison with a standard curve developed from the standard samples.

It will be appreciated that based on the results obtained using the huIFNγ antibodies of the invention in an in vitro diagnostic assay, it is possible to stage a disease (e.g., an autoimmune or inflammatory disorder) in a subject based on expression levels of the IFNγ antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1: Cloning, Expression and Purification of Human Interferon Gamma

Cloning

The sequence corresponding to the mature sequence of human interferon gamma (hIFNγ, huIFNγ) was amplified from human cDNA by polymerase chain reaction (PCR) using specific oligonucleotides. The amplification production was gel-purified and cloned into the pET41c expression vector (Novagen, San Diego Calif.). The vector was further modified to introduce an Avitag™ (Avidity, Denver Colo.) and an octa-histidine tag at the C-terminus of hIFNγ allowing for in vivo biotinylation of the protein and purification by IMAC (Immobilized Metal Ion Affinity Chromatography).

Expression.

E. coli BL21 cells were co-transformed with the pET41c-hIFNγ and a pACYC184-BirA vector, which encodes the BirA enzyme required for the in vivo biotinylation of the Avitag™ sequence. Single colonies resistant to Kanamycin (50 μg/ml) and Chloramphenicol (10 μg/ml) were selected and used to inoculate a starter culture in LB (Kan 50 μg/ml/Cm 10 μg/ml) and grown overnight at 37° C.

The next day, the culture was used to inoculate (1:100 dilution) a 400 ml culture of LB (Kan 50 μg/ml/Cm 10 μg/ml) supplemented with 50 μM biotin. The culture was grown at 37° C. with shaking (240 rpm) until an $OD_{600}$ of 0.6 was reached. At that point, isopropyl-beta-D-thiogalactopyranoside (IPTG) was added to a final concentration of 1 mM, and the culture was further incubated for 3 h under the same conditions. Cells were centrifuged at 4000 rpm for 20 minutes, and the pellet was frozen at −20° C. Under these conditions essentially all of the hIFNγ was insoluble and found in inclusion bodies.

Purification.

Bacterial pellets were thawed and resuspended in 8 ml of Bugbuster reagent containing 8 μl of Benzonaze (Novagen) and incubated at room temperature for 30 minutes. The solution was centrifuged for 30 minutes at 15'000 g at 4° C. The pellet containing the inclusion bodies was resuspended in 7 ml of solubilization buffer (50 mM Tris-HCL pH 7.4, 300 mM NaCl, 20 mM Imidazole, 5 mM β-mercaptoethanol, 6M Guanidin-HCl). The resuspended material was centrifuged at 4° C. for 30 minutes at 15'000 g.

Two 5 ml Hi Trap Chelating column (Amersham, Buckinghamshire, England), loaded with $NiSO_4$ and equilibrated with solubilization buffer, were connected together according to manufacturer's instructions. The supernatant after the centrifugation step was filter on a 0.45 μm membrane and loaded on the column with the help of peristaltic pump at 1 ml/min. The columns were then placed on an AKTA prime chromatography system for on column protein refolding and elution. The immobilized protein was washed with 35 ml of solubilization buffer at 1 ml/min. A linear gradient of solubilization buffer with increasing concentration of refolding buffer (50 mM Tris-HCL pH 7.4, 300 mM NaCl) was applied at 1 ml/min. for 1 hour until 100% refolding buffer was reached. The column was then further washed with 25 ml of refolding buffer. The refolded protein was then eluted from the column with elution buffer (50 mM Tris-HCl, 300 mM NaCl, 400 mM Imidazole). Protein containing fractions were pooled and desalted on PD10 columns (Amersham) equilibrated with PBS. The desalted protein was then aliquoted and stored at −80° C.

Example 2: Cells Expressing Interferon Gamma on Cell Surface

Chinese hamster ovary (CHO) cells (available from ATCC) were stably transfected with c-myc-tagged human IFNγ cDNA. cDNAs were subcloned into pcDNA 3.1 plasmids (Invitrogen, Carlsbad Calif.) containing neomycin resistance genes. Transfectants were selected by using this antibiotic, and successive cell sorting was accomplished by flow cytometry using an anti-6×His (Sigma) antibody. Surface expression of human IFNγ was confirmed via flow cytometry using an anti-IFNγ mAb (clone B27, Becton Dickinson, Franklin Lakes N.J.).

Example 3: Screening of Human scFv Libraries

General procedures for construction and handling of human scFv libraries are described in Vaughan et al., (Nat. Biotech. 1996, 14:309-314), hereby incorporated by reference in its entirety. Libraries of human scFv were screened against hIFNγ according to the following procedure.

Liquid Phase Selections.

Aliquots of scFv phage libraries ($10^{12}$ Pfu) obtained from Cambridge Antibody Technology (Cambridge, UK) were blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated hIFNγ (100 nM) for two hours at room temperature on a rotary mixer. Beads were captured using a magnetic stand followed by four washes with PBS/0.1% Tween 20 and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2×TY-AG (2×TY media containing 100 μg/ml ampicilin and 2% glucose) and spread on 2×TYAG agar Bioassay plates. After overnight incubation at 30° C. 10 ml of 2×TYAG was added to the plates and the cells were scraped form the surface and transferred to a 50 ml polypropylene tube. 2×TYAG containing 50% glycerol was added to the cell suspension to obtain a final concentration of 17% glycerol. Aliquots of the selection round were kept at −80° C.

Cell Surface Selections.

Aliquots of scFv phage libraries ($10^{12}$ Pfu) obtained from Cambridge Antibody Technology (Cambridge, UK) were blocked with PBS containing 3% (w/v) skimmed milk for one hour at room temperature on a rotary mixer. Blocked phage was then deselected for one hour at 37° C./5% $CO_2$ on CHO cells transfected with an empty pDisplay vector (in a T75 flask 80% confluence) and that had been previously blocked with PBS containing 2% (w/v) skimmed milk. Deselected phage was then incubated CHO-pDisplay-hIFNγ cells for one hour at room temperature with gentle shaking. Cells were then washed ten times with PBS. Bound phage was eluted by adding directly 10 ml of exponentially growing TG1 to the T75 flask and incubating for one hour at 37° C. with slow shaking. An aliquot of the infected TG1 was serial diluted to titer the selection output. Infected TG1 were spun at 3000 rpm for 15 minutes and re-suspended in 0.5 ml 2×TY-AG (2×TY media containing 100 μg/ml ampicilin and 2% glucose) and spread on 2×TYAG agar Bioassay plates. After overnight incubation at 30° C. 10 ml of 2×TYAG was added to the plates and the cells were scraped form the surface and transferred to a 50 ml polypropylene tube. 2×TYAG containing 50% glycerol was added to the cell suspension to obtain a final concentration of 17% glycerol. Aliquots of the selection round were kept at −80° C.

Phage Rescue.

100 μl of cell suspension obtained from previous selection rounds were added to 20 ml of 2×TYAG and grown at 37° C. with agitation (240 rpm) until an $OD_{600}$ of 0.3 to 0.5 was reached. The culture was then super-infected with $3.3 \times 10^{10}$ MK13K07 helper phage and incubated for one hour at 37° C. (150 rpm). The medium was then changed by centrifugating the cells at 2000 rpm for 10 minutes, removing the medium and resuspending the pellet in 20 ml of 2×TY-AK (100 μg/ml ampicilin; 50 μg/ml kanamycin). The culture was then grown overnight at 30° C. (240 rpm).

Monoclonal Phage Rescue for ELISA.

Single clones were picked into a microtiter plate containing 150 μl of 2×TYAG media (2% glucose) per well and grown at 37° C. (100-120 rpm) for 5-6 h. M13K07 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells re-suspended in 150 μA 2×TYAK medium and grown overnight at 30° C. (120 rpm). For the ELISA, the phage are blocked by adding 150 μl of 2× concentration PBS containing 5% skimmed milk powder followed by one hour incubation at room temperature. The plates were then centrifuged 10 minutes at 3000 rpm and the phage containing supernatant used for the ELISA.

Phage ELISA.

ELISA plates (Maxisorb, NUNC) were coated overnight with 2 µg/ml hIFNγ in PBS. Control plates were coated with 2 µg/ml BSA. Plates were then blocked with 3% skimmed milk/PBS at room temperature for 1 h. Plates were washed 3 times with PBS 0.05% Tween 20 before transferring the pre-blocked phage supernatants and incubation for one hour at room temperature. Plates were then washed 3 times with PBS 0.05% Tween 20. 50 µl of 3% skimmed milk/PBS containing (HRP)-conjugated anti-M13 antibody (Amersham, diluted 1:10,000) to each well. Following incubation at room temperature for 1 hr, the plates were washed 5 times with PBS 0.05% Tween 20. The ELISA was then revealed by adding 50 µl of TMB (Sigma) and 50 µl of $2NH_2SO_4$ to stop the reaction. Absorption intensity was read at 450 nm.

Phage Clone Sequencing

Single clones were placed in a microtiter plate containing 150 µl of 2×TYAG media (2% glucose) per well and grown at 30° C. (120 rpm) overnight. The next day 5 µl of culture was transferred into another plate containing 45 µl of $dH_2O$ and mixed. The plates was then frozen at −20° C. After thawing, 1 µl of this suspension was used for PCR amplification using standard PCR protocols with primer specific for pCANTAB6: mycseq, 5'-CTCTTCTGAGAT-GAGTTTTTG-3' (SEQ ID NO:100) and gene3leader, 5'-TT-ATTATTCGCAATTCCTTTAGTTGTTCCT-3' (SEQ ID NO:101).

The PCR reactions were purified in 96 well format using the Montage PCRµ96 system (Millipore). 5 µl of the eluted DNA was sequencing using the mycseq and gene3leader primers.

ScFv Periplasmic Preparation for Functional Tests.

Individual clones were inoculated into a deep well microtiter plate containing 0.9 ml of 2×TYAG media (0.1% glucose) per well and grown at 37° C. for 5-6 h (250 rpm). 100 µl per well of 0.2 mM IPTG in 2×TY medium were then added to give a final concentration of 0.02 mM IPTG. Plates were then incubated overnight at 30° C. with shaking at 250 rpm. The deep-well plates were centrifuged at 2,500 rpm for 10 min and the supernatant carefully removed. The pellets were re-suspended in 150 µl TES buffer (50 mM Tris/HCl (pH 8), 1 mM EDTA (pH 8), 20% sucrose, complemented with Complete protease inhibitor, Roche). A hypotonic shock was produced by adding 150 µl of diluted TES buffer (1:5 TES:water dilution) and incubation on ice for 30 min. Plates were then centrifuged at 4000 rpm for 10 minutes to remove cells and debris. The supernatants were carefully transferred into another microtiter plate and kept on ice for immediate testing in functional assays or ELISAs.

Large Scale scFv Purification

A starter culture of 1 ml of 2×TYAG was inoculated with a single colony from a freshly streaked 2×TYAG agar plate and incubated with shaking (240 rpm) at 37° C. for 5 hours. 0.9 ml of this culture was used to inoculate a 400 ml culture of the same media and was grown overnight at 30° C. with vigorous shaking (300 rpm).

The next day the culture was induced by adding 400 µl of 1M IPTG and incubation was continued for an additional 3 hours. The cells were collected by centrifugation at 5,000 rpm for 10 minutes at 4° C. Pelleted cells were resuspended in 10 ml of ice-cold TES buffer complemented with protease inhibitors as described above. Osmotic shock was achieved by adding 15 ml of 1:5 diluted TES buffer and incubation for 1 hour on ice. Cells were centrifuged at 10,000 rpm for 20 minutes at 4° C. to pellet cell debris. The supernatant was carefully transferred to a fresh tube. Imidazole was added to the supernatant to a final concentration of 10 mM. 1 ml of Ni-NTA resin (Qiagen), equilibrated in PBS was added to each tube and incubated on a rotary mixer at 4° C. (20 rpm) for 1 hour.

The tubes were centrifuged at 2,000 rpm for 5 minutes and the supernatant carefully removed. The pelleted resin was resuspended in 10 ml of cold (4° C.) Wash buffer 1 (50 mM $NaH_2PO_4$, 300 mM NaCl, 10 mM imidazole, pH to 8.0). The suspension was added to a polyprep column (Biorad). 8 ml of cold Wash Buffer 2 (50 mM $NaH_2PO_4$, 300 mM NaCl, 20 mM imidazole, pH to 8.0) were used to wash the column by gravity flow. The scFv were eluted from the column with 2 ml of Elution buffer (50 mM $NaH_2PO_4$, 300 mM NaCl, 250 mM imidazole, pH to 8.0). Fractions were analyzed by absorption at 280 nm and protein containing fractions were pooled before buffer exchange on a PD10 desalting column (Amersham) equilibrated with PBS. The scFv in PBS were analyzed by SDS-PAGE and quantified by absorption at 280 nm. The purified scFv were aliquoted and stored at −20° C. and at 4° C.

Example 4: scFv Extract Inhibition of Interferon Gamma-Induced Reporter Gene Expression Periplasmic scFv extracts of various huIFNγ antibodies were produced as described above. A high through-put screen cell-based assay was used for the identification of single chain variable fragment (scFv) blockers of IFNγ activity. A reporter gene (firefly luciferase), driven by the IFNγ-inducible GBP1 promoter, was transfected into the human melanoma cell line, Me67.8. Both scFv and IFNγ were added to the cell culture concomitantly. Following a 6 hour incubation time, the luciferase reporter assay was performed. The scFv found to inhibit the induction of firefly luciferase were retained for further validation.

Several scFv extracts inhibited the IFNγ-induced reporter gene in a dose dependant fashion (FIG. 15). For each scFv clone shown in FIG. 15, various concentrations (2.7, 0.68, 0.17, 0.043 and 0.011 nM) were tested as shown by the columns above each clone name (descending concentration from left to right). The percentage inhibition exhibited by each scFv extract at these various concentrations is shown in Table 3 below.

TABLE 3

Percentage inhibition of IFNγ-induced reporter gene expression by periplasmic scFV extracts

| [scFv] nM | A6 | H8 | A8 | D8 | C10 | B4 | B9 | F9 | A4 | E1 | C9 | G7 | G10 | D6 | G6 | G9 | D3 | F8 |
|---|---|---|---|---|---|---|---|---|---|---|---|---|---|---|---|---|---|---|
| 2.7 | 82 | 80 | 85 | 60 | 63 | 63 | 62 | 68 | 36 | 43 | 56 | 75 | 47 | 82 | 73 | 52 | 69 | 64 |
| 0.68 | 92 | 75 | 86 | 60 | 50 | 49 | 53 | 32 | 1 | 68 | 67 | 73 | 44 | 73 | 66 | 12 | 55 | 64 |
| 0.17 | 100 | 65 | 87 | 40 | 53 | 21 | 56 | 3 | 0 | 38 | 58 | 24 | 0 | 31 | 25 | 0 | 36 | 48 |
| 0.043 | 87 | 26 | 65 | 10 | 34 | 5 | 0 | 0 | 0 | 10 | 33 | 38 | 0 | 11 | 0 | 0 | 28 | 0 |
| 0.011 | 0 | 0 | 13 | 0 | 19 | 0 | 0 | 0 | 0 | 0 | 0 | 4 | 0 | 0 | 0 | 0 | 20 | 0 |

Example 5: scFv Inhibition of Interferon Gamma-Induced MHC Class II Expression A flow cytometric assay was implemented to identify fully human IgG antibodies, or fragments thereof, capable of blocking the expression of IFNγ-induced MHC class II molecules. Following the plating of Me67.8 cells, 5 ng/ml recombinant human IFNγ was added to cultures in the presence of various concentrations of candidate fully human anti-IFNγ monoclonal antibodies. Following 48 h in culture, cells were stained with fluorescently labeled anti-human MHC class II antibody (HLA-DR) and analyzed using a FACSCalibur®. Thus, the $IC_{50}$ (where 50% of the IFNγ-induced MHC class II expression is inhibited, i.e., 50% inhibitory concentration), for each candidate antibody is measured.

Purified fully human scFv were produced as described above in Example 1. The effect of the scFv on IFNγ-induced MHC class II expression on melanoma cells was evaluated using the flow cytometric cell-based assay described above. These scFv inhibited IFNγ-induced MHC II expression on melanoma cells. (FIG. 16, Panels 1-12). The ability of these scFv clones to inhibit IFNγ-induced MHC II expression on melanoma cells was compared to a mouse anti-human IFNγ mAb referred to herein as 16C3. scFv clones (-) and the mouse anti-human IFNγ mAb 16C3 ( - - - ) are depicted in FIG. 16.

Example 6: Reformatting scFv into IgG Format

Purified fully human scFv were produced as described above in Example 1. The $V_H$ and $V_L$ sequence of selected scFv were amplified with specific oligonucleotides introducing a leader sequence and a HindIII restriction site at the 5' end. An ApaI or an AvrII site was introduced at the 3' end of the heavy and light chain sequence, respectively. The amplified $V_H$ sequences were digested HindIII/ApaI and cloned into the pCon_gamma1 expression vector (LONZA, Basel, Switzerland). The amplified $V_L$ sequences were digested HindIII/AvrII and cloned into the pCon_lambda2 expression vector (LONZA). The constructions were verified by sequencing before transfection into mammalian cells.

The $V_H$ and $V_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of $6\times10^5$ cells per well in 2 ml culture media containing fetal bovine serum. The expression vectors, encoding the candidate $V_H$ and $V_L$ sequences, were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G columns.

Reformatted fully IgG was purified from serum-free supernatants from transfected cells using Protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

Example 7: Inhibition of Interferon Gamma-Induced MHC Class II Expression by Reformatted scFv sFv were reformatted into an IgG format as described above. The effect of the IgG clones on IFNγ-induced MHC class II expression on melanoma cells was evaluated using the flow cytometric cell-based assay described above in Example 2. As shown in FIG. 17, Panels 1-7, these IgG clones inhibited IFNγ-induced MHC II expression on melanoma cells. The ability of these IgG clones to inhibit IFNγ-induced MHC II expression on melanoma cells was compared to the mouse anti-human IFNγ mAb 16C3 and the R&D Systems mouse anti-human IFNγ antibody MAB285. Fully IgG clones (-x-), the mouse anti-human IFNγ mAb 16C3 (-▲-), and the R&D Systems, Inc. (Minneapolis, Minn.) mouse anti-human IFNγ MAB285 (-•-) are depicted.

The $IC_{50}$ values for these IgG clones are shown below in Table 4.

TABLE 4

$IC_{50}$ analysis of fully human anti-IFNγ monoclonal antibodies.

| IgG mAb | MHC II Inhibition Cell-Based Assay $IC_{50}$ |
|---|---|
| 16C3 | 100 pM |
| MAB285 | 400 pM |
| AC1.2R3P2_A6 | 41 pM |
| AD14R4P1_B9 | 322 pM |
| AC1.4R4P2_C10 | 203 pM |
| AC1.2R3P2_D8 | 708 pM |
| AD1.3R3P5_F8 | 1525 pM |
| AD1.3R3P6_F9 | 185 pM |
| AD14R4P2_G7 | 233 pM |

Example 8: Back-Mutation of huIFNγ Antibody Clone to Germline Sequence

In the studies described herein, the nucleotides and amino acid residues in the nucleic acid and amino acid sequence of the A6 clone were mutated to correspond to the nucleotide or amino acid residue found in the germline sequence. This process is referred to herein as "back-mutation".

A6 Heavy Chain:

The immunoglobulin heavy variable gene of antibody A6 had a 100% homology to the human germ line DP-47 or IGHV3-23 (GenBank Accession number M99660). The immunoglobulin heavy joining (IGHJ) region of A6 was compared to the six human functional IGHJ regions. The IGHJ region of A6 was identified as IGHJ2 (Table 5A below), but had a better overall homology with IGHJ5-02 (Table 5B below). The original IGHJ region of A6 was therefore mutated to correspond to the sequence of IGHJ5-02, but only for the sequence outside the CDR3. Mutated nucleotides and amino acid residues are shown in boxes in Tables 5A and 5B, and the CDR regions are underlined.

TABLE 5A

Comparison between A6 and human functional IGHJ2 genes

```
ACCACAGTGGTTCGACCCCTGGGGCCGGGGCACCCTGGTCACCGTCTCGAGT A6 (SEQ ID NO: 109)

P  H  W  F  D  P  W  G  R  G  T  L  V  T  V  S  S (SEQ ID NO: 110)

CTACTGGTACTTCGATCTCTGGGGCCGTGGCACCCTGGTCACTGTCTCCTCA IGHJ2 (SEQ ID NO: 111)

Y  W  Y  F  D  L  W  G  R  G  T  L  V  T  V  S  S (SEQ ID NO: 112)

CDR 3
```

TABLE 5B

Comparison between A6 and human functional IGHJ5-02 gene

```
CACACTGGTTCGACCCCTGGGGCCGGGGCACCCTGGTCACCGTCTCGAGT A6 (SEQ ID NO: 113)

H  W  F  D  P  W  G  R  G  T  L  V  T  V  S  S (SEQ ID NO: 114)

ACAACTGGTTCGACCCCTGGGGCCAGGGAACCCTGGTCACCGTCTCCTCA IGHJ5-02 (SEQ ID NO: 115)

N  W  F  D  P  W  G  Q  G  T  L  V  T  V  S  S (SEQ ID NO: 116)

CDR 3
```

A6 Light Chain:

The immunoglobulin lambda variable gene (VL) of antibody A6 belongs to the IGLV6-57 or V1-22 subgroup (GenBank Accession Number Z73673). A6-VL has 7 mutations compared to IGLV6-57, three in the CDRs and four in the frameworks (Table 6 below). The mutated nucleotides and amino acid residues are shown in boxes in Table 6, and the CDR regions are underlined.

The four mutations in framework regions are: Ser to Ala in framework 2 region at Kabat position 43; Ser to Thr in framework 3 region at Kabat position 72; Lys to Glu and Thr to Ala in framework 3 region at Kabat positions 79 and 80, respectively. The four mutations in the framework regions were changed first individually, then all together back to the corresponding human germ line residue. The mutations of these four residues back to the corresponding human germ line amino acid did not alter in any way the binding affinity of the NI-0501 antibody, also referred to herein as "backmutated A6", to its target antigen as compared to the A6 antibody. The mutations from the A6 VL sequence to the corresponding germ line residue in CDR1 (Ala to Val) and CDR2 (Gln to Arg) were carried out and were shown not to modify the overall affinity for huIFNγ of the NI-0501 antibody (backmutated A6) as compared to the A6 antibody.

TABLE 6

Comparison between A6 and human functional IGHV6-57 gene

```
                                     CDR 1            43        CDR 2

Human IGLV6-57  NFMLTQPHSVSESPGKTVTISCTRSSGSIASNYVQWYQQRPGSSPTTVIYEDNQRPSGVP 60

A6-VL           NFMLTQPHSVSESPGKTVTISCTRSSGSIVSNYVQWYQQRPGSAPTTVIYEDNRRPSGVP 60

***************************** ************ ********* ******

72      79,80       CDR 3

Human IGLV6-57  DRFSGSIDSSSNSASLTISGLKTEDEADYYCQSYDSSN-------------- 98 (SEQ ID NO: 117)

A6-VL           DRFSGSIDSSSNTASLTISGLEAEDEADYYCQSYDGSNRWMFGGGTKLTVLG 112 (SEQ ID NO: 118)

************:*******:*:************ **
```

The complete sequences of the NI-0501 heavy and light chains are set forth in FIGS. 1A-1D. The nucleotides and amino acid residues that were backmutated to produce the NI-0501 antibody (i.e., those nucleotides and residues that were changed from the original A6 sequence) are underlined and italicized in FIGS. 1A and 1C.

Example 9: Affinity and Binding Kinetics of huIFNγ Antibody

Figure 18:
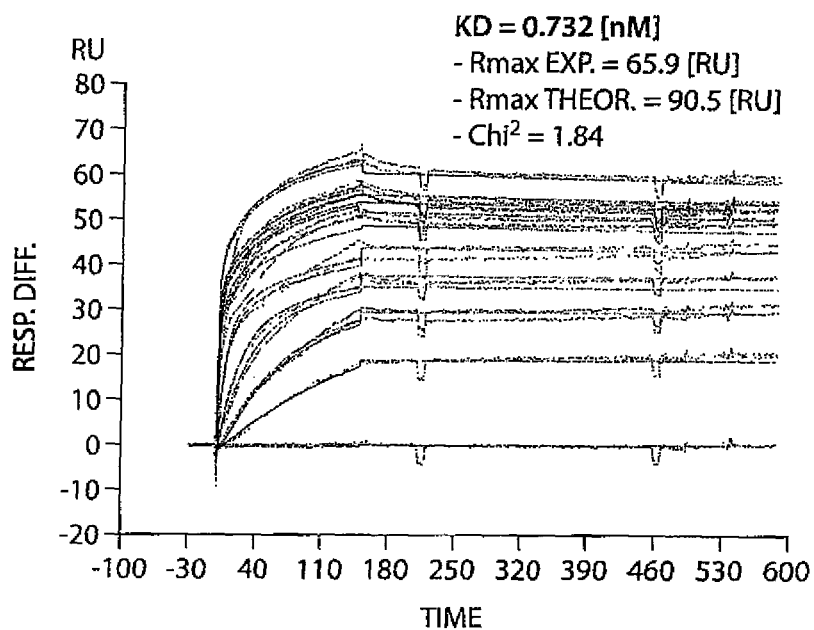
FIG. 18 is a graph depicting the affinity of the NI-0501 huIFNγ antibody for human IFNγ.

The affinity and binding kinetics of the NI-0501 huIFNγ antibody were characterized on a Biacore 2000 instrument (Biacore AB, Uppsala, Sweden). 200 RU of NI-0501 were immobilized by EDC/NHS chemistry on a C1 Biacore chip. Binding was measured by passing hIFNγ (R&D Systems) in HBS-EP buffer at concentrations between 200 nM and 1 nM. The flow rate was 100 μl/minute and the temperature set at 25° C. The data was fitted according to 1:1 Langmuir model and the $K_{on}$, $K_{off}$ and $K_D$ values determined (FIG. 18).

Example 10: Activity of huIFNγ Antibody

Figure 19:
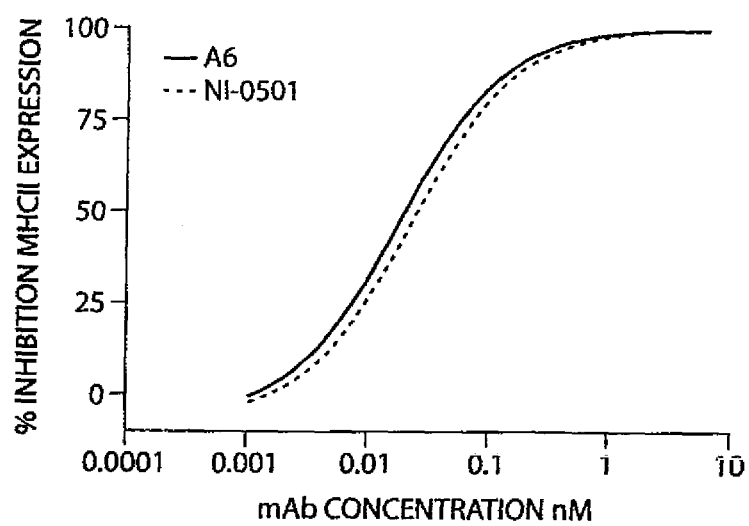
FIG. 19 is a graph comparing the activity of antibodies produced by the A6 and NI-0501 (also referred to herein as "A6 back-mutated to germline" or "back-mutated A6") clones.

The activity of the NI-0501 huIFNγ antibody was compared to the activity of the antibody produced by the clone A6 (i.e., the A6 huIFNγ antibody). In this study, the ability of each huIFNγ antibody to inhibit recombinant human IFNγ (rhuIFNγ)-induced MHC class II upregulation on the human melanoma cell line, Me67.8 was evaluated. Briefly, Me67.8 melanoma cells were incubated with rhuIFNγ, in the presence of NI-0501 or the A6 huIFNγ antibody for 48-72 h. MHC class II upregulation was measured as described above in Example 5. The two antibodies presented a similar activity, which demonstrates that the backmutations in the NI-0501 huIFNγ antibody did not modify the activity of the antibody (FIG. 19).

Figure 20:
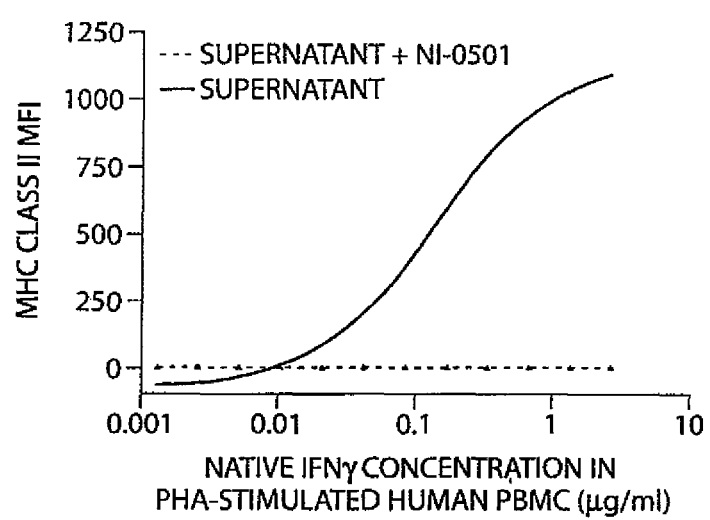
FIG. 20 is a graph depicting the activity of the NI-0501 huIFNγ antibody on native human IFNγ.
Figure 21A:
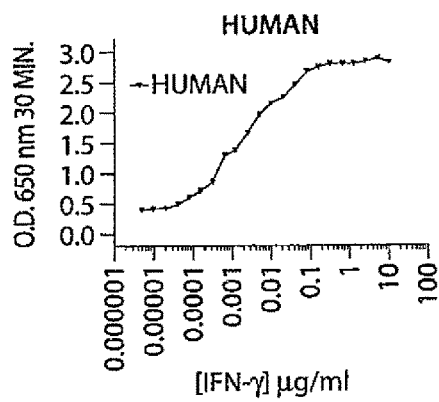
FIGS. 21A-21F are a series of graphs depicting the binding of the NI-0501 huIFNγ antibody with recombinant IFNγ from various species.
Figure 21B:
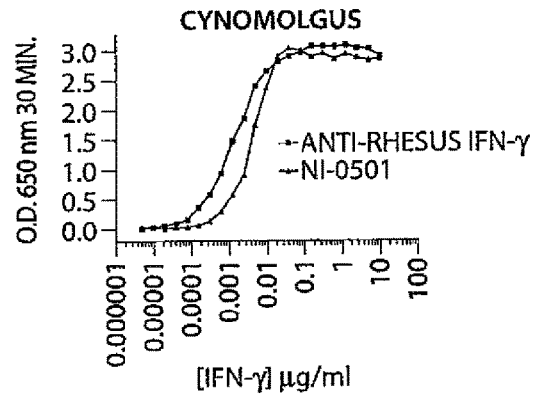
Figure 21C:
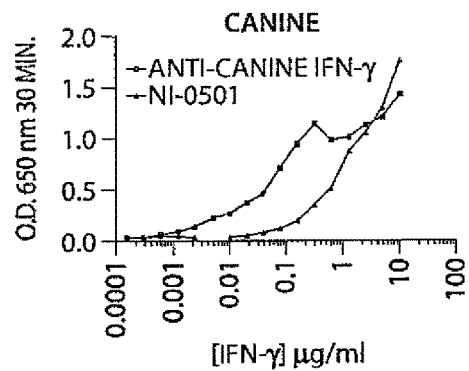
Figure 21D:
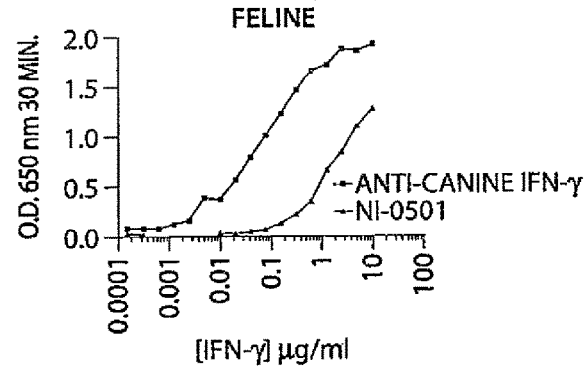
Figure 21E:
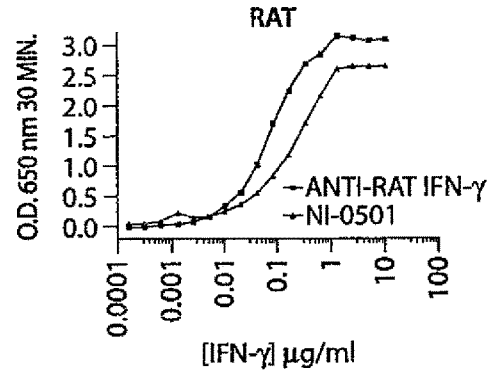
Figure 21F:
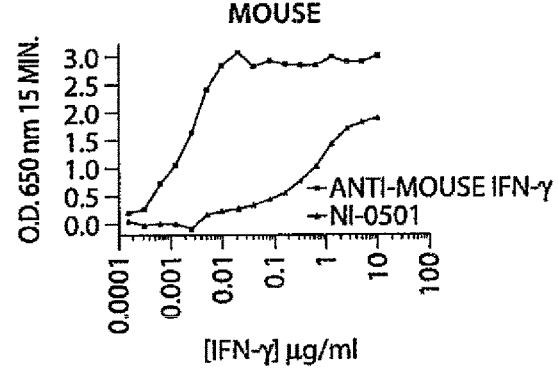

The activity of the NI-0501 huIFNγ antibody was then tested on native IFNγ. In this study, human peripheral blood mononuclear cells (PBMCs) were activated with 1 μg/ml of the mitogen PHA for 48 h, and supernatants were tested via ELISA for the presence of native IFNγ. This supernatant was then used to stimulate the MHC class II upregulation on Me67.8 cells. NI-0501 was able to neutralize the MHC class II upregulation induced by native human IFNγ (FIG. 20).

Example 11: Cross-Reactivity of huIFNγ Antibody

Binding Assay

NI-0501 was tested for its ability to bind to IFNγ using a Sandwich ELISA format assay. Briefly, IFNγ from the species mentioned in the title of each graph shown in FIG. 21 was captured with pre-coated NI-0501 (-▲-) or the control anti-species IFNγ mAb (-■-). The IFNγ from each species was detected using a polyclonal antibody specific for the IFNγ in that assay. As seen in FIG. 21, NI-0501 binding to rat IFNγ is similar to the control antibody, but not for the other species, excluding cynomolgus monkey.

Figure 22:
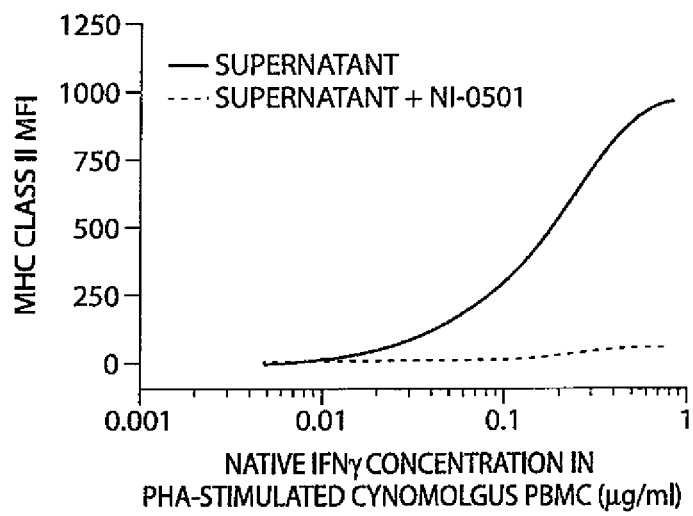
FIG. 22 is a graph depicting the ability of the NI-0501 huIFNγ antibody to neutralize the MHC class II upregulation induced by native cynomolgus IFNγ.

Neutralization of IFNγ Activity:

The antibody NI-0501 was tested for its ability to neutralize or inhibit recombinant IFNγ proteins from several different species. Briefly, recombinant IFNγ from the various tested species was placed in culture with Me67.8 cells in the presence or absence of NI-0501 for 48-72 h. MHC class II upregulation was measured as described above in Example 5. The cross-reactivity to, and neutralization of, cynomolgus IFNγ was demonstrated by inhibiting the MHC class II upregulation on the human melanoma cell line, Me67.8 (FIG. 22). NI-0501 was able to inhibit IFNγ from cynomolgus monkey but could not neutralize IFNγ from the other tested species, demonstrating no cross reactivity the antibody with these species (Table 7).

TABLE 7

| Cross Reactivity of NI-0501 | | | | | | | | |
|---|---|---|---|---|---|---|---|---|
| NI-0501 | nhuIFNγ | rhuIFNγ | ncyIFNγ | rcyIFNγ | rdIFNγ | rcIFNγ | rrIFNγ | rmIFNγ |
| Binding | + | + | + | + | − | − | − | − |
| Neutralization | + | + | + | + | * | * | * | * | nhu = native human IFNγ
rhu = recombinant human IFNγ
ncy = native cynomolgus IFNγ
rcy = recombinant cynomolgus IFNγ
rd = recombinant dog IFNγ
rc = recombinant cat IFNγ
rr = recombinant rat IFNγ
rm = recombinant mouse IFNγ
+ = cross-react
− = do not cross-react
* = not tested In addition, cynomolgus PBMCs were activated with 1 μg/ml of the mitogen PHA for 48 h, and supernatants were tested via ELISA for the presence of native IFNγ. This supernatant was then used to stimulate the MHC class II upregulation on Me67.8. NI-0501 was able to neutralize the MHC class II upregulation induced by native cynomolgus IFNγ (FIG. 22).

Example 12: Biological Activity of huIFNγ Antibody

The studies described herein were designed to test the biological activity of the NI-0501 huIFNγ antibody upon administration to cynomolgus monkeys. NI-0501 was chosen for the safety and pharmacokinetics (PK) studies described herein because this huIFNγ antibody was found to cross-react with the IFNγ from cynomolgus monkeys, as described above. To evaluate adverse clinical effects after multiple intravenous infusions, monkeys are infused with the following doses: 30 mg/kg, 100 mg/kg and 200 mg/kg.

In mice with a disrupted IFNγ gene, decreased levels of IgG2a and increased levels of IgG1 were observed in response to KLH immunization, demonstrating the correlation between IFNγ and the IgG response. During the 13 week main toxicology study, monkeys are immunized with KLH in Incomplete Freund's Adjuvant (IFA). A typical immune response to KLH/IFA in monkeys, co-treated with placebo, elicits a KLH-specific IgM and IgG response detectable in the serum. These studies are designed to evaluate whether neutralizing IFNγ in NI-0501-treated monkeys that were immunized with KLH in IFA, alters the KLH-specific IgG titer.

Example 13: Modulation of IFNγ Activity Using huIFNγ Antibodies

Figure 23:
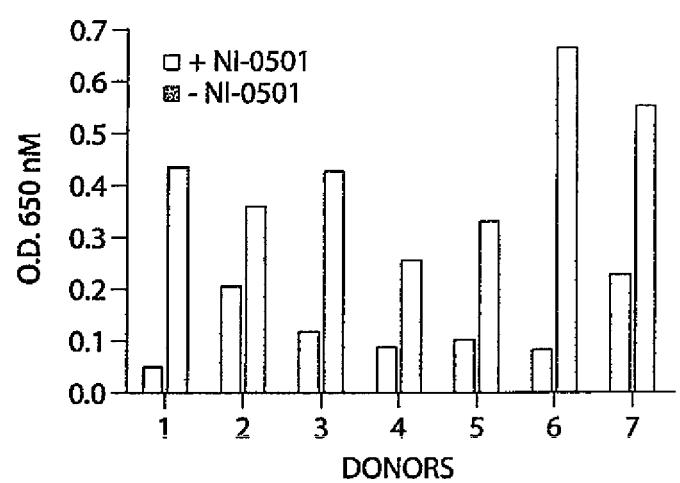
FIG. 23 is a graph depicting the ability of the NI-0501 huIFNγ antibody to block IFNγ-induced IP-10 production in whole blood.

The production of the chemokine IP-10 is up-regulated by IFNγ in several different cell lines. Based on this observation a whole blood assay was developed. In this whole blood assay, whole blood samples from several donors were mixed with a fixed concentration of IFNγ and different concentrations of NI-0501. After incubation, IP-10 levels were measured by ELISA as a means for evaluating the efficacy of the anti-IFNγ antibody to block the production of IP-10 (FIG. 23).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fully human monoclonal anti-IFNγ antibody or fragment thereof, wherein said antibody comprises:
   (a) a $V_H$ CDR1 region comprising the amino acid sequence SYAMS (SEQ ID NO:3) or SNAMS (SEQ ID NO:43);
   (b) a $V_H$ CDR2 region comprising the amino acid sequence AISGSGGSTYYADSVKG (SEQ ID NO:4) or TLTGSGGTAYYADSVEG (SEQ ID NO:44),
   (c) a $V_H$ CDR3 region comprising an amino acid sequence selected from the group consisting of DGSSGWYVPHWFDP (SEQ ID NO:5); DHSSGWYVISGMDV (SEQ ID NO:13); DLTVGGPWYYFDY (SEQ ID NO:21); DGWNALGWLES (SEQ ID NO:29); GTELVGGGLDN (SEQ ID NO:45); RSFDSGGSFEY (SEQ ID NO:64); VGSWYLEDFDI (SEQ ID NO:69); GGNYGDYFDYFDY (SEQ ID NO:76); and DFWVITSGNDY (SEQ ID NO:89),
   (d) a $V_L$ CDR1 region comprising an amino acid sequence selected from the group consisting of TRSSGSIASNYVQ (SEQ ID NO:8); TRSSGSIASNYVQ (SEQ ID NO:16); TRSGGSIGSYYVQ (SEQ ID NO:32); TRSSGTIASNYVQ (SEQ ID NO:39); TGSGGSIATNYVQ (SEQ ID NO:48); TGSSGSIASNYVQ (SEQ ID NO:55); TRSSGSIASNYVH (SEQ ID NO:72); TGRNGNIASNYVQ (SEQ ID NO:84); AGSSGSIASNYVQ (SEQ ID NO:97) and TRSSGSIVSNYVQ (SEQ ID NO:106);
   (e) a $V_L$ CDR2 region comprising an amino acid sequence selected from the group consisting of EDNQRPS (SEQ ID NO:9); EDNQRPS (SEQ ID NO:17); DDDQRPS (SEQ ID NO:25); DDKKRPS (SEQ ID NO:33); EDTQRPS (SEQ ID NO:85) and EDNRRPS (SEQ ID NO:107); and
   (f) a $V_L$ CDR3 region comprising an amino acid sequence selected from the group consisting of QSYDGSNRWM (SEQ ID NO:10); QSNDSDNVV (SEQ ID NO:18); QSYDSSNVV (SEQ ID NO:26); QSYDSNNLVV (SEQ ID NO:34); QSYDNSNHWV (SEQ ID NO:40); QSYDSDNHHVV (SEQ ID NO:49); QSYDSSNQEVV (SEQ ID NO:56); QSYDSNNFWV (SEQ ID NO:61); QSSDTTYHGGVV (SEQ ID NO:73); QSYEGF (SEQ ID NO:79); QSSDSNRVL (SEQ ID NO:86); QSFDSTNLVV (SEQ ID NO:92); and QSYSYNNQVV (SEQ ID NO:98),
   wherein said antibody binds IFNγ.

2. The antibody of claim 1, wherein said antibody is an IgG isotype.

3. An isolated fully human monoclonal antibody, wherein said antibody comprises a heavy chain variable amino acid sequence selected from the group consisting of SEQ ID NOS: 2, 12, 20, 28, 36, 42, 51, 58, 63, 68, 75, 81, 88, 94 or 103 and a light chain variable amino acid sequence selected from the group consisting of SEQ ID NOS: 7, 15, 23, 31, 38, 47, 54, 60, 66, 71, 78, 83, 91, 96 or 105, wherein said antibody binds IFNγ.

4. A pharmaceutical composition comprising an antibody of claim 1 and a carrier.

5. A pharmaceutical composition comprising an antibody of claim 3 and a carrier.

6. A method of alleviating a symptom of an autoimmune disease or inflammatory disorder, the method comprising administering an antibody of claim 1 to a subject in need thereof in an amount sufficient to alleviate the symptom of the autoimmune disease or inflammatory disorder in the subject, wherein the autoimmune disease or inflammatory disorder is selected from the group consisting of Crohn's Disease, psoriasis, rheumatoid arthritis, and secondary progressive multiple sclerosis.

7. The method of claim 6, wherein said subject is a human.

8. The method of claim 6, wherein said antibody comprises a $V_H$ CDR1 region comprising the amino acid sequence SYAMS (SEQ ID NO:3); a $V_H$ CDR2 region comprising the amino acid sequence AISGSGGSTYYADSVKG (SEQ ID NO:4), a $V_H$ CDR3 region comprising the amino acid sequence DGSSGWYVPHWFDP (SEQ ID NO:5); a $V_L$ CDR1 region comprising the amino acid sequence TRSSGSIASNYVQ (SEQ ID NO:8); a $V_L$ CDR2 region comprising the amino acid sequence EDNQRPS (SEQ ID NO:9); and a $V_L$ CDR3 region comprising an amino acid sequence QSYDGSNRWM (SEQ ID NO:10).

9. The method of claim 6, wherein said antibody comprises a heavy chain variable region comprising the amino acid sequence of SEQ ID NO: 2 and a light chain variable region comprising the amino acid sequence of SEQ ID NO: 7.

10. The method of claim 6, wherein said antibody is administered intravenously.

* * * * *